(12) United States Patent
Majuru et al.

(10) Patent No.: US 8,039,018 B2
(45) Date of Patent: Oct. 18, 2011

(54) SOLID DOSAGE FORM OF WETTED HEPARIN

(75) Inventors: Shingai Majuru, Brewster, NY (US); Brahma Singh, Jamaica, NY (US); Nikhil Dhoot, Dombivli (IN)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 1274 days.

(21) Appl. No.: 11/568,749

(22) PCT Filed: May 6, 2005

(86) PCT No.: PCT/US2005/016012
§ 371 (c)(1),
(2), (4) Date: Jan. 12, 2007

(87) PCT Pub. No.: WO2005/107773
PCT Pub. Date: Nov. 17, 2005

(65) Prior Publication Data
US 2007/0224262 A1    Sep. 27, 2007

Related U.S. Application Data

(60) Provisional application No. 60/569,475, filed on May 6, 2004, provisional application No. 60/572,679, filed on May 19, 2004, provisional application No. 60/598,978, filed on Aug. 4, 2004.

(51) Int. Cl.
*A61K 9/48* (2006.01)
*A01N 57/00* (2006.01)
(52) U.S. Cl. ............................ 424/451; 514/93; 585/1
(58) Field of Classification Search .................. 514/937, 514/93; 585/1; 424/451
See application file for complete search history.

(56) References Cited

U.S. PATENT DOCUMENTS

| | | | |
|---|---|---|---|
| 3,510,561 A | 5/1970 | Koh | |
| 5,541,155 A | 7/1996 | Leone-Bay et al. | |
| 5,643,957 A | 7/1997 | Leone-Bay et al. | |
| 5,650,386 A | 7/1997 | Leone-Bay et al. | |
| 5,693,338 A | 12/1997 | Milstein et al. | |
| 5,714,477 A | 2/1998 | Einarsson et al. | |
| 5,820,881 A | 10/1998 | Milstein et al. | |
| 5,866,536 A | 2/1999 | Leone-Bay et al. | |
| 5,955,503 A | 9/1999 | Leone-Bay et al. | |
| 5,965,121 A | 10/1999 | Leone-Bay et al. | |
| 5,976,569 A | 11/1999 | Milstein et al. | |
| 5,989,539 A | 11/1999 | Leone-Bay et al. | |
| 6,001,347 A | 12/1999 | Leone-Bay et al. | |
| 6,071,510 A | 6/2000 | Leone-Bay et al. | |
| 6,100,298 A | 8/2000 | Leone-Bay et al. | |
| 6,180,140 B1 | 1/2001 | Leone-Bay et al. | |
| 6,221,367 B1 | 4/2001 | Milstein et al. | |
| 6,242,495 B1 | 6/2001 | Leone-Bay et al. | |
| 6,245,359 B1 | 6/2001 | Milstein et al. | |
| 6,261,601 B1 | 7/2001 | Talwar et al. | |
| 6,313,088 B1 | 11/2001 | Leone-Bay et al. | |
| 6,331,318 B1 | 12/2001 | Milstein | |
| 6,344,213 B1 | 2/2002 | Leone-Bay et al. | |
| 6,346,242 B1 | 2/2002 | Leone-Bay et al. | |
| 6,358,504 B1 | 3/2002 | Leone-Bay et al. | |
| 6,375,983 B1 | 4/2002 | Kantor et al. | |
| 6,384,278 B1 | 5/2002 | Tang et al. | |
| 6,391,303 B1 | 5/2002 | Haas et al. | |
| 6,395,774 B1 | 5/2002 | Milstein | |
| 6,399,798 B2 | 6/2002 | Gschneidner et al. | |
| 6,413,550 B1 | 7/2002 | Milstein et al. | |
| 6,428,780 B2 | 8/2002 | Leone-Bay et al. | |
| 6,440,929 B1 | 8/2002 | Milstein et al. | |
| 6,458,383 B2 * | 10/2002 | Chen et al. | 424/451 |
| 6,461,545 B1 | 10/2002 | Kantor | |
| 6,461,643 B2 | 10/2002 | Milstein et al. | |
| 6,525,020 B2 | 2/2003 | Leone-Bay et al. | |
| 6,558,706 B2 | 5/2003 | Kantor et al. | |
| 6,605,298 B1 | 8/2003 | Leigh et al. | |
| 6,610,329 B2 | 8/2003 | Santiago et al. | |
| 6,623,731 B2 | 9/2003 | Leone-Bay et al. | |
| 6,627,228 B1 | 9/2003 | Milstein et al. | |
| 6,642,411 B1 | 11/2003 | Leone-Bay et al. | |
| 6,646,162 B2 | 11/2003 | Tang et al. | |
| 6,663,887 B2 | 12/2003 | Leone-Bay et al. | |
| 6,663,898 B2 | 12/2003 | Milstein | |
| 6,693,073 B2 | 2/2004 | Milstein et al. | |
| 6,693,208 B2 | 2/2004 | Gscheidner et al. | |
| 6,699,467 B2 | 3/2004 | Leone-Bay et al. | |
| 6,846,844 B2 | 1/2005 | Tang | |
| 2001/0003001 A1 | 6/2001 | Leone-Bay et al. | |
| 2001/0024658 A1 | 9/2001 | Chen et al. | |
| 2001/0039258 A1 | 11/2001 | Milstein et al. | |
| 2002/0001591 A1 | 1/2002 | Santiago et al. | |
| 2002/0013497 A1 | 1/2002 | Gschneidner et al. | |
| 2002/0028250 A1 | 3/2002 | Milstein | |
| 2002/0040061 A1 | 4/2002 | Tang et al. | |
| 2002/0052422 A1 | 5/2002 | Milstein et al. | |
| 2002/0065255 A1 | 5/2002 | Bay et al. | |
| 2002/0102286 A1 | 8/2002 | Kantor et al. | |
| 2002/0119910 A1 | 8/2002 | Leone-Bay et al. | |
| 2002/0120009 A1 | 8/2002 | Leone-Bay et al. | |
| 2002/0127202 A1 | 9/2002 | Leone-Bay et al. | |
| 2002/0155993 A1 | 10/2002 | Milstein | |
| 2003/0008900 A1 | 1/2003 | Leone-Bay et al. | |
| 2003/0012817 A1 | 1/2003 | Milstein et al. | |
| 2003/0045579 A1 | 3/2003 | Leone-Bay et al. | |
| 2003/0072740 A1 | 4/2003 | Milstein et al. | |
| 2003/0077303 A1 | 4/2003 | Holmberg et al. | |
| 2003/0078302 A1 | 4/2003 | Leone-Bay et al. | |
| 2003/0133953 A1 | 7/2003 | Milstein et al. | |
| 2003/0198658 A1 | 10/2003 | Milstein | |

(Continued)

FOREIGN PATENT DOCUMENTS

WO    WO-96/30036    10/1996

(Continued)

*Primary Examiner* — Paul V. Ward
(74) *Attorney, Agent, or Firm* — Blank Rome LLP

(57) ABSTRACT

The present invention relates to a solid pharmaceutical composition (such as a solid dosage form) comprising a delivery agent and wetted heparin. The inclusion of wetted heparin rather than un-wetted heparin in the solid pharmaceutical composition results in increased delivery of the heparin. Without being bound by any particular theory, applicants believe that because the polymer chain of the wetted heparin is already in an "open" form, while un-wetted heparin is not, less of the wetted heparin is broken down in the gastrointestinal tract and is more readily absorbed in the stomach.

105 Claims, 25 Drawing Sheets

U.S. PATENT DOCUMENTS

| | | |
|---|---|---|
| 2003/0225300 A1 | 12/2003 | Leone-Bay et al. |
| 2003/0232085 A1 | 12/2003 | Milstein et al. |
| 2003/0235612 A1 | 12/2003 | Leone-Bay et al. |
| 2004/0022856 A1 | 2/2004 | Sarubbi et al. |
| 2004/0062773 A1 | 4/2004 | Santiago et al. |
| 2004/0068013 A1 | 4/2004 | Leone-Bay et al. |
| 2004/0106825 A1 | 6/2004 | Bay et al. |
| 2004/0110839 A1 | 6/2004 | Leone-Bay et al. |
| 2005/0009748 A1 | 1/2005 | Dinh et al. |

FOREIGN PATENT DOCUMENTS

| | | |
|---|---|---|
| WO | WO-00/07979 | 2/2000 |
| WO | WO-00/40203 | 7/2000 |
| WO | WO-00/47188 | 8/2000 |
| WO | WO-00/50386 | 8/2000 |
| WO | WO-00/59863 | 10/2000 |
| WO | WO-01/32130 | 5/2001 |
| WO | WO-01/32596 | 5/2001 |
| WO | WO-01/34114 | 5/2001 |
| WO | WO-01/44199 | 6/2001 |
| WO | WO-01/51454 | 7/2001 |
| WO | WO-01/70219 | 9/2001 |
| WO | WO-01/92206 | 12/2001 |
| WO | WO-02/02509 | 1/2002 |
| WO | WO-02/15959 | 2/2002 |
| WO | WO-02/16309 | 2/2002 |
| WO | WO-02/19969 | 3/2002 |
| WO | WO-02/20466 | 3/2002 |
| WO | WO-02/069937 | 9/2002 |
| WO | WO-02/070438 | 9/2002 |
| WO | WO-02/100338 | 12/2002 |
| WO | WO-03/026582 | 4/2003 |
| WO | WO-03/045306 | 6/2003 |
| WO | WO-03/045331 | 6/2003 |
| WO | WO-03/057170 | 7/2003 |
| WO | WO-03/057650 | 7/2003 |
| WO | WO-2004/062587 | 7/2004 |
| WO | WO-2004/080401 | 9/2004 |
| WO | WO-2004/104018 | 12/2004 |
| WO | WO-2005/020925 | 3/2005 |

* cited by examiner

SOLID DOSAGE FORM OF WETTED HEPARIN

This application is a 371 National Phase of International Application No. PCT/US2005/016012, filed May 6, 2005, which claims priority under 35 U.S.C. §119 to U.S. Provisional Application No. 60/569,475, filed May 6, 2004, U.S. Provisional Application No. 60/572,679, filed May 19, 2004, and U.S. Provisional Application No. 60/598,978, filed Aug. 4, 2004, all of which are hereby incorporated by reference.

FIELD OF THE INVENTION

The present invention relates to a solid dosage form of wetted heparin and a delivery agent.

BACKGROUND OF THE INVENTION

Heparin is the most widely used anticoagulant for the prevention and initial treatment of venous thromboembolism, which includes deep vein thrombosis (DVT) and pulmonary embolism (PE). PE is estimated to result in more than 300,000 hospital admissions per year and is responsible for approximately 50,000 to 250,000 deaths annually in the United States alone. There are numerous indications approved and unapproved that involve use of heparin products, both fractionated and unfractionated. Usually, the goal of the therapy is to treat or prevent a thrombotic event.

Heparin is a potent anticoagulant whose chemical composition includes a mixture of repeating disaccharide units, composed of glucosamine and either L-iduronic or D-glucuronic acid. Heparin is a naturally occurring glycosaminoglycan most frequently isolated commercially from cow lung and porcine intestinal mucosa. It is sulfated, anionic, and highly acidic.

Heparin inhibits reactions that lead to the clotting of blood and the formation of fibrin clots also known as thrombus. It inhibits several activated coagulation factors, in particular, factor Xa and factor IIa, by binding to the plasma protease inhibitor antithrombin III. It is partially metabolized by desulphation and depolymerization.

Heparin includes both unfractionated and low-molecular-weight heparin, e.g., dalteparin sodium, enoxaparin, tinzaparin. Heparins are indicated for prophylaxis of ischemic complications in unstable angina and non-Q-wave mycordial infarction, prophylaxis of deep vein thrombosis (DVT) in patients following hip or knee replacement surgery, and prophylaxis of DVT in patients following abdominal surgery in patients at risk for thromboembolic complications. Abdominal surgery patients at risk include those who are over 40 years of age, obese, undergoing surgery under general anesthesia lasting longer than 30 minutes or who have additional risk factors such as malignancy or a history of DVT or pulmonary embolism. Heparins are also indicated for prophylaxis of DVT in medical patients with severely restricted mobility during acute illness, and treatment of DVT with or without pulmonary embolism.

The anticoagulant effect of heparin requires the presence of antithrombin III to facilitate the formation of a 1:1 complex with thrombin. The rate of thrombin-antithrombin III complex formation is increased 1,000-fold by heparin which serves as a catalytic template to which both the inhibitor and thrombin bind. Binding of heparin also induces a conformational change in antithrombin, making the reactive site more accessible to thrombin. Antithrombin binds to heparin via sulfate groups on a specific pentasaccharide sequence found in about 30% of heparin molecules. The heparin-antithrombin III complex can also inhibit activated Factors IX, X, XI, and XII. Once thrombin binds to antithrombin, the heparin molecule is released from the complex. When, for example, the concentration of heparin in plasma is about 0.1 to 1.0 IU/mL, thrombin, Factor IIa, and Factor Xa are rapidly inhibited by antithrombin III. The result is an increase in blood coagulation time, as measured by activated partial thromboplastin time (aPTT), thrombin time, anti-Factor IIa, and anti-Factor Xa activity.

Presently, heparin is administered parenterally, either by continuous or intermittent intravenous infusion or by deep subcutaneous injection. Heparin alone is not well absorbed through the gastrointestinal tract.

U.S. Pat. No. 6,458,383 discloses a delayed release pharmaceutical dosage form for oral administration of a hydrophilic drug. The dosage form comprises low molecular weight heparin, a bile salt or bile acid, and at least one surfactant selected from hydrophilic surfactant, a lipophilic surfactant, and mixtures thereof.

There remains a need for heparin pharmaceutical compositions that can be administered orally and provide an increased heparin response, i.e., an oral heparin administration that can traverse the gastrointestinal tract and provide increased bioavailability. Such a composition would provide a more convenient dosage method for patients receiving heparin. Oral heparin would also increase patient compliance, particularly for patients requiring prophylactic therapy to prevent major venous thromboembolic events. The fact that injections and needles are not required is appealing to patients and can reduce infections due to the disruption of the integrity of the skin by injections.

SUMMARY OF THE INVENTION

The present invention relates to a solid pharmaceutical composition comprising a delivery agent and wetted heparin. The inclusion of wetted heparin rather than un-wetted heparin in the solid pharmaceutical composition results in increased delivery of the heparin. Without being bound by any particular theory, applicants believe that because the polymer chain of the wetted heparin is already in an "open" form, while un-wetted heparin is not, less of the wetted heparin is broken down in the gastrointestinal tract and is more readily absorbed in the stomach. The solid pharmaceutical composition may be a unit dosage form, such as a tablet, capsule, orally disintegrating tabs and strips, granules, powder packets, and patches.

According to one preferred embodiment, the solid pharmaceutical composition comprises (i) a delivery agent selected from N-[8-(2-hydroxybenzoyl)-amino]caprylic acid and pharmaceutically acceptable salts thereof (such as its monosodium salt) (collectively hereafter referred to as "SNAC"), and (ii) wetted heparin. The wetted heparin comprises heparin and a solvent. Preferably, the solvent also partially solubilizes the SNAC. The un-solubilized SNAC has been found to act as a good gelling agent for gelling the SNAC and wetted heparin together. The solid pharmaceutical compositions facilitates the oral delivery of heparin, with increased bioavailability compared to the administration of tablets containing an equivalent amount of un-wetted heparin and SNAC.

Yet another embodiment of the invention is a method for administering or facilitating the delivery of heparin in a subject in need thereof by orally administering the solid pharmaceutical composition of the present invention.

Yet another embodiment is a method of treating or preventing thrombosis in a subject in need thereof by orally administering an anti-thrombosis effective amount of the solid pharmaceutical composition of the present invention. Any type of thrombosis can be treated or prevented with the pharmaceutical composition including, but not limited to, deep vein thrombosis (DVT) and pulmonary embolism (PE).

Yet another embodiment is a method of preventing a major venous thromboembolic event in a subject in need thereof by orally administering an anti-thrombosis effective amount of the solid pharmaceutical composition of the present invention. Such patients include those who recently (e.g., within about a week or two) underwent hip or knee replacement or abdominal surgery, especially those who are over 40 years of age, or obese, or underwent surgery under general anesthesia lasting longer than 30 minutes, or have additional risk factors, such as malignancy or a history of DVT or PE.

Yet another embodiment is a method of preparing a solid pharmaceutical composition of the present invention by mixing a delivery agent, heparin, and wetting agent to form a semi solid or gel composition. For example, a blend of delivery agent and heparin can be added to a wetting agent solution (individually or collectively) to form a semi-solid or gel composition. The solid pharmaceutical composition may further be formulated into a unit dosage form, such as by packing the composition into a capsule.

Yet another embodiment is a solid pharmaceutical composition comprising a delivery agent (e.g., SNAC), and wetted heparin, wherein:
(1) about 120 minutes after oral administration of the solid pharmaceutical composition to a human, the human exhibits a plasma aPTT, an anti-factor IIa plasma concentration, an anti-factor Xa plasma concentration, or any combination of the foregoing that are statistically significantly greater than that about 120 minutes after oral administration of an identical composition containing unwetted heparin instead of wetted heparin,
(2) after oral administration of the solid pharmaceutical composition to a human, the human exhibits an Emax for aPTT, EAUC(0-inf) for aPTT, Emax for anti-factor IIa, EAUC(0-inf) for anti-factor IIa, Emax for anti-factor Xa, EAUC(0-inf) for anti-factor Xa, or any combination of the foregoing that are statistically significantly greater than after oral administration of an identical composition containing unwetted heparin instead of wetted heparin, or
(3) both.

Yet another embodiment is a solid pharmaceutical composition comprising SNAC and wetted heparin, wherein:
(1) about 120 minutes after oral administration of the solid pharmaceutical composition to a human, the human exhibits one or more of the following:
  (i) a plasma aPTT of at least about 38 seconds,
  (ii) an anti-factor IIa plasma concentration of at least about 0.11 IU/ml, or
  (iii) an anti-factor Xa plasma concentration of at least about 0.1 IU/ml,
(2) after oral administration of the solid pharmaceutical composition to a human, the human exhibits one or more of the following:
  (i) an Emax for aPTT of at least about 50 IU/ml,
  (ii) an EAUC(0-inf) for aPTT of at least about 80 IU*hr/ml,
  (iii) an Emax for anti-factor IIa of at least about 0.35 IU/ml,
  (iv) an EAUC(0-inf) for anti-factor IIa of at least about 0.7 IU*hr/ml,
  (v) an Emax for anti-factor Xa of at least about 0.35 IU/ml,
  (vi) an EAUC(0-inf) for anti-factor Xa of at least about 0.68 IU*hr/ml, or
(3) both.

Preferably, about 120 minutes after administration, the human exhibits (i) a plasma aPTT of at least about 39 or about 50 seconds, (ii) an anti-factor IIa plasma concentration of at least about 0.2 IU/ml, (iii) an anti-factor Xa plasma concentration of at least about 0.2 IU/ml, or any combination thereof. Preferably, after administration, the human exhibits (i) an EAUC(0-inf) for aPTT of at least about 100, 150, or 180 IU*hr/ml, (ii) Emax for anti-factor IIa of at least about 0.4 IU/ml, (iii) an EAUC(0-inf) for anti-factor IIa of at least about 1.0 IU*hr/ml, (iv) an Emax for anti-factor Xa of at least about 0.4 IU/ml, (v) an EAUC(0-inf) for anti-factor Xa of at least about 1.0 IU*hr/ml, of any combination thereof.

Yet another embodiment is a method of treating or preventing DVT in a human in need thereof by orally administering one or more solid pharmaceutical compositions comprising SNAC and wetted heparin, wherein
(1) about 120 minutes after oral administration of the solid pharmaceutical composition to a human, the human exhibits one or more of the following:
  (i) a plasma aPTT of at least 38 seconds,
  (ii) an anti-factor IIa plasma concentration of at least about 0.11 IU/ml, or
  (iii) an anti-factor Xa plasma concentration of at least about 0.1 IU/ml,
(2) after oral administration of the solid pharmaceutical composition to a human, the human exhibits one or more of the following:
  (i) an Emax for aPTT of at least about 50 IU/ml,
  (ii) an EAUC(0-inf) for aPTT of at least about 80 IU*hr/ml,
  (iii) an Emax for anti-factor IIa of at least about 0.35 IU/ml,
  (iv) an EAUC(0-inf) for anti-factor IIa of at least about 0.7 IU*hr/ml,
  (v) an Emax for anti-factor Xa of at least about 0.35 IU/ml,
  (vi) an EAUC(0-inf) for anti-factor Xa of at least about 0.68 IU*hr/ml, or
(3) both.

Preferably, about 120 minutes after administration, the human exhibits (i) a plasma aPTT of at least about 39 or 50 seconds, (ii) an anti-factor IIa plasma concentration of at least about 0.2 IU/ml, (iii) an anti-factor Xa plasma concentration of at least about 0.2 IU/ml, or any combination thereof. Preferably, after administration, the human exhibits (i) an EAUC(0-inf) for aPTT of at least about 100, 150, or 180 IU*hr/ml, (ii) Emax for anti-factor IIa of at least about 0.4 IU/ml, (iii) an EAUC(0-inf) for anti-factor IIa of at least about 1.0 IU*hr/ml, (iv) an Emax for anti-factor Xa of at least about 0.4 IU/ml, (v) an EAUC(0-inf) for anti-factor Xa of at least about 1.0 IU*hr/ml, of any combination thereof.

Yet another embodiment of the present invention is a solid heparin pharmaceutical composition comprising a delivery agent and wetted heparin, where, upon oral administration of the composition after 15 days of storage at ambient conditions, the maximum Antifactor Xa concentration achieved is at least 66% or 75% of that achieved with the composition before storage.

The present invention also relates to a solid pharmaceutical composition comprising a delivery agent and wetted heparin, wherein the un-wetted heparin has a particle size of less than about 180 microns, or less than about 120 microns, or less than about 80 microns. Also provided is a method of preparing a solid pharmaceutical composition comprising mixing heparin having an average particle size of less about 180 microns, or less than about 120 microns, or less than about 80 microns, a wetting agent, and a delivery agent.

The present invention also relates to a solid pharmaceutical composition comprising a delivery agent and wetted heparin in a suspension, wherein the average particle size of particles the suspension is less than about 180 microns, or less than about 120 microns, or less than about 80 microns. Also provided is a method of preparing a solid pharmaceutical composition comprising mixing wetted heparin and a delivery agent to form a suspension in a solvent, and milling the suspension to provide a suspension with an average particle size of less than about 180 microns, or less than about 120 microns, or less than about 80 microns.

DETAILED DESCRIPTION OF THE INVENTION

Definitions

Figure 1:
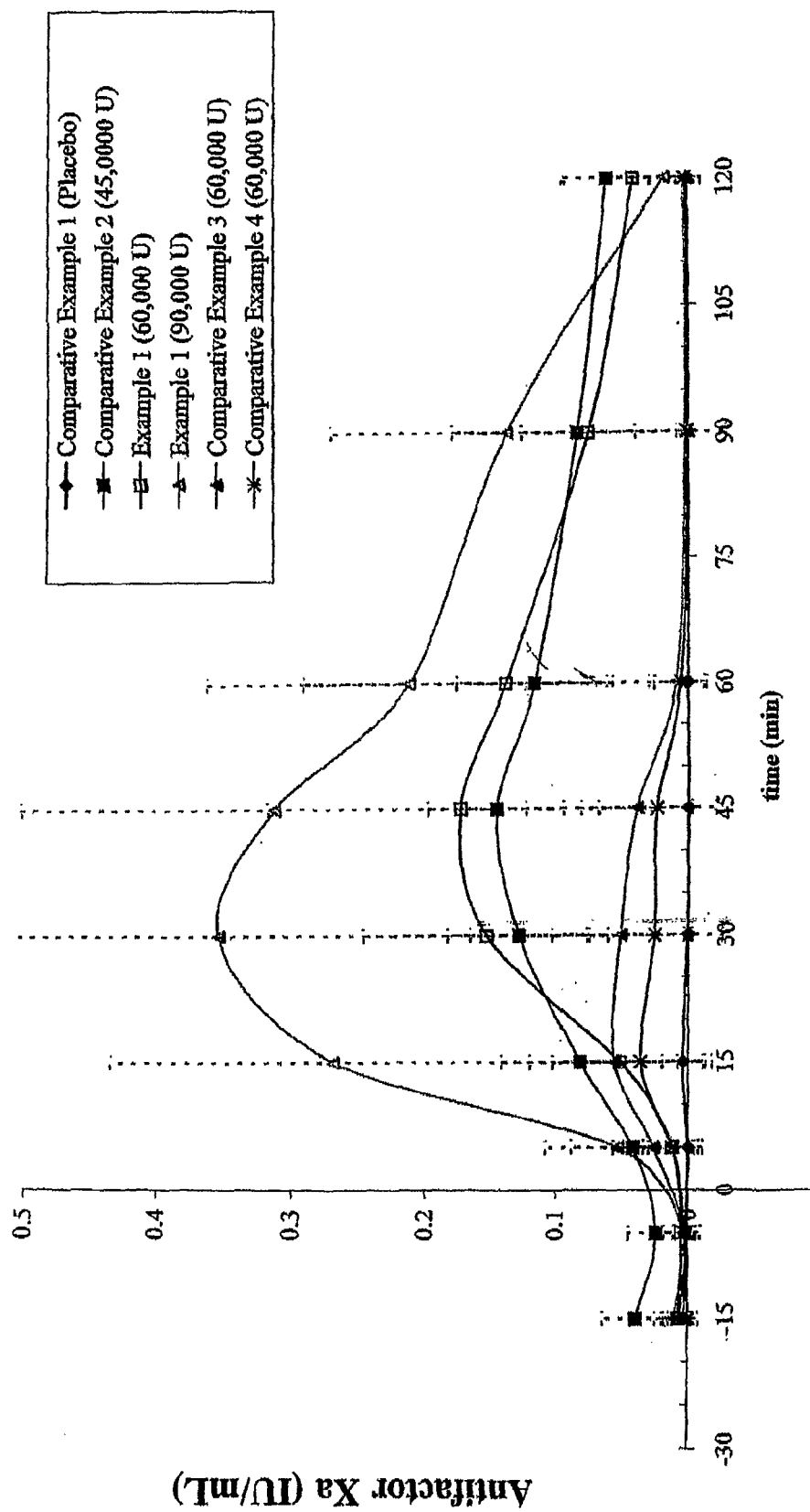
FIG. 1 is a graph of Anti-Factor Xa activity (IU/ml) versus time after administration of each of the pharmaceutical compositions of Example 1 and Comparative Examples 1-4.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, and reference to "the method" includes reference to equivalent steps and methods known to those of ordinary skill in the art that could be modified or substituted for the methods described herein.

The term "wetted heparin" as used herein refers to a form of heparin where the individual heparin particles or molecules are completely or partially surrounded by a solvent or mixture of solvents (also referred to as a "wetting agent"). The heparin may or may not be dissolved in the wetting agent. Without being bound by any particular theory, it is believed that the wetting agent remains within the interstices of the heparin polymer chain in wetted heparin (without necessarily dissolving the heparin) and thereby results in faster dissolution of the heparin upon administration. Preferably, the delivery agent is in intimate contact with the wetted heparin in the solid pharmaceutical composition.

The term "heparin" as used herein refers to all forms of heparin, including, but not limited to, unfractionated heparin, heparinoids, dermatans, chondroitins, low molecular weight heparin (e.g., tinzaparin (including tinzaparin sodium)), very low molecular weight heparin, and ultra low molecular weight heparin. Non-limiting examples include unfractionated heparin, such as heparin sodium (e.g., heparin sodium USP, available from Scientific Protein Labs of Waunakee, Wis.). Heparin generally has a molecular weight of from about 1,000 or 5,000 to about 30,000 Daltons. The term "low molecular weight heparin" generally refers to heparin in which at least about 80% (by weight) of the heparin and has a molecular weight of between about 3000 and about 9000 daltons. Non-limiting examples of low molecular weight heparin include tinzaparin, enoxaprin, and daltiparin. Tinzaparin has been approved by the U.S. Food & Drug Administration for the treatment of acute symptomatic deep vein thrombosis with or without pulmonary embolism when administered in conjunction with warfarin sodium. The sodium salt of tinazaparin is available under the trademark Innohep™ from Pharmion Corporation of Boulder, Colo. The term "very low molecular weight heparin" generally refers to heparin in which at least about 80% (by weight) of the heparin has a molecular weight of between about 1500 and about 5000 daltons. A non-limiting example of very low molecular weight heparin is bemiparin. The term "ultra low molecular weight heparin" generally refers to heparin in which at least about 80% (by weight) of the heparin has a molecular weight of between about 1000 and about 2000 daltons. A non-limiting examples of ultra low molecular weight heparin is fondiparinux.

The term "polymorph" refers to a crystallographically distinct form of a substance.

The term "hydrate" as used herein includes, but is not limited to, (i) a substance containing water combined in the molecular form and (ii) a crystalline substance containing one or more molecules of water of crystallization or a crystalline material containing free water.

Unless otherwise specified, the term "SNAC" as used herein refers to N-(8-[2-hydroxybenzoyl]-amino) caprylic acid and pharmaceutically acceptable salts thereof, including its monosodium salt. The term "SNAC free acid" refers to N-(8-[2-hydroxybenzoyl]-amino)caprylic acid. Unless otherwise noted, the term "SNAC" refers to all forms of SNAC, including all amorphous and polymorphic forms of SNAC, such as those described in U.S. Provisional Application No. 60/569,476 filed May 6, 2004 and U.S. Provisional Application No. 60/619,418, filed Oct. 15, 2004.

The term "SNAD" as used herein refers to N-(8-[2-hydroxybenzoyl]-amino)decanoic acid and pharmaceutically acceptable salts thereof, including its monosodium salt. Unless otherwise noted, the term "SNAD" refers to all forms of SNAD, including all amorphous and polymorphic forms of SNAD.

The term "SNAC trihydrate" as used herein refers to a crystalline form of monosodium SNAC in which three molecules of water are associated with each molecule of SNAC.

The term "solvate" as used herein includes, but is not limited to, a molecular or ionic complex of molecules or ions of a solvent with molecules or ions of delivery agent.

The term "delivery agent" refers to any of the delivery agent compounds disclosed or incorporated by reference herein, including their pharmaceutically acceptable salts.

An "effective amount of heparin" is an amount of heparin which is effective to treat or prevent a condition in a subject to whom it is administered over some period of time, e.g., provides a therapeutic effect during a desired dosing interval. Effective doses will vary, as recognized by those skilled in the art, depending on excipient usage and the possibility of co-usage with other agents for treating a condition.

An "effective amount of the pharmaceutical composition" is an amount of the pharmaceutical composition described which is effective to treat or prevent a condition in a subject to whom it is administered over some period of time, e.g., provides a therapeutic effect during a desired dosing interval.

The term "treat", "treating", or "treated" refers to prophylactically preventing, curing, healing, alleviating, relieving, altering, remedying, ameliorating, improving, or affecting a condition (e.g., a disease), the symptoms of the condition, or the predisposition toward the condition.

An "effective amount of delivery agent" is an amount of the delivery agent which promotes the absorption of a desired amount of the heparin.

The term "subject" includes mammals, such as rodents, cows, pigs, dogs, cats, primates, and particularly humans.

The term "AUC" as used herein, means area under the plasma concentration-time curve, as calculated by the trapezoidal rule over the complete dosing interval, e.g., 24-hour interval.

The term "mean", when preceding a pharmacokinetic value (e.g., mean Peak), represents the arithmetic mean value of the pharmacokinetic value unless otherwise specified.

As used herein, the term "about" means within 10% of a given value, preferably within 5%, and more preferably within 1% of a given value. Alternatively, the term "about" means that a value can fall within a scientifically acceptable error range for that type of value, which will depend on how qualitative a measurement can be given by the available tools.

"Indication" means the use for which the drug is administered either to prevent or to treat a condition, and may be used interchangeably with "treat", "treated" or "treating".

"Thrombus" refers to a clot, or the tendency to form a clot caused by any one of numerous events in vivo or in vitro.

"Thrombotic Event" and Thromboebolic Complications," refer to the formation of a thrombus.

"Antilipidemic Drugs" means any drug or agent that can lower all forms of serum cholesterol and/or triglycerides.

"A control aPTT value" means the aPTT value in seconds used by those skilled in the art to compare a patient's serum aPTT value to an untreated value.

Delivery Agents

Delivery agents which may be used in the pharmaceutical composition of the present invention include those having the formula:

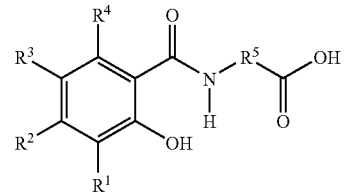

wherein
$R^1$, $R^2$, $R^3$, and $R^4$ are independently hydrogen, —OH, —$NR^6R^7$, halogen, $C_1$-$C_4$ alkyl, or $C_1$-$C_4$ alkoxy;
$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_{12}$ alkylene); and
$R^6$ and $R^7$ are independently hydrogen, oxygen, or $C_1$-$C_4$ alkyl.

The term "substituted" as used herein includes, but is not limited to, substitution with any one or any combination of the following substituents: halogens, hydroxide, $C_1$-$C_4$ alkyl, and $C_1$-$C_4$ alkoxy.

The terms "alkyl", "alkoxy", "alkylene", "alkenylene", "alkyl(arylene)", and "aryl(alkylene)" include, but are not limited to, linear and branched alkyl, alkoxy, alkylene, alkenylene, alkyl(arylene), and aryl(alkylene) groups, respectively.

Preferred delivery agents include, but are not limited to, SNAC, SNAD, 8-(N-2-hydroxy-5-chlorobenzoyl)aminocaprylic acid, 8-(N-2-hydroxy-4-methoxybenzoyl)-aminocaprylic acid, 4-[(4-chloro-2-hydroxybenzoyl)amino]butanoic acid, and pharmaceutically acceptable salts thereof.

Other suitable delivery agents for the present invention are described in U.S. Pat. Nos. 6,846,844, 6,699,467, 6,693,208, 6,693,208, 6,693,073, 6,663,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 5,541,155, 5,693,338, 5,976,569, 5,643,957, 5,955,503, 6,100,298, 5,650,386, 5,866,536, 5,965,121, 5,989,539, 6,001,347, 6,071,510, and 5,820,881. Delivery agents of the present invention are also described in U.S. Patent Application Publication Nos. 20050009748, 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, and 20010003001. Delivery agents of the present invention are also described in International Publication Nos. WO 2005/020925, WO 2004/104018, WO 2004/080401, WO 2004/062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/59863, WO 00/50386, WO 00/47188, WO 00/40203, and WO 96/30036. Each of the above listed U.S. patents and U.S. and International published applications are herein incorporated by reference. These delivery agents may be prepared by methods known in the art, such as those described in the aforementioned patents and published patent applications. For example, SNAC may be prepared by methods known in the art, such as those described in U.S. Pat. Nos. 5,650,386 and 5,866,536, and U.S. Patent Application Publication No. 2002/0065255.

The delivery agent may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed (i) on a suitable chromatographic support such as alumina, using methanol/n-propanol mixtures as the mobile phase, (ii) by reverse phase chromatography using trifluoroacetic acid/acetonitrile mixtures as the mobile phase, or (iii) by ion exchange chromatography using water or an appropriate buffer as the mobile phase. When anion exchange chromatography is performed, preferably a 0-500 mM sodium chloride gradient is employed.

Furthermore, the delivery agents of the present invention may be in a salt form. Non-limiting examples of pharmaceutically acceptable salts include sodium, hydrochloric acid, sulfuric acid, phosphoric acid, citric acid, acetic acid, sulfate, phosphate, chloride, bromide, iodide, acetate, propionate, hydrobromic acid, sodium hydroxide, potassium hydroxide, ammonium hydroxide, and potassium carbonate. These salts can be prepared by methods known in the art. For example, sodium salts may be prepared by dissolving the delivery agent in ethanol and adding aqueous sodium hydroxide.

The amount of delivery agent in the solid pharmaceutical composition is a delivery agent effective amount and can be determined for the particular heparin composition by methods known to those skilled in the art.

According to one embodiment of the invention, the pharmaceutical composition includes from about 50 to about 500 mg of SNAC. According to another embodiment, the pharmaceutical composition includes from about 215 to about 245 mg of SNAC.

The ratio of delivery agent to heparin (mg to USP heparin units) in the pharmaceutical composition generally ranges from about 1:20 to about 1:400. According to a preferred embodiment, the ratio ranges from about 1:65 to about 1:150.

The weight ratio of heparin to delivery agent in the pharmaceutical composition generally ranges from about 1:1 to about 1:10. According to a preferred embodiment, the weight ratio ranges from about 1:1 or 1:2.5 to about 1:5 or about 1:7.5, or about 1:2.5 to about 1:10, or about 1:5 to about 1:10 heparin:delivery agent.

Heparin

The pharmaceutical composition can include a therapeutic effective amount of heparin. Alternatively, the amount can be less than a therapeutic amount when (i) a dosage form containing a plurality of pharmaceutical compositions is used, or (ii) a plurality of the pharmaceutical compositions are intended to be administered concurrently and, in total, contain a therapeutic effective amount.

The total amount of heparin to be used can be determined by methods known to those skilled in the art. However, because the compositions of the invention may deliver heparin more efficiently than other compositions or compositions containing the heparin alone, lower amounts of heparin than those used in prior dosage unit forms or delivery systems can be administered to the subject, while still achieving the same blood levels and/or therapeutic effects.

According to one embodiment of the invention, the pharmaceutical composition includes from about 10 to about 500 mg of heparin. According to another embodiment, the pharmaceutical composition includes from about 100 to about 115 mg of heparin. According to yet another embodiment, the pharmaceutical composition includes from about 2,000 to about 50,000 USP heparin units. According to yet another embodiment, the pharmaceutical composition includes from about 10,000 to about 20,000 USP heparin units. According to yet another embodiment, the pharmaceutical composition includes from about 12,000 to about 18,000 USP heparin units.

A preferred type of heparin is unfractionated heparin.

Wetting Agent

The wetting agent can be a liquid which solubilizes the heparin and is present within the interstices of the polymer chain of the heparin. Because such a wetting agent solubilizes the heparin, it is also a solvent in the pharmaceutical composition. According to one preferred embodiment, the pharmaceutical composition includes a sufficient amount of wetting agent to partially solubilize the delivery agent. According to another embodiment, the wetting agent and the solvent or solubilizer may be different agents, or they may be the same.

Suitable wetting agents include, but are not limited to, alcohols, polyols, hydroxylated fatty acid esters (i.e., fatty acid esters having one or more hydroxy groups), and non-hydroxylated fatty acid esters (i.e., fatty acid esters that do not have hydroxy groups). Non-limiting examples of suitable solvents include ethanol, ethylene glycol, propylene glycol, glycerol, pentaerythritol, sorbitol, mannitol, transcutol, dimethyl isosorbide, polypropylene glycol, polyvinylalcohol, hydroxypropyl methylcellulose and other cellulose derivatives, cyclodextrins and cyclodextrin derivatives, PEG-40 hydrogenated castor oil (available as Cremophor® RH 40 from BASF Ag of Ludwigshafen, Germany), medium chain ($C_8$-$C_{10}$ fatty acids) triglycerides (available as Labrafac® CC from Gattefossé Corporation of Paramus, N.J.), oleoyl macrogol-6 glycerides (Labrafil®1944 CS available from Gattefossé Corporation), linoleoyl macrogol-6 glycerides (Labrafil® M 2125 CS available from Gattefossé Corporation), propylene glycol monolaurate (Lauroglycol® 90 available from Gattefossé Corporation), caprylic/capric glycerides (Imwitor® 742 available from Sasol Germany GmbH of Witten, Germany), glyceryl cocoate (Imwitor® 928 available from Sasol Germany GmbH), glyceryl caprylate (Imwitor® 988 available from Sasol Germany GmbH), propylene glycol dicaprylate/dicaprate (Miglyol® 840 from Condea Vista Co. of Cranford, N.J.), glyceryl ricinoleate (Softigen® 701 available from Sasol Germany GmbH), PEG-6 caprylic/capric glycerides (Softigen® 767 available from Sasol Germany GmbH), bis-diglycerylpolyacyladipate (Softigene® 645 available from Sasol Germany GmbH), PEG-25 trioleate (Tagat® TO available from Goldschmidt Chemical Corp, Hopewell, Va.), polysorbate 80 (Tween 80), ethers of polyethylene glycols having an average molecular weight of about 200 to about 6000 (such as tetrahydrofurfuryl alcohol PEG ether (glycofurol (BASF of Ludwigshafen, Germany, under the trademark Tetraglycol™)) or methoxy PEG (Union Carbide of Midland, Mich.)), amides and other nitrogen-containing compounds (such as 2-pyrrolidone, 2-piperidone, Σ-caprolactam, N-alkylpyrrolidone, N-hydroxyalkylpyrrolidone, N-alkylpiperidone, N-alkylcaprolactam, dimethylacetamide and polyvinyl-pyrrolidone), esters (such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, Σ-caprolactone and isomers thereof, Δ-valerolactone and isomers thereof, and β-butyrolactone and isomers thereof), other solubilizers known in the art (such as dimethyl acetamide, dimethyl isosorbide, N-methylpyrrolidones, monooctanoin, and diethylene glycol monoethyl ether), and mixtures thereof. Other suitable wetting agents are referred to as solubilizers in U.S. Pat. No. 6,458,383, which is hereby incorporated by reference.

Preferred wetting agents include, but are not limited to, polyethylene glycol having a molecular weight less than about 800 daltons (e.g., polyethylene glycol-300), propylene glycol monocaprylate (such as Capmul® PG8 (fatty acid distribution by GLC: <1.0% $C_6$, >98.0% $C_8$, <2.0% $C_{10}$, and <1.0% $C_{12}$ and higher) from Abitec Corporation of Columbus, Ohio; and Capryol 90 (containing 90% monoesters) from Gattefosse Corp., Paramus, N.J.), and mixtures thereof. When capsules which dissolve upon contact with water are used, the pharmaceutical composition within the capsule preferably is substantially free of water (e.g., includes less than about 8, about 5, or about 1% by weight of water (based on 100% total weight of pharmaceutical composition)) or is free of water.

According to one embodiment, the pharmaceutical composition includes polyethylene glycol-300.

According to another embodiment, the pharmaceutical composition includes a mixture of polyethylene glycol-300 and propylene glycol monocaprylate.

In yet another embodiment, the pharmaceutical composition includes from about 100 to about 500 mg polyethylene glycol-300, and about 20 to about 250 mg of propylene glycol monocaprylate. In yet another embodiment, the pharmaceutical composition includes from about 210 to about 240 mg polyethylene glycol-300 and from about 90 to about 110 mg propylene glycol monocaprylate.

Generally, the ratio of wetting agent to heparin (mg to USP heparin units) in the pharmaceutical composition ranges from about 1:10 to about 1:100. According to a preferred embodiment, the ratio ranges from about 1:25 to about 1:60.

The weight ratio of heparin to delivery agent in the pharmaceutical composition generally ranges from about 1:1 to about 1:10. According to a preferred embodiment, the weight ratio ranges from about 1:1 or 1:2.5 to about 1:5 or about 1:2.5 to about 1:10.

The aforementioned wetting agents may be used in combination with an ancillary wetting agent, such as water, glyceryl caprylate/caprate (available as Capmul® MCM from Abitec Corporation of Columbus, Ohio), polysorbate 20, lauroyl macrogol-32 glyceride (Gelucire® 44/14 available from Gattefosse Corp., Paramus, N.J.), stearoyl macrogol-32 glyceride (Gelucire® 50/13 available from Gattefosse Corp.), caprylic/capric triglyceride (available as Akomed E and Akomed R from Karlshamns AB of Karlshamn, Sweden; as Captex® 355 from Abitec Corporation of Columbus, Ohio; as Miglyol® 810 and 812 from Condea Vista Co. of Cranford, N.J.), and mixtures thereof.

Additional Active Ingredients and Additives

Additional Active Agents

Suitable additional active agents include, but are not limited to, warfarin sodium. Other suitable active ingredients include, but are not limited to, acetylsalicylic acid (ASA or aspirin), or enteric coated ASA, ticlodipine, clopidogrel, pentoxifyline, cilostazol, dipyridamole, ER-dipyridamole, abciximab, cilostazol, eptifibatide, or tirofiban, either individually or in combination. Other suitable active agents include, but are not limited to thrombolytic agents, such as alteplase, reteplase, streptokinase, tenecteplase and urokinase, either alone or in combination. Other suitable active agents include, but are not limited to antilipidemic drugs, including but not limited to the statins such as lovastatin, atorvostatin, and, pravastatin, either individually or in combination. Other biologically active agents and chemically active agents, including, but not limited to, pharmacological agents and therapeutic agents can be added to solid dosage forms of the present invention.

Suitable biologically and chemically active agents include, but are not limited to, proteins; polypeptides; peptides; hormones; polysaccharides, muco-polysaccharides and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastrointestinal mucosa and/or are susceptible to chemical cleavage by acids and enzymes in the gastrointestinal tract; or any combination thereof.

Further examples of suitable biologically active agents include, but are not limited to, the following, including synthetic, natural or recombinant sources thereof: growth hormones, including human growth hormones (hGH), recombinant human growth hormones (rhGH), bovine growth (hGH), bovine growth hormones, and porcine growth hormones; growth hormone-releasing hormones; growth hormone releasing factor (e.g., GRF analog g); interferons, including α, β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as BIBN-4096BS and other calcitonin gene-related proteins antagonists; antimicrobials, including antibiotics (include gram-positive acting, bacteriocidal, lipopeptidal and cyclic peptidal antibiotics, including daptomycin), anti-bacterials and anti-fungal agents; vitamins; analogs, fragments, mimetics or polyethylene glycol (PEG)-modified derivatives of these compounds; or any combination thereof.

Further examples include, but are not limited to, the following, including synthetic, natural or recombinant sources thereof:

Amylin and Amylin Agonists;
Adrenocorticotropin;
Antigens;
Antimicrobials, including Antibiotics, Anti-Bacterials and Anti-Fungal Agents; non-limiting examples of Antibiotics include Gram-Positive Acting, Bacteriocidal, Lipopeptidal and Cyclic Peptidal Antibiotics, such as Daptomycin And Analogs thereof;
Anti-Migraine Agents such as BIBM-4096BS And Other Calcitonin Gene-Related Proteins Antagonists, Sumatriptan Succinate;
Antivirals including Acyclovir, Valacyclovir;
Atrial Naturetic Factor;
Bisphosphonates, including Alendronate, Clodronate, Etidronate, Ibandronate, Incadronate, Minodronate, Neridronate, Olpadronate, Pamidronate, Risedronate, Tiludronate, Zoledronate, EB1053, and YH529;
Calcitonin, including Salmon, Eel, Porcine And Human;
Cholecystokinin (CCK) And CCK Agonists Including CCK-8;
Cromolyn Sodium (Sodium Or Disodium Chromoglycate);
Cyclosporine;
Desferrioxamine (DFO);
Erythropoietin;
Exedin and Exedin Agonists, including Exendin-3, Exendin-4;
Filgrastim
Follicle Stimulating Hormone (recombinant and natural);
Glucagon-Like Peptide 1 (GLP-1), Glucagon, and Glucagon-Like Peptide 2 (GLP-2);
Glucocerebrosidase;
Gonadotropin Releasing Hormone;
Growth Hormone Releasing Factor;
Growth Hormone Releasing Hormones;
Growth Hormones, including Human Growth Hormones (hGH), Recombinant Human Growth Hormones (rhGH), Bovine Growth Hormones, And Porcine Growth Hormones;
Heparinoids, Dermatans, Chondroitins, Low Molecular Weight Heparin, Very Low Molecular Weight Heparin Ultra Low Molecular Weight Heparin and synthetic heparins including Fondiparinux;
Immune Globulins and Immunoglobulins
Insulin, including Porcine, Bovine, Human, And Human Recombinant, Optionally Having Counter Ions Including Zinc, Sodium, Calcium And Ammonium;
Insulin-Like Growth Factor, including IGF-1;
Interferons, Including $\alpha$ (e.g., Interferon Alfacon-1 (Available As Infergen ® From Intermune, Inc. of Brisbane, Ca)), alpha, $\beta$, Omega and $\gamma$;
Interleukin-1; Interleukin-2; Interleukin-11; Interleukin-21;
Leutinizing Hormone and Leutinizing Hormone Releasing Hormone;
Leptin (OB Protein);
Monoclonal Antibodies including Retuxin, TNF-alpha soluble receptors;
Oxytocin;
Parathyroid Hormone (PTH), including its fragments, including PTH 1-34 and PTH 1-38;
Peptide YY (PYY) including PYY Agonists and PYY fragment 3-36;
Prostaglandins;
Protease Inhibitors;
Somatostatin;
Thrombopoietin;
Vancomycin;
Vasopressin;
Vitamins;
Vaccines including those against anthrax, *Y. Pestis*, Influenza, or Herpes;

including secretagogues, analogs, fragments, mimetics or polyethylene glycol (PEG)-modified derivatives of these compounds; or any combination thereof.

The pharmaceutical composition can include a therapeutic effective amount of any of the additional active agent(s). Alternatively, the amount can be less than a therapeutic amount when (i) a dosage form containing a plurality of pharmaceutical compositions is used, or (ii) a plurality of the pharmaceutical compositions are intended to be administered concurrently and, in total, contain a therapeutic effective amount.

The total amount of active agent to be used can be determined by methods known to those skilled in the art. However, because the compositions of the invention may deliver active agents more efficiently than other compositions or compositions containing the active agent alone, lower amounts of the active than those used in prior dosage unit forms or delivery systems can be administered to the subject, while still achieving the same blood levels and/or therapeutic effects.

Additives

The solid pharmaceutical composition and unit dosage form of the present invention may include other active agents and pharmaceutically acceptable additives, such as excipients, carriers, diluents, stabilizers, plasticizers, binders, glidants, disintegrants, bulking agents, lubricants, plasticizers, colorants, film formers, flavoring agents, taste-masking agents, sugars, sweeteners, preservatives, dosing vehicles, surfactants, and any combination of any of the foregoing. Preferably, these additives are pharmaceutically acceptable additives, such as those described in *Remington's, The Science and Practice of Pharmacy*, (Gennaro, A. R., ed., 20th

edition, 2003, Mack Pub. Co.), which is herein incorporated by reference.

In one embodiment of the present invention, the pharmaceutical composition or solid unit dosage unit form is substantially free or completely free of carbomer. According to another embodiment, the pharmaceutical composition or solid dosage form is substantially free or completely free of Carbopol® and/or the carbomer Carbopol® 934P.

Suitable binders include, but are not limited to, starch, gelatin, sugars (such as sucrose, molasses and lactose), dibasic calcium phosphate dihydrate, natural and synthetic gums (such as acacia, sodium alginate, carboxymethyl cellulose, methyl cellulose, polyvinylpyrrolidone, polyethylene glycol, ethylcellulose, and waxes.

Suitable glidants include, but are not limited to, talc and silicon dioxide (silica) (e.g., fumed silica and colloidal silicon dioxide).

Suitable disintegrants include, but are not limited to, starches, sodium starch glycolate, croscarmellose sodium, crospovidone, clays, celluloses (such as purified cellullose, methylcellulose, and sodium carboxymethyl cellulose), alginates, pregelatinized corn starches, and gums (such as agar, guar, locust bean, karaya, pectin and tragacanth gums). A preferred disintegrant is sodium starch glycolate.

Suitable bulking agents include, but are not limited to, starches (such as rice starch), microcrystalline cellulose, lactose (e.g., lactose monohydrate), sucrose, dextrose, mannitol, calcium sulfate, dicalcium sulfate, and tricalcium sulfate.

Suitable lubricants include, but are not limited to, stearic acid, stearates (such as calcium stearate and magnesium stearate), talc, boric acid, sodium benzoate, sodium acetate, sodium fumarate, sodium chloride, polyethylene glycol, hydrogenated cottonseed, and castor oils.

Suitable surfactants include, but are not limited to, sodium lauryl sulfate, hydroxylated soy lecithin, polysorbates, and block copolymers of propylene oxide and ethylene oxide.

Hydrophilic non-ionic surfactants and lipophilic surfactants as described in U.S. Pat. No. 6,458,383, which is hereby incorporated by reference, can be included in the pharmaceutical composition and dosage form. Suitable hydrophilic non-ionic surfactants include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof.

More specifically, hydrophilic surfactants that may be used in the present invention include, but are not limited to, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Lipophilic surfactants include, but are not limited to, fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. For example, the lipophilic surfactant can be one or more glycerol fatty acid esters, propylene glycol fatty acid esters, or a mixture thereof, or one or more hydrophobic transesterification products of a polyol with at least one member of the group consisting of vegetable oils, hydrogenated vegetable oils, and triglycerides.

Among the lipophilic transesterification products, transesterification products of a polyol such as ethylene glycol, glycerol, propylene glycol, and sorbitol can be used. As is known in the art, a large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Alcohols include glycerol, propylene glycol, ethylene glycol, polyethylene glycol, maltol, sorbitol, and pentaerythritol. Among these alcohol-oil transesterified surfactants, hydrophobic surfactants include PEG-5 hydrogenated castor oil, PEG-7 hydrogenated castor oil, PEG-9 hydrogenated castor oil, PEG-6 corn oil (Labrafil® M 2125 CS available from Gattefossé Corporation of Paramus, N.J.), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® M 2735 CS), PEG-8 corn oil (Labrafil® M WL 2609 BS), PEG-20 corn glycerides (Crovol M40), and PEG-20 almond glycerides (Crovol A40).

The pharmaceutical compositions and dosage forms may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

Dosage Forms

The solid pharmaceutical composition of the present invention, which includes wetted heparin and a delivery agent, can be formulated as a solid unit dosage form. The dosage form can be, for example, a tablet, a sachet, or a capsule, such as a hard or soft gelatin capsule. The dosage form can provide immediate, sustained, or controlled release of the delivery agent, heparin, and optionally, additional active agents.

The solid pharmaceutical composition and solid unit dosage form of the present invention can be prepared as follows. A delivery agent in solid form is processed (such as by milling through a 35-mesh screen) to provide a powder having a relatively small and preferably uniform particle size. The delivery agent is then blended with heparin, and optionally a filler and/or wetting agent with, for example, a V-blender or similar device, to provide a powder blend.

Separately, a wetting agent mixture is prepared by mixing a wetting agent, heparin and a delivery agent. The mixture may also, for example, include water. The formulation of the wetting mixture is selected so as to wet the heparin when mixed with the aforementioned powder blend. According to one preferred embodiment, the wetting agent mixture is also formulated so as to partially solubilize the delivery agent when mixed with the powder blend.

The powder blend is added to the wetting agent mixture in small increments under continuous mixing. Mixing is continued for a sufficient time (e.g., 15 minutes) after all of the powder blend has been added to obtain a uniform composition. The resulting composition is typically a semi-solid, gel, or liquid.

The composition may then be formulated into a dosage form, such as a capsule, by methods known in the art. According to one preferred embodiment, the resulting composition is packed into a soft gelatin capsule or hard gelatin capsule (e.g., Size 0 Licap Capsugel Hard Gelatin capsules). Other suitable methods are described in U.S. Pat. Nos. 6,605,298, 6,458, 383, 6,261,601, 5,714,477, and 3,510,561; U.S. Patent Application Publication Nos. 2003/0077303 and 2001/0024658; and International Publication No. WO 88/10117, all of which are incorporated by reference.

Uses

The present invention provides a method for administering or facilitating the delivery of heparin to an animal by administering to a subject the solid pharmaceutical composition of the present invention. The subject is preferably a human. The person is preferably a human in need thereof, or a human who would benefit from the administration of heparin.

Another embodiment is a method of treating or preventing thrombosis in a subject in need thereof by orally administering an anti-thrombosis effective amount of the solid pharmaceutical composition of the present invention to the subject. Any type of thrombosis can be treated or prevented with the pharmaceutical composition including, but not limited to, deep vein thrombosis (DVT) and pulmonary embolism (PE).

Another embodiment is a method of treating or preventing ischemic complications in unstable angina and/or non-Q-wave mycordial infarction in a subject in need thereof by orally administering an anti-thrombosis effective amount of the solid pharmaceutical composition of the present invention to the subject.

Another embodiment is a method of treating or preventing deep vein thrombosis (DVT) in a subject following hip or knee replacement surgery by orally administering an anti-thrombosis effective amount of the solid pharmaceutical composition of the present invention to the subject. Yet, another embodiment is a method of treating or preventing DVT following abdominal surgery in patients at risk for thromboembolic complications by orally administering an anti-thrombosis effective amount of the solid pharmaceutical composition of the present invention to the subject. Abdominal surgery patients at risk include, but are not limited to, those who are over 40 years of age, obese, undergoing surgery under general anesthesia lasting longer than 30 minutes or who have additional risk factors such as malignancy or a history of DVT or pulmonary embolism.

Another embodiment is a method of treating or preventing DVT in a subject with severely restricted mobility by orally administering an anti-thrombosis effective amount of the solid pharmaceutical composition of the present invention to the subject. Further embodiments include, but are not limited to the treatment of cardiac valve replacements, both mechanical and cadaver; treatment of endocarditis; prophylaxis in patients undergoing neurological procedures, such as, but not limited to, resection of malignant brain tumors; prophylaxis in patients with acute spinal cord injury, medical conditions associated with thromboembolism, such as but not limited to, those with ischemic stroke or restricted mobility, cancer, myocardial infarction, cancer, congestive heart failure, or severe pulmonary disease; for secondary prophylaxis of venous thromboembolism during pregnancy, or for primary prophylaxis in pregnant women with inherited causes of thrombophilia (e.g. deficiencies in thrombin III, protein C, protein S, Factor V, Leiden mutation, prothrombin polymorphism, hyperhomocysteinemia); for embolisms associated with atrial fibrillation or those with concurrent prosthetic valves and atrial fibrillation; for cardioversion of atrial fibrillation or atrial flutter; for disseminated intravascular coagulation; to reduce the risk of complications in patents undergoing percutaneous coronary intervention, percutaneous transluminal coronary angioplasty, arthrectomy, coronary or other vessel stent implantation, ischemic cerbrovascular accident, hemodialysis, peripheral vascular interventions, acute myocardial infarction; unstable angina and non-ST-Segment Elevation Myocardial infarction; cerebral thromboembolism; complications of pregnancy, including but not limited to pregnancy loss in women with a history of antiphospholipid antibodies/antiphospholipid syndrome with or without fetal loss, fetal death or fetal miscarriage. Other uses of heparin may be found in *Drug Information*, American Society of Health System Pharmacists, 2005, which is incorporated herein by reference.

According to one embodiment, from about 50,000 to about 90,000 units of heparin (in compositions or dosage forms of the present invention) are administered one to five times daily (e.g., three times daily) to treat thrombosis. According to one preferred embodiment, each composition includes from about 250 mg to about 2.3 g of SNAC.

Yet another embodiment of the present invention is a method for the treatment or prevention of a disease or for achieving a desired physiological effect, such as those listed in the table below, in an animal by administering the pharmaceutical composition of the present invention. The pharmaceutical composition includes the appropriate active agent listed below. Specific indications for active agents can be found in the Physicians' Desk Reference ($58^{th}$ Ed., 2004, Medical Economics Company, Inc., Montvale, N.J.), which is herein incorporated by reference. The active agents in the table below include their analogs, fragments, mimetics, and polyethylene glycol-modified derivatives.

| Active Agent | Non-Limiting Examples of Disease And Physiological Effect |
| --- | --- |
| Amylin and Amylin Agonists; | Obesity |
| Adrenocorticotropin; | High Cholesterol (To Lower Cholesterol) |
| Antigens; | Infection |
| Antimicrobials, including Antibiotics, Anti-Bacterials and Anti-Fungal Agents; non-limiting examples of Antibiotics include Gram-Positive Acting, Bacteriocidal, Lipopeptidal and Cyclic Peptidal Antibiotics, such as Daptomycin And Analogs thereof; | Infection Including Gram-Positive Bacterial Infection |
| Anti-Migraine Agents such as BIBM-4096BS And Other Calcitonin Gene-Related Proteins Antagonists, Sumatriptan Succinate; | Migraines |
| Antivirals including Acyclovir, Valacyclovir; | Viral Infections |
| Atrial Naturetic Factor; | Vasodilation |
| Bisphosphonates, including Alendronate, Clodronate, Etidronate, Ibandronate, Incadronate, Minodronate, Neridronate, Olpadronate, Pamidronate, Risedronate, Tiludronate, Zoledronate, EB1053, and YH529; | Cancer, Atherosclerosis, Osteoporosis And Paget's Disease; Inhibits Osteoclasts |
| Calcitonin, including Salmon, Eel, Porcine And Human; | Osteoporosis; Diseases Of The Bone |
| Cholecystokinin (CCK) And CCK Agonists Including CCK-8; | Obesity |
| Cromolyn Sodium (Sodium Or Disodium Chromoglycate); | Asthma; Allergies |
| Cyclosporine; | Transplant Rejection |
| Desferrioxamine (DFO); | Iron Overload |
| Erythropoietin; | Anemia |
| Exedin and Exedin Agonists, including Exendin-3, Exendin-4; | Diabetes; Obesity |
| Filgrastim | Reduce Infection In Chemotherapy Patients |
| Follicle Stimulating Hormone (recombinant and natural); | Regulate Reproductive Function |
| Glucagon-Like Peptide 1 (GLP-1), Glucagon, and Glucagon-Like Peptide 2 (GLP-2); | Diabetes; Obesity |
| Glucocerebrosidase; | Gaucher Disease (To Metabolize Lipoprotein) |
| Gonadotropin Releasing Hormone; | Ovulatory Disfunction (To Stimulate Ovulation) |
| Growth Hormone Releasing Factor; | Growth Disorders |
| Growth Hormone Releasing Hormones; | Growth Disorders |
| Growth Hormones, Including Human Growth Hormones (hGH), Recombinant Human Growth Hormones (rhGH), Bovine Growth Hormones, And Porcine Growth Hormones; | Growth Disorders |
| Heparin, Including Unfractionated Heparin, Heparinoids, Dermatans, Chondroitins, Low Molecular Weight Heparin, Very Low Molecular Weight Heparin Ultra Low Molecular Weight Heparin and synthetic heparins including Fondiparinux; | Thrombosis; Prevention Of Blood Coagulation |
| Immunoglobulin | Infectious disease, and blood dysplasias, |
| Insulin, Including Porcine, Bovine, Human, And Human Recombinant, Optionally Having Counter Ions Including Zinc, Sodium, Calcium And Ammonium; | Diabetes; Insulin Resistance Syndrome |
| Insulin-Like Growth Factor, Including IGF-1; | Diabetes |
| Interferons, Including α (E.G., Interferon Alfacon-1 (Available As Infergen ® From Intermune, Inc. Of Brisbane, Ca)), alpha, β, omega and γ; | Viral Infection, Including Chronic Cancer And Multiple Sclerosis |
| Interleukin-1; Interleukin-2; Interleukin-11; Interleukin-21; | Viral Infection; Cancer |
| Leutinizing Hormone and Leutinizing Hormone Releasing Hormone; | Regulate Reproductive Function |
| Leptin (OB Protein); | Obesity |
| Monoclonal Antibodies including Retuxin, TNF-alpha soluble receptors; | To Prevent Graft Rejection; Cancer |

-continued

| Active Agent | Non-Limiting Examples of Disease And Physiological Effect |
|---|---|
| Oxytocin; | Labor Dysfunction (To Stimulate Contractions) |
| Parathyroid Hormone (PTH), Including Its Fragments, including PTH 1-34 and PTH 1-38; | Osteoporosis; Diseases Of The Bone |
| Peptide YY (PYY) Including PYY Agonists, Fragment 3-36; | Obesity; Diabetes; Eating Disorders; Insulin Resistance Syndrome |
| Prostaglandins; | Hypertension |
| Protease Inhibitors; | AIDS |
| Somatostatin; | Bleeding Ulcer; Erosive Gastritis |
| Thrombopoietin; | Thrombocytopenia |
| Vancomycin; | Infection And Prophylaxis |
| Vasopressin; | Bed-Wetting; Antidiuretic |
| Vitamins; | Vitamin Deficiencies |
| Vaccines Including Those Against Anthrax Or *Y. Pestis*, Influenza, and Herpes; | Prevent And Minimize Disease |

The following examples illustrate the present invention without limitation. All percentages are by weight unless otherwise specified.

EXAMPLE 1

Preparation of Heparin/SNAC Capsules

The SNAC/heparin formulation in Table 1 below was prepared as follows.

TABLE 1

| Component | Target Amount (mg/capsule) | Acceptable Range (mg/capsule) |
|---|---|---|
| SNAC | 229.59 | 218.0-241.1 |
| Heparin sodium, USP | 107.14 (15,000 USP Heparin Units) | 101.14-112.5 |
| Polyethylene Glycol (PEG) 300 | 226.13 | 214.8-237.4 |
| Sodium Lauryl Sulphate | 6.70 | 6.4-7.0 |
| Propylene glycol monocaprylate (Capmul ® PG8) | 100.44 | 95.4-105.5 |
| Total weight | 670.0 | 635.7-703.5 |

Propylene glycol monocaprylate is available as Capmul® PG8 from Abitec Corporation of Columbus, Ohio.

SNAC was milled using a Quadro Comil™ milling machine available from Quadro Engineering Inc. of Waterloo, Ontario, equipped with a 35-mesh screen equivalent. The milled SNAC and heparin sodium, USP were passed through a 35 mesh screen. Sodium lauryl sulphate was added, and the mixture was blended using a 4-quart V-blender shell for 15 minutes. Polyethylene glycol 300 and propylene glycol monocaprylate were separately mixed in a stainless Kitchen Aid™ mixer for 15 minutes. The SNAC/heparin sodium USP/sodium lauryl sulphate blend was added in small increments to the PEG 300/propylene glycol monocaprylate mixture, and mixing was continued. Mixing was continued for 15 minutes after all of the milled SNAC/heparin sodium USP/sodium lauryl sulphate blend was added.

Size 0 Licap Capsugel-hard gelatin capsules (available from Capsulgel of Morris Plains, N.J.) were manually filled with the resulting formulation.

COMPARATIVE EXAMPLE 1

200 (±3) mg of microcrystalline cellulose were filled into size 0 Capsugel hard gelatin capsules and used as a placebo.

COMPARATIVE EXAMPLE 2

Lyophilized Tinzaparin Tablets

Tablets having the formulation shown in Table 2 were prepared as follows.

SNAC was milled using a Quadro Comill equipped with a 35 mesh screen. Tinzaparin was lyophilized using a VirTis Lyophilizer (available from VirTis of Gardiner, N.Y.) as follows. The tinzaparin was dissolved in purified water to produce a solution with a concentration of about 100 mg/mL. The lyophilizer shelves were pre-cooled to −40° C. The tinzaparin solution was then transferred to 3 trays, each tray having about 1.6 kg of solution. The trays were transferred to the lyophilizer and lyophilized to obtain a dry powder. The dry powder was then assayed for tinzaparin content and used for tablet manufacture.

The tablets were manufactured as follows. The required amounts of lyophilized tinzaparin sodium, USP, SNAC, dibasic calcium phosphate dihydrate, USP and sodium lauryl sulphate were weighed out and charged into a 16 Quart V-blender shell. The materials were blended for 15 minutes. The resulting blend was divided into 3 sublots for granulation. Each sublot was transferred into a 5 L bowl of a Key Instruments KG5 high shear granulator (Key Instruments, Inc. of Englishtown, N.J.) and granulated with water as the granulation fluid. After all three sublots were granulated, the wet granulations were transferred to trays and dried in a vacuum oven at 50° C. at <5.0 Hg (vacuum) until the moisture content was less than 15%. The dried granules were milled using a mill equipped with a 35 mesh screen. The milled granulation was assayed for SNAC and tinzaparin content. Based on the tinzaparin assay of the granulation, calculations for extragranular excipients were made.

The extragranular excipients, dibasic calcium phosphate dehydrate, fumed silica and magnesium stearate, were sieved through a 35 mesh screen and the required amounts weighed out. The milled and dried SNAC/tinzaparin granulation was transferred to an 8 Quart V-blender shell together with the dibasic calcium phosphate dehydrate and fumed silica and blended for 15 minutes. After blend uniformity testing, magnesium stearate was added and blended for 3 minutes. The resulting blend was compressed into tablets using an EK-O single station tablet press (Korsch A G, Berlin, Germany). The target tablet weight was 1100 mg with an acceptable range of 1067-1133 mg while the target tablet thickness was 15 kP with and acceptable range of 10-20 kP.

TABLE 2

| Component | Amount (mg/capsule) |
|---|---|
| SNAC | 693 |
| Lyophilized tinzaparin (15,000 USP Heparin Units) | 160.60* |
| Dibasic calcium phosphate dihydrate | 293.01 |
| Sodium lauryl sulphate | 222.19 |
| Fumed silica | 2.20 |
| Magnesium stearate | 11.00 |

*Based on a potency of 93.4 U/mg.

COMPARATIVE EXAMPLE 3

Unlyophilized Heparin Tablets

Tablets having the formulation shown in Table 3 were prepared by the procedure described in Comparative Example 2, except the heparin was not lyophilized.

TABLE 3

| Component | Amount (mg/capsule) |
|---|---|
| SNAC | 460 |
| Unlyophilized heparin (30,000 USP Heparin Units) | 170.26* |
| Dibasic calcium phosphate dihydrate | 152.95 |
| Sodium lauryl sulphate | 8.0 |
| Fumed silica | 1.6 |
| Magnesium stearate | 8.00 |

COMPARATIVE EXAMPLE 4

Lyophilized Heparin Tablets

Tablets having the formulation shown in Table 4 were prepared by the procedure described in Comparative Example 2.

TABLE 4

| Component | Amount (mg/capsule) |
|---|---|
| SNAC | 460 |
| Lyophilized heparin (30,000 USP Heparin Units) | 170.26 |
| Dibasic calcium phosphate dihydrate | 152.95 |
| Sodium lauryl sulphate | 8.0 |
| Fumed silica | 1.6 |
| Magnesium stearate | 8.00 |

EXAMPLE 2

Data from Formulations of Example 1 and Comparative Examples 1-4

Fifteen human test subjects were administered each of the formulations described in Example 1 and Comparative Examples 1-4 in 6 periods, each separated by a 72-hour washout period. For every period, subjects entered a clinic the evening before the administration to begin an 8-hour fast starting at 10 p.m. The formulation was administered in the morning in a fasted state. Table 5 summarizes the six periods and the formulations administered.

TABLE 5

| Period | Formulation | Number of Unit Dosages (Tablets, Capsules) | Total Amount of Heparin (or tinzaparin) (U) | Total Amount of SNAC (mg) |
|---|---|---|---|---|
| 1 | Comparative Example 1 | 1 | 0 | 0 |
| 2 | Example 1 | 4 | 60,000 | 920 |
| 3 | Comparative Example 2 | 3 | 45,000 | 2079 |
| 4 | Example 1 | 6 | 90,000 | 1380 |
| 5 | Comparative Example 3 | 2 | 60,000 | 920 |
| 6 | Comparative Example 4 (n = 13) | 2 | 60,000 | 920 |

For each period, the anti-Factor Xa and anti-Factor IIa activities were measured from blood samples taken at 15 and 5 minutes before dose, and 5, 15, 30, 45, 60, 90, and 120 minutes after dose. Anti-Factor Xa and anti-Factor IIa activities and aPTT times are indicators of heparin response, and provide a basis to compare the bio-availability of the respective formulations.

The results for the 15 subjects were averaged for each sample period, and are shown in the tables below.

TABLE 6

Anti-Factor Xa Activity (IU/ml)
(Standard Deviation shown in parenthesis)

| Time (minutes) | Period 1 | 2 | 3 | 4 | 5 | 6 |
|---|---|---|---|---|---|---|
| −15 | .003 (0.0046) | .007 (0.0110) | 0.039 (0.024) | .011 (0.014) | .006 (0.012) | 0 (0) |
| −5 | .002 (0.0077) | .005 (0.0136) | .024 (0.021) | .003 (0.008) | .002 (0.006) | .002 (0.008) |
| 5 | 0 (0) | .012 (0.0224) | .042 (0.046) | .053 (0.055) | .026 (0.029) | .012 (0.019) |
| 15 | .004 (0.0155) | .051 (0.0685) | .081 (0.061) | .268 (0.166) | .055 (0.051) | .036 (0.048) |
| 30 | .001 (0.0026) | .153 (0.0930) | .129 (0.054) | .355 (0.189) | .051 (0.053) | .025 (0.050) |
| 45 | 0 (0) | .173 (0.1449) | .145 (0.052) | .313 (0.190) | .039 (0.042) | .023 (0.044) |
| 60 | 0 (0) | .139 (0.1522) | .116 (0.059) | .212 (0.151) | .009 (0.019) | .005 (0.019) |
| 90 | 0 (0) | .075 (0.1041) | .083 (0.044) | .137 (0.132) | .002 (0.006) | 0 (0) |
| 120 | .001 (0.0026) | .041 (0.0508) | .061 (0.033) | .018 (0.022) | .003 (0.007) | .002 (0.006) |

TABLE 7

Plasma anti-Factor Xa Pharmacodynamic Parameters

| Period | Emax, IU/ml (CV, %) | TEmax, hr (CV, %) | EAUC (0-last) (CV, %) | EAUC (0-inf) (CV, %) | EMRT, hr (CV, %) |
|---|---|---|---|---|---|
| 1 | 0.01 (160.30) | 0.432 (174) | — | — | — |

TABLE 7-continued

Plasma anti-Factor Xa Pharmacodynamic Parameters

| Period | Emax, IU/ml (CV, %) | TEmax, hr (CV, %) | EAUC (0-last) (CV, %) | EAUC (0-inf) (CV, %) | EMRT, hr (CV, %) |
|---|---|---|---|---|---|
| 2 | 0.20 (69.42) | 0.719 (54.0) | 0.2082 (80.39) | 0.3935 (62.31) | 1.24 (28.1) |
| 3 | 0.16 (33.41) | 0.723 (28.3) | 0.1941 (39.77) | 0.3241 (28.01) | 1.42 (13.4) |
| 4 | 0.36 (50.83) | 0.707 (20.1) | 0.4171 (58.08) | 0.4528 (43.43) | 1.25 (19.2) |
| 5 | 0.07 (70.74) | 0.516 (35.5) | 0.06632 (55.74) | 0.1528 (45.58) | 1.14 (45.3) |
| 6 | 0.05 (93.81) | 0.513 (48.5) | 0.06261 (81.38) | — | — |

TABLE 8

Anti-Factor IIa Activity (IU/ml)

| Time (minutes) | 1 | 2 | 3 | 4 | 5 | 6 |
|---|---|---|---|---|---|---|
| −15 | .089 (0.254) | .025 (0.029) | .039 (0.027) | .035 (0.024) | .024 (0.024) | .015 (0.017) |
| −5 | .026 (0.030) | .025 (0.028) | .062 (0.012) | .045 (0.019) | .028 (0.019) | .023 (0.018) |
| 5 | .034 (0.036) | .029 (0.029) | .058 (0.013) | .074 (0.039) | .039 (0.020) | .027 (0.020) |
| 15 | .030 (0.033) | .058 (0.057) | .067 (0.016) | .304 (0.135) | .073 (0.031) | .041 (0.025) |
| 30 | .033 (0.034) | .137 (0.069) | .079 (0.025) | .383 (0.243) | .074 (0.035) | .038 (0.033) |
| 45 | .032 (0.033) | .160 (0.092) | .088 (0.037) | .382 (0.248) | .055 (0.032) | .035 (0.033) |
| 60 | .027 (0.031) | .140 (0.090) | .071 (0.036) | .248 (0.211) | .042 (0.018) | .021 (0.030) |
| 90 | .024 (0.026) | .107 (0.061) | .083 (0.026) | .165 (0.153) | .048 (0.024) | .018 (0.018) |
| 120 | .024 (0.031) | .069 (0.040) | .077 (0.016) | .044 (0.024) | .039 (0.021) | .009 (0.013) |

TABLE 9

Plasma anti-Factor IIa Pharmacodynamic Parameters

| Period | Emax, IU/ml (CV, %) | TEmax, hr (CV, %) | EAUC (0-last) (CV, %) | EAUC (0-inf) (CV, %) | EMRT, hr (CV, %) |
|---|---|---|---|---|---|
| 1 | 0.05 (66.44) | 0.511 (119) | 0.06896 (80.44) | — | — |
| 2 | 0.18 (50.08) | 0.706 (27.1) | 0.2148 (49.14) | 0.1702 (16.44) | 1.00 (15.5) |
| 3 | 0.11 (24.65) | 1.02 (48.9) | 0.1543 (22.40) | — | — |
| 4 | 0.42 (56.68) | 0.773 (29.1) | 0.5028 (63.54) | 0.4131 (34.23) | 1.18 (12.1) |
| 5 | 0.09 (35.40) | 0.831 (79.8) | 0.1011 (33.74) | — | — |
| 6 | 0.06 (42.54) | 0.612 (44.0) | 0.06181 (60.62) | — | — |

TABLE 10

Ratio of Anti-Factor Xa Activity to Anti-Factor IIa Activity

| Time (minutes) | 1 | 2 | 3 | 4 | 5 | 6 |
|---|---|---|---|---|---|---|
| −15 | 0.03 | 0.30 | 1.00 | 0.30 | 0.25 | 0.00 |
| −5 | 0.08 | 0.18 | 0.39 | 0.06 | 0.07 | 0.10 |
| 5 | 0.00 | 0.41 | 0.72 | 0.72 | 0.67 | 0.43 |
| 15 | 0.13 | 0.89 | 1.21 | 0.88 | 0.75 | 0.89 |
| 30 | 0.02 | 1.12 | 1.64 | 0.93 | 0.69 | 0.66 |
| 45 | 0.00 | 1.08 | 1.65 | 0.82 | 0.70 | 0.67 |
| 60 | 0.00 | 0.99 | 1.63 | 0.85 | 0.21 | 0.26 |
| 90 | 0.00 | 0.70 | 1.00 | 0.83 | 0.04 | 0.00 |
| 120 | 0.03 | 0.60 | 0.79 | 0.41 | 0.08 | 0.25 |

TABLE 11

Plasma SNAC Concentrations (ng/mL)
(Standard Deviation shown in parenthesis)

| Time (minutes) | 1 | 2 | 3 | 4 | 5 | 6 |
|---|---|---|---|---|---|---|
| 0 | NA | 0 (0) | 2.36 (9.15) | 0 (0) | 0 (0) | 0 (0) |
| 5 | NA | 100.44 (276.47) | 1394.87 (1630.58) | 60.19 (67.57) | 812.04 (648.93) | 512.09 (322.79) |
| 15 | NA | 4731.95 (3900.82) | 10139.4 (5481.83) | 4168.13 (2515.09) | 3612.24 (2286.80) | 4339.32 (2010.81) |
| 30 | NA | 4432.24 (2404.94) | 8846.83 (4170.31) | 5973.36 (2913.61) | 2995.23 (1184.70) | 3269.97 (1352.39) |
| 45 | NA | 1747.60 (1062.02) | 4853.39 (3245.89) | 4114.45 (2359.29) | 1399.63 (762.69) | 871.15 (274.51) |
| 60 | NA | 693.87 (352.40) | 2095.89 (1205.31) | 1637.34 (902.59) | 682.07 (282.92) | 513.43 (160.84) |
| 90 | NA | 535.45 (290.47) | 1313.09 (571.42) | 833.55 (400.36) | 416.42 (218.59) | 427.28 (210.71) |
| 120 | NA | 373.32 (273.87) | 1247.41 (861.34) | 726.43 (529.29) | 373.02 (305.72) | 344.04 (432.82) |

TABLE 12

Plasma SNAC Pharmacokinetic Parameters

| Period | Cmax, ng/ml (CV, %) | Tmax, hr (CV, %) | AUC (0-last), ng * hr/ml (CV, %) | AUC (0-inf), ng * hr/ml (CV, %) | $T_{1/2}$, hr (CV, %) | CL/F, L/hr (CV, %) | Vd/F, L (CV, %) |
|---|---|---|---|---|---|---|---|
| 2 | 5907.10 (57.65) | 0.436 (39.9) | 3189.9 (35.630) | 3194.0 (24.783) | 0.522 (54.6) | 301.62 (21.497) | 229.13 (61.386) |
| 3 | 11,874.21 (41.13) | 0.392 (42.4) | 7611.9 (33.044) | 9141.8 (26.432) | 0.618 (54.9) | 239.91 (24.467) | 215.66 (64.28) |
| 4 | 6,969.23 (39.77) | 0.572 (26.1) | 4632.7 (22.895) | 4783.7 (10.429) | 0.444 (39.6) | 291.26 (11.009) | 188.31 (43.187) |
| 5 | 4456.64 (41.28) | 0.348 (42.9) | 2580.5 (30.130) | 2833.4 (25.429) | 0.454 (38.7) | 339.51 (20.392) | 226.25 (45.799) |
| 6 | 4637.60 (40.53) | 0.331 (38.0) | 2685.5 (26.388) | 3016.5 (20.316) | 0.730 (45.2) | 317.07 (21.644) | 326.35 (44.825) |

TABLE 13

Plasma aPTT (seconds)
(Standard Deviation shown in parenthesis)

| Time (minutes) | Period 1 | 2 | 3 | 4 | 5 | 6 |
|---|---|---|---|---|---|---|
| 0 | 26 (2) | 26 (2) | 26 (2) | 26 (2) | 26 (2) | 26 (2) |
| 15 | 26 (2) | 27 (2) | — | — | — | — |
| 30 | 26 (2) | 35 (6) | 31 (4) | 47 (15) | 29 (3) | 29 (3) |
| 45 | 27 (3) | 38 (11) | 31 (4) | 49 (20) | 28 (3) | 28 (3) |
| 60 | 25 (4) | 32 (6) | 30 (3) | 48 (23) | 27 (2) | 27 (2) |
| 120 | 25 (2) | 28 (2) | 28 (2) | 34 (13) | 26 (2) | 27 (2) |
| 480 | 26 (2) | 26 (2) | 26 (2) | 26 (2) | 26 (2) | 26 (2) |

TABLE 14

Plasma aPTT Pharmacokinetic Parameters

| Period | Emax, sec (CV, %) | TEmax, hr (CV, %) | EAUC (0-last) sec * hr (CV, %) |
|---|---|---|---|
| 1 | 27 (11) | 0.305 (127) | 52.795 (9.5374) |
| 2 | 38 (28) | 0.604 (25.6) | 64.372 (17.531) |
| 3 | 32 (13) | 0.583 (17.3) | 58.736 (9.5973) |
| 4 | 54 (41) | 0.771 (49.8) | 82.333 (32.203) |
| 5 | 29 (11) | 0.408 (63.0) | 54.809 (7.924) |
| 6 | 29 (12) | 0.469 (48.6) | 67.017 (12.861) |

Figure 2:
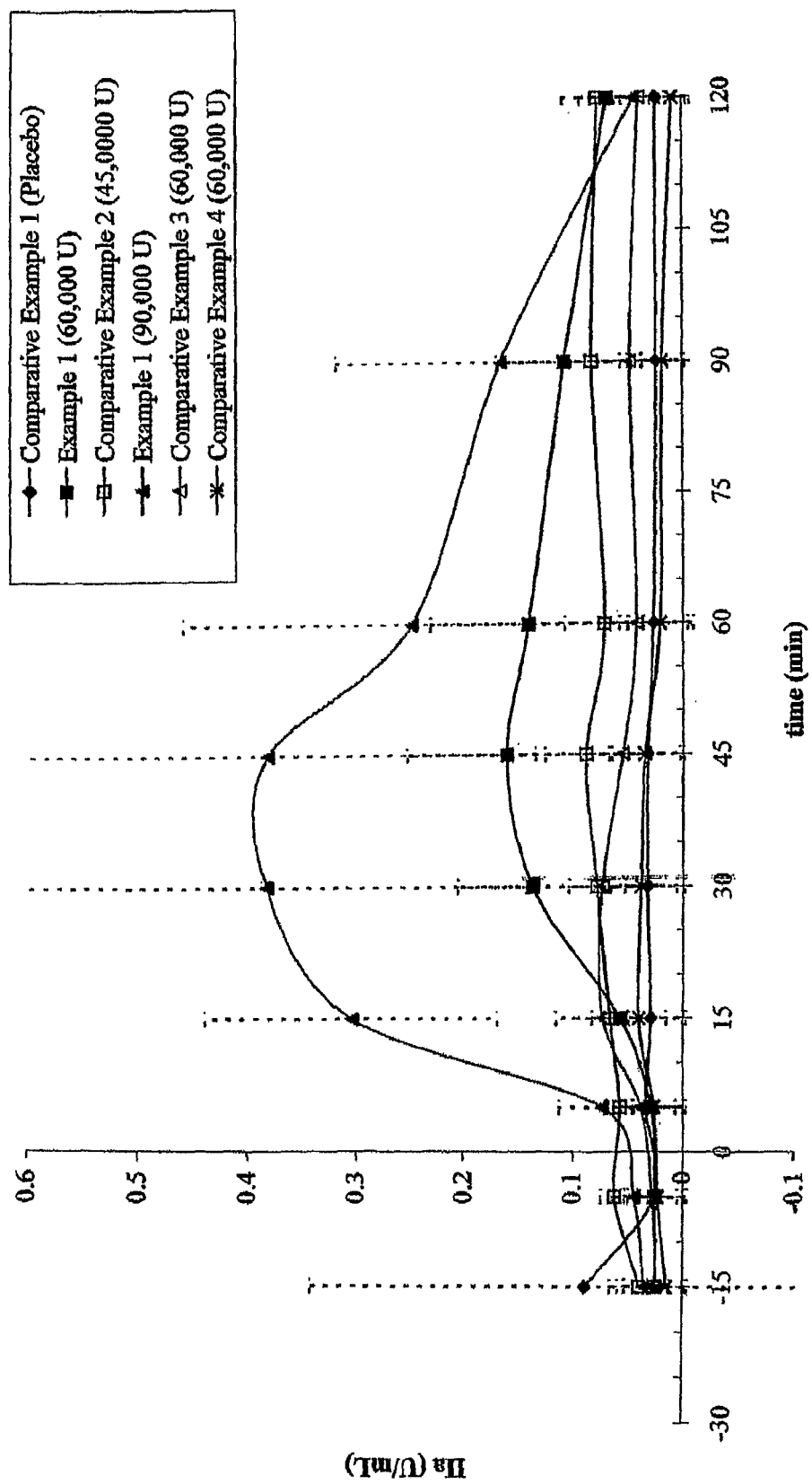
FIG. 2 is a graph of Anti-Factor IIa activity (IU/ml) versus time after administration of each of the pharmaceutical compositions of Example 1 and Comparative Examples 1-4.

As shown in Tables 6 and 8 and FIGS. 1 and 2, the wetted heparin formulations generally showed higher anti-Factor Xa and IIa activities (Periods 2 and 4) than the placebo (Period 1) and non-wetted heparin/SNAC tablets (Periods 3, 5, and 6). As shown in Table 13, the wetted heparin formulations generally showed increased Plasma aPTT times than the placebo and non-wetted heparin/SNAC tablets.

EXAMPLE 3

Soft gelatin capsules having the formulations shown in Tables 15a, 15b, and 15c were prepared as described below.

TABLE 15a

| Component | mg/capsule (3% by weight) |
|---|---|
| SNAC | 230.00 |
| Heparin Sodium, USP (15,000 units) | ≦107.14 |
| Polyethylene Glycol 300, NF (PEG 300) | 265.00 |
| Capmul ® PG8 | 107.00 |
| Purified Water, USP | 54.00 |
| Soybean Oil, USP Super Refined | QS (≧5.58) |
| Total weight | 765.00 |

TABLE 15b

| Components | mg/capsule | % of capsule weight | Acceptable range (mg) |
|---|---|---|---|
| SNAC | 383.00 | 28.24 | 371.5-394.5 |
| Heparin Sodium, USP (25,000 Units) | ≦178.57 | ≦13.17 | ≦173.2-184.0 |
| Polyethylene Glycol 300, NF (PEG 300) | 508.00 | 37.46 | 492.8-523.2 |
| Capmul ® PG8 | 190.00 | 14.01 | 184.3-195.7 |
| Purified Water, USP | 95.00 | 7.01 | 92.2-97.9 |
| Soybean Oil, USP Super Refined | ≧0.11 | ≧1.43 | ≧0.106-0.113 |
| Total weight | 1356.00 | 100.00 | 1315.3-1396.7 |

TABLE 15c

| Component | mg/capsule | % of Capsule Weight | Acceptable range (mg) |
|---|---|---|---|
| SNAC | 250.00 | 21.37 | 142.5-257.5 |
| Heparin Sodium, USP (37,500 Units) | ≦267.86 | ≦22.89 | ≦259.8-275.9 |
| Polyethylene Glycol 300, NF (PEG 300) | 405.00 | 34.62 | 392.9-417.2 |
| Capmul ® PG8 | 164.00 | 14.02 | 159.1-168.9 |
| Purified Water, USP | 81.99 | 7.00 | 79.5-84.4 |
| Soybean Oil, USP (Super Refined) | ≧1.15 | ≧0.10 | ≧1.12-1.18 |
| Total weight | 1170.00 | 100.00 | 1134.9-1205.1 |

Preparation of Gel Mass

The gel mass for the capsules had the formulation shown in Table 16 below and was prepared as follows. A gel holding tank was pre-heated to 55° C. The hot water jacket heater of the gel melter was turned on and the temperature controller set to 90° C. The required amount of purified water, USP was weighed out and charged into the gel melter and the mixer turned on. Approximately 3 kg of the required purified water, USP was reserved in a separate container for color transfer. The required amount of the glycerin, 99.7%, USP was charged into the gel melter followed by scraping of the container to assure complete transfer. The required amount of anhydrized liquid sorbitol, USP was charged into the gel melter and the container scrapped to ensure complete transfer. The access door and all release valves on the dome of the gel melter were then closed and left to heat until the temperature was greater or equal to 80° C. The gel melter access door and release valves were opened and the required amount of gelatin, NF charged into the gel melter and turn off the mixer after addition is completed. The access door and pressure valves were closed, the mixer turned on and the hot water jacket heater controller set to 85° C. Mixing and heating was continued for 75±10 minutes after the temperature had reached at least 80° C. The gel mass was inspected (if there is no visual evidence of un-dissolved particles the gel mass is done). The vacuum pump water hose was connected to the water outlet and the cold water and vacuum pump turned on. The gel mass was deaerated and the mixer and vacuum pump turned off after the gel mass had no visual evidence of air bubbles.

The White Opatint G-18000 was mixed thoroughly in its original container with a stainless steel paddle and the required amount was weighed out. The FD&C Green No. 3 and D&C Yellow No. 10 were weight out and dissolved in approximately one fourth (¼th) of the reserve water.

The access door of the gel melter was opened and the Opatint and the dye mixture were slowly added with the mixer on. The release valves and the access door were then closed and the vacuum pump turned on. The colorized gel mass was deaerated for 10±5 minutes followed by release of all valves and turning off the mixer and vacuum pump. Samples were taken for viscosity and water content determination. The water content of the gel mass was adjusted to approximately 26% by adding water if it was less than 26% or further heating if it was above 26%. The gel mass was transferred to a pre-heated, pre-weighed gel holding tank and the temperature maintained at about 55° C.

TABLE 16

| Component | Quantity required (kg) | % w/w | Range (mg) |
|---|---|---|---|
| Gelatin, NF (150 Bloom Limed Bone, Type B) | 61.500 | 41.00 | 59.66-63.35 |
| Glycerin, 99.7%, USP | 21.000 | 14.00 | 20.37-21.63 |
| Anhydrized Liquid Sorbitol, USP (Sorbitol Special, 76%) | 13.500 | 9.00 | 13.10-13.91 |
| Purified Water, USP | 50.964 | 33.98 | 49.44-52.49 |
| White Opatint G-18000 | 3.000 | 2.00 | 2.91-3.09 |
| FD&C Green No. 3 | 0.021 | 0.014 | 0.02-0.022 |
| D&C Yellow No. 10 | 0.015 | 0.010 | 0.0146-0.0155 |
| Total weight | 149.996 | | 145.50-154.50 |

Preparation of Heparin/SNAC Soft Gelatin Capsules

The required amount of heparin sodium, USP was milled to a particle size not more than 180 μm using a Quadro Comil® 197 equipped with a round impeller and a Comil Screen 2A006R04227587 (80 Mesh). The required amounts of polyethylene glycol 300, NF (PEG 300) Capmul® PG8, purified water, USP, and the soybean oil, USP were weighed out and transferred to an appropriately sized stainless steel container. An overhead stirrer was placed into the mixture and the container placed on a hot plate. Mixing and heating were than initiated. Heating was continued until the mixture temperature reached 40 ±10° C. after which the mixture was blanketed with nitrogen.

For the 250 mg/37,500 IU formulation, SNAC was charged into the mixture while stirring. Mixing was continued until the SNAC was well distributed. Heparin sodium, USP was charged into the mixture with continuous stirring. Mixing was continued until the heparin was well distributed. The mixer was then turned off and the mixer blades and shaft scraped to clean.

For the 383 mg/25,000 formulation, the SNAC and milled heparin were blended in a bag for about 1 minute. The resulting blend was charged into the solvent system and mixing was continued until the heparin/SNAC blend was well distributed. The mixer was then turned off and the mixer blades and shaft scraped to clean.

For either formulation the resulting suspension was removed from the hot plate and milled using a Vertical Colloid Mill with hopper. The aggregate size of the suspension before and after milling was determined using a using a fineness of grind gauge. Milling was continued until the aggregate size was less than 180 μm. The temperature of the suspension was measured after completion of milling. If necessary the suspension was reheated to a temperature between 30-50° C. The suspension was then placed in to a vacuum chamber and deaerated until no bubbles were observed. In-process samples of Heparin/SNAC suspension were then collected. The heparin/SNAC suspension was covered and maintained at 30-50° C. with continuous slow mixing.

The heparin/SNAC soft gelatin capsule formulation was encapsulated with the gel mass prepared as described above using a Bochang Encapsulator. 1% w/w soybean lecithin solution with Miglyol 812 (carylic/capric triglyceride) was used as a lubricant for the encapsulator machine. The heparin/SNAC suspension was charged into the hopper of the encapsulator and continuously stirred. The equipment was set-up so that the target capsule fill weight was 1267 mg with an acceptable range of 1204 to 1330 mg, the trailing edge seam thickness acceptable limit was at least 0.25 mm and the ribbon thickness had a target of 0.81±0.05 mm. After encapsulation, the capsules were dried until the gel shell moisture content was less or equal to 8% and the water content of the fill material (heparin/SNAC suspension) was less or equal to 9%. After drying samples were sent for release testing. The capsules were then packaged in a 100 cc white HDPE wide mouth bottle with 38 mm Child Resistant, foil lined, suitable for induction sealing caps and low moisture cotton coil. Thirty (30) capsules were filled per bottle.

EXAMPLE 4

Hard gelatin capsules containing 15,000 IU heparin, 250 mg SNAC, 15% (w/w) Capmul® PG8 (propylene glycol monocaprylate) or Capmul® MCM (glyceryl caprylate/caprate) (available from Abitec Corp. of Columbus, Ohio), 37% PEG 300, and 1% sodium lauryl sulphate were prepared as described below. Hard gelatin capsules were also prepared with the aforementioned formulation without SNAC or with 2% Carbopol® 934P (available from Noveon of Cleveland, Ohio).

First, the liquid excipients (e.g., Capmul® PG-8 or Capmul® MCM and PEG-300) were mixed in a mortar to obtain a homogeneous liquid mixture. To this mixture, various solid components were slowly incorporated in proportions until a homogeneous mixture of paste (or suspension) consistency was obtained. These solid materials included SNAC, heparin, sodium lauryl sulphate, and optionally Carbopol® 934P. Once the homogeneity of the paste (or suspension) was ensured, the mixture was manually filled into appropriate size hard gelatin capsules. The filled capsules were sealed at the joint between the body and cap by wetting the rim of the body with 50:50 (% v/v) mixture of ethyl alcohol and purified water. The capsules were stored frozen at −20° C. until used.

EXAMPLE 5

Soft gelatin capsules having the formulations shown in Table 15a, prepared as described in Example 3, were administered to 4 male Rhesus monkeys as follows. Rhesus monkeys weighing between 3.5-5.0 kg were fasted overnight before the experiments and food was returned about 2 hours after dosing of the solid. Water was withheld from 30 minutes prior to dosing until 30 minutes after dosing, except for those quantities used for dosing. Each dosage form was delivered to the rear of the mouth using a pill gun. After release of the dosage form, 5 ml of reverse osmosis water was administered into the oral cavity to facilitate swallowing. Following delivery, the oral cavity was inspected to ensure that the solid was swallowed.

Hard gelatin capsules having the formulation shown in Table 1 and prepared as described in Example 1 were administered to 7 male Rhesus monkeys as described above.

Figure 3:
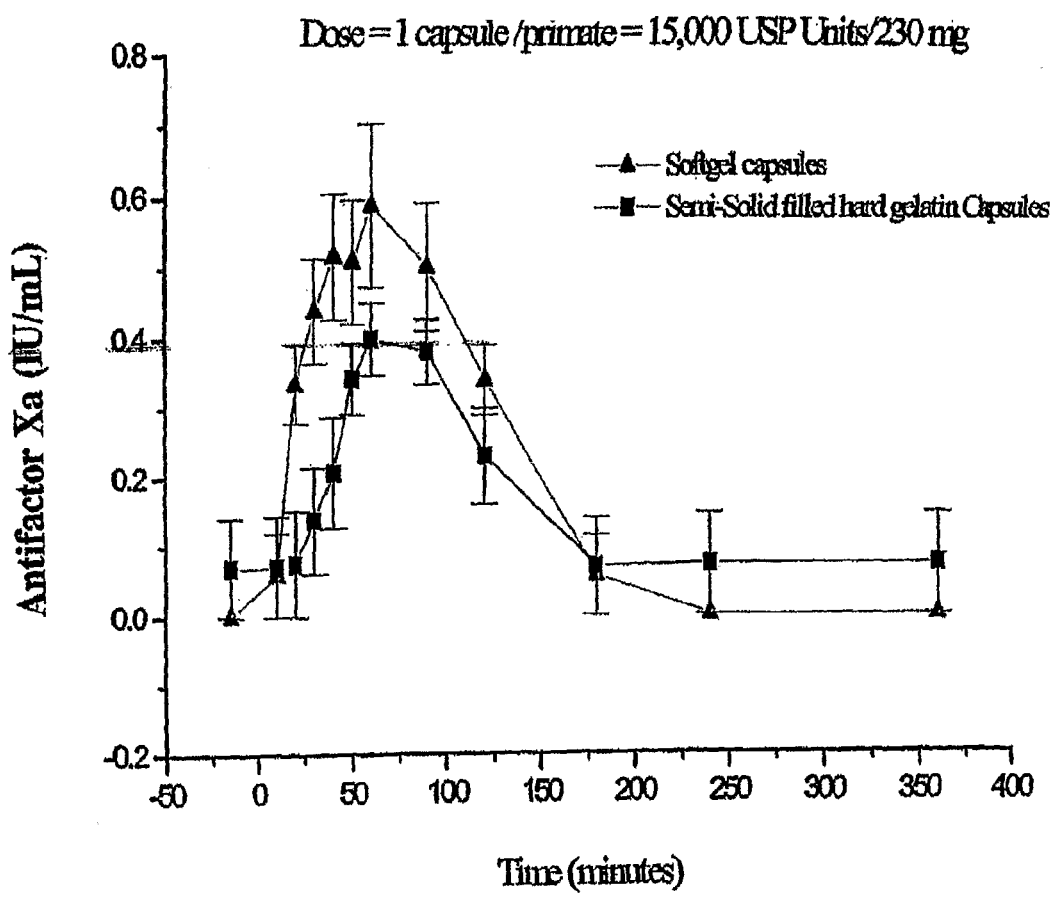
FIG. 3 is a graph of Antifactor Xa activity (IU/ml) versus time after administration of a capsule having the formulation shown in Table 15a (Example 3) or Table 1 (Example 1) to Rheses monkeys (1 capsule/monkey).

Antifactor Xa from blood samples was measured over 400 minutes. The results for each group was averaged, and are shown in FIG. 3.

EXAMPLE 6

Hard gelatin capsules having the formulation described in Example 4 (15,000 IU heparin, 250 mg of SNAC, 15% (w/w) Capmul® PG8, 37% PEG 300, and 1% sodium lauryl sulphate) with and without 2% Carbopol® 934P were prepared. Hard gelatin capsules having the formulation described in Example 4, but without the SNAC were also prepared.

The capsules containing SNAC and heparin with or without Carbopol were administered to 8 Cynos monkeys by the following procedure. Cynomolgus monkeys were fasted at least 24 hours prior to dosing. One capsule was inserted at the tip of a tubing, and air flushed to discharge the capsule into the stomach. Food was returned 2 hours after dosing. Water was available at all times. Approximately 1.3 ml of whole blood was collected into citrated tubes at pre-dose, and over 400 minutes post dosing. Antifactor Xa from the blood samples was measured.

The capsules without SNAC were administered to 4 Cynos monkeys as described above.

Figure 4:
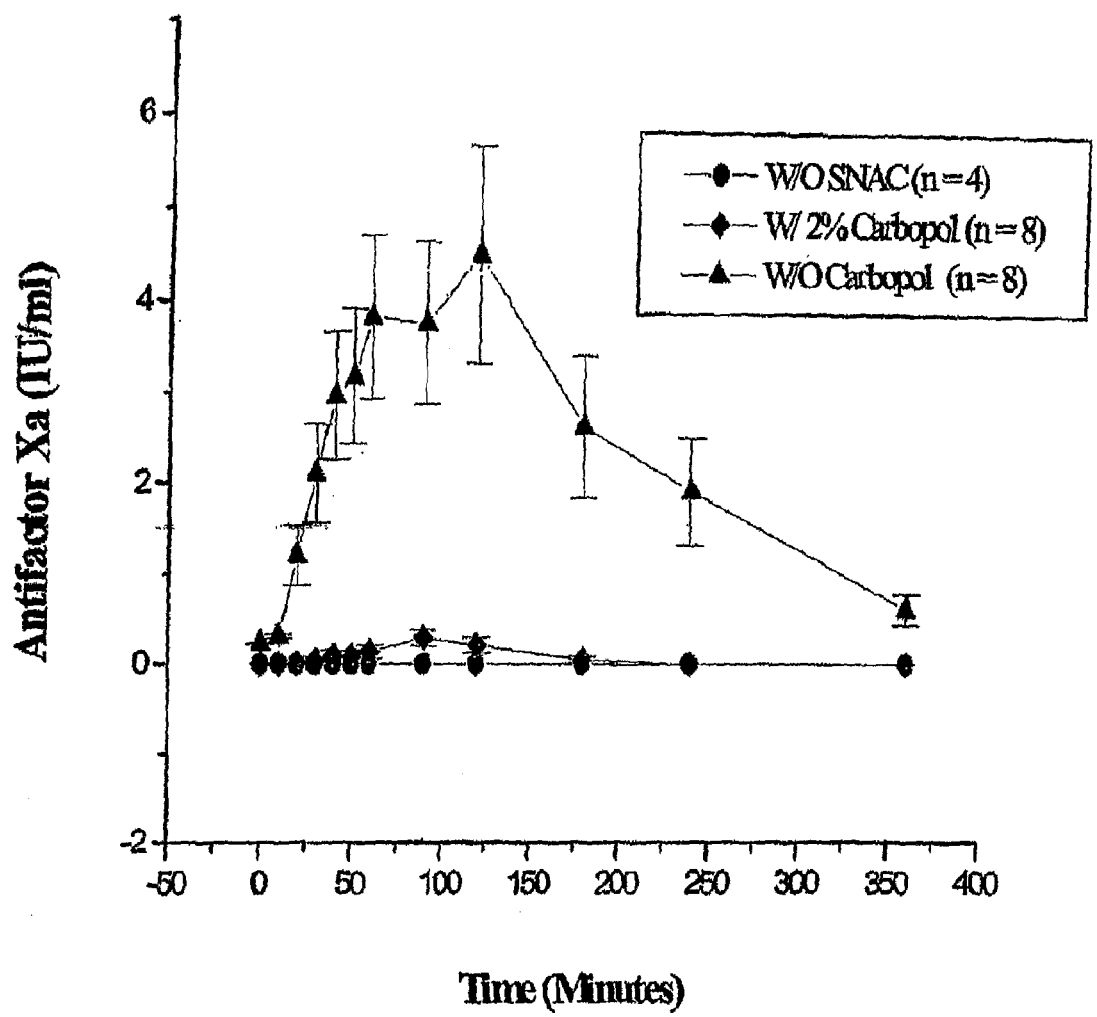
FIG. 4 is a graph of Antifactor Xa activity (IU/ml) versus time after administration of the capsules described in Example 6 to Cynos monkeys (1 capsule/monkey).

The results for each of the three groups were averaged, and are shown in FIG. 4.

EXAMPLE 7

Hard gelatin capsules having the formulation shown in Table 17, and prepared as described in Example 1 were prepared. The capsules were administered to a group of 8 Rhesus monkeys (1 capsule/monkey) by the procedure described in Example 5.

TABLE 17

| Component | Amounts |
| --- | --- |
| SNAC | 250.0 mg |
| Heparin sodium, USP | 15,000 IU |

TABLE 17-continued

| Component | Amounts |
| --- | --- |
| Polyethylene Glycol (PEG) 300 | 37 wt % |
| Sodium Lauryl Sulphate | 1 wt % |
| Capmul PG8 (Propylene glycol monocaprylate) | 15 wt % |

Figure 5:
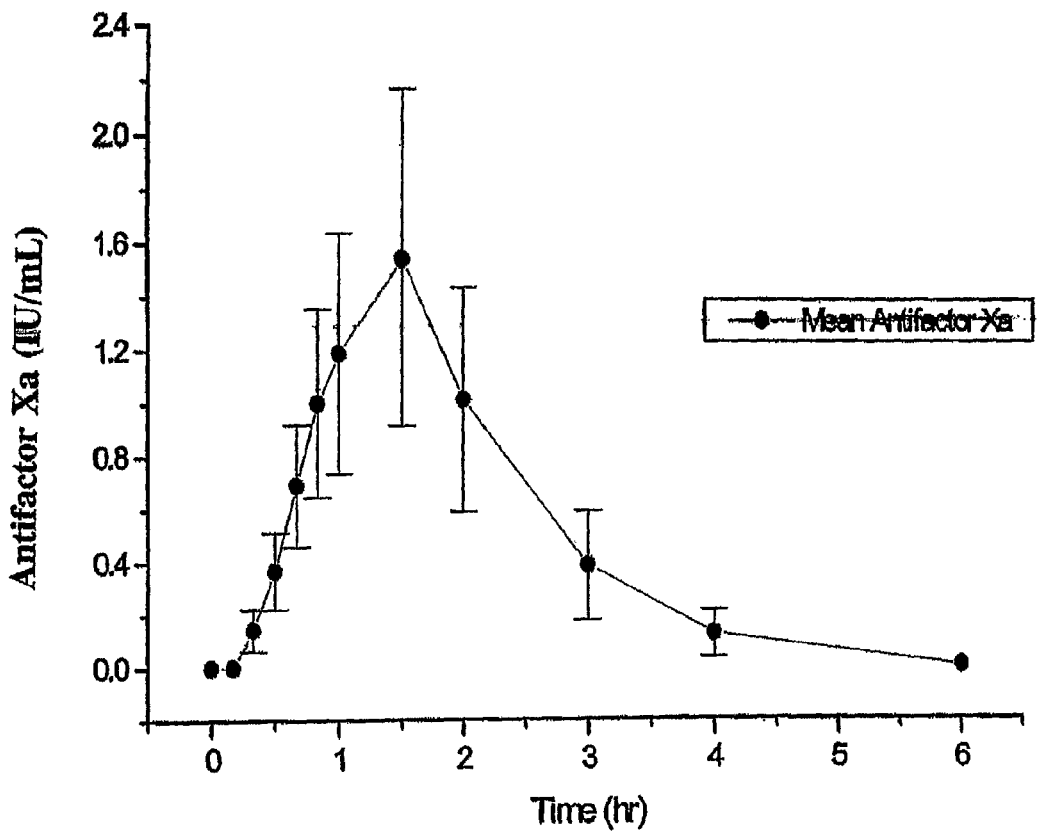
FIG. 5 is a graph of Antifactor Xa activity (IU/ml) versus time after administration of the capsules described in Example 7 to Rhesus monkeys (1 capsule/monkey).

Antifactor Xa was measured from blood samples over 6 hours. The results were averaged, and are shown in FIG. 5.

EXAMPLE 8

Hard gelatin capsules having the formulation shown in Table 18 were prepared as described in Example 1. The capsules were administered to a group of 8 Rhesus monkeys.

TABLE 18

| Component | Amounts |
| --- | --- |
| SNAC | 250.0 |
| Heparin sodium, USP | 14,930 IU |
| Polyethylene Glycol (PEG) 300 | 37% |
| Sodium Lauryl Sulphate | 1 |
| Capmul ® MCM (mono and di-glycerides of medium chain fatty acids (mainly caprylic and capric)) | 15% |

Capmul® MCM is available from Abitec Corporation of Columbus, Ohio. This formulation is identical to that of Example 7 except Capmul® MCM is substituted for Capmul® PG8.

Figure 6:
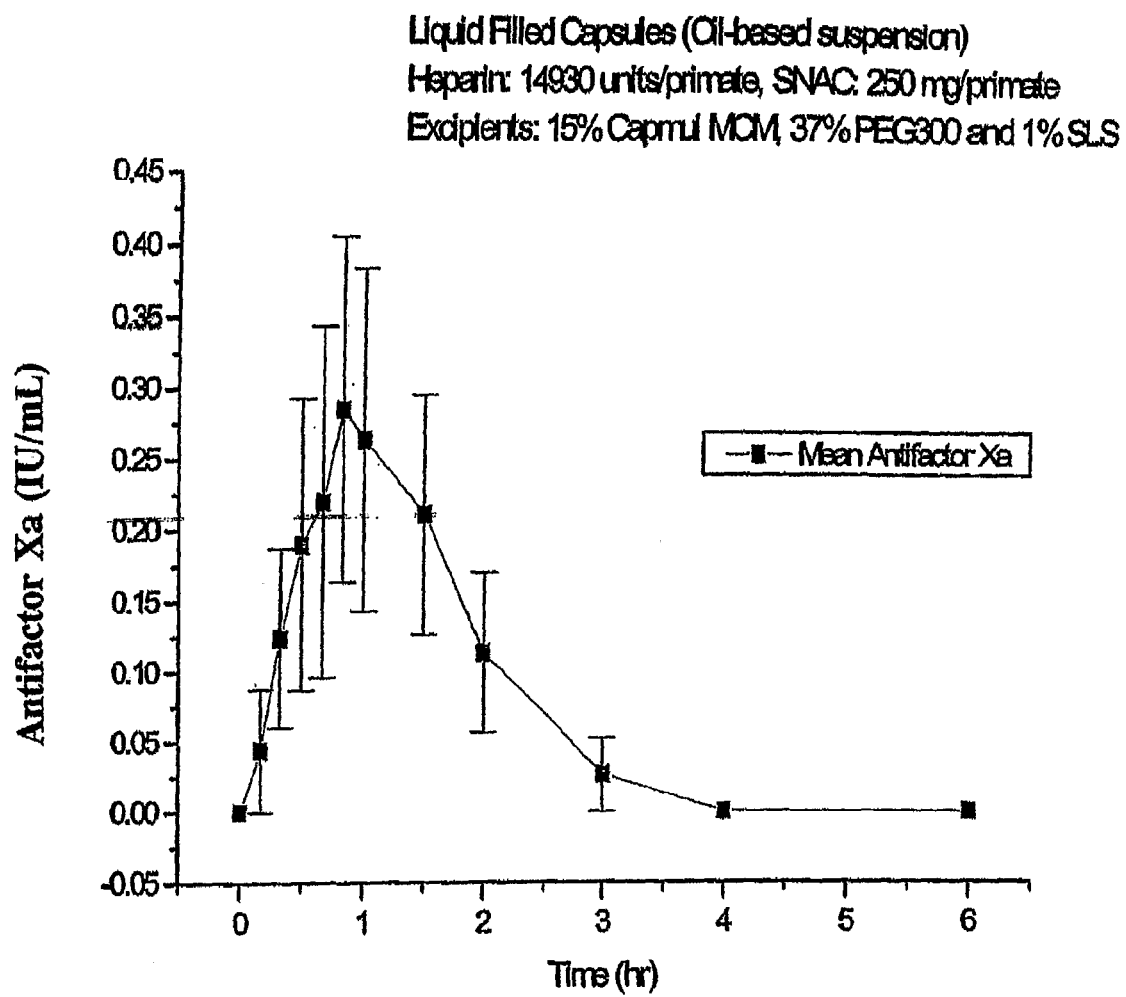
FIG. 6 is a graph of Antifactor Xa activity (IU/ml) versus time after administration of the capsules described in Example 8 to Rhesus monkeys (1 capsule/monkey).

Antifactor Xa was measured from blood samples over 6 hours. The results were averaged, and are shown in FIG. 6.

Figure 7:
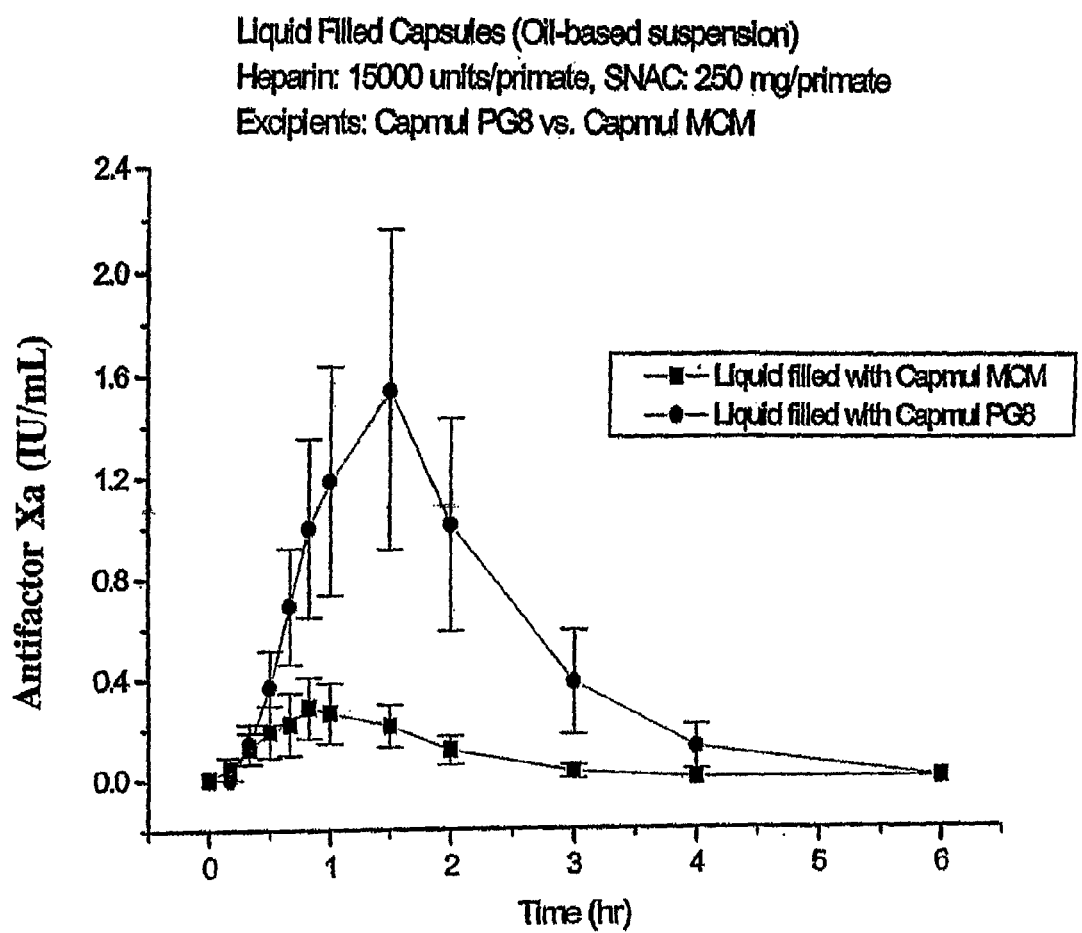
FIG. 7 is an overlay of FIGS. 5 and 6.

The results of from Examples 7 and 8 (FIGS. 5 and 6) are overlayed in FIG. 7.

EXAMPLE 9

Hard gelatin capsule having the formulation shown in Table 1 and prepared as described in Example 1 was administered to 4 Rhesus monkeys (1 capsule/monkey) by the procedure described in Example 5. Antifactor Xa was measured over a period of about 400 minutes after administration.

Figure 8:
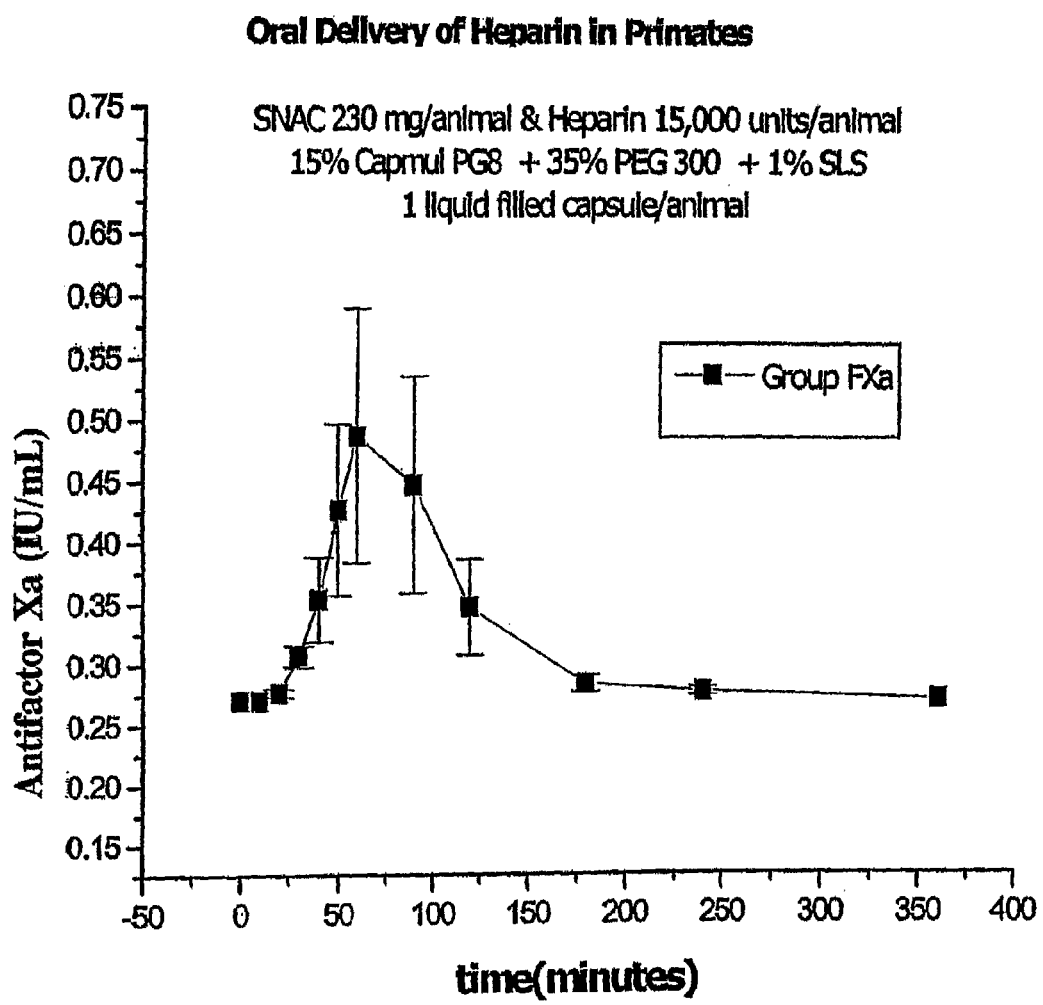
FIG. 8 is a graph of Antifactor Xa activity (IU/ml) versus time after administration of the capsules described in Example 9 to Rhesus monkeys (1 capsule/monkey).

The results were averaged and are shown in FIG. 8.

EXAMPLE 10

Hard gelatin capsules having the formulation shown in Table 1 and prepared as described in Example 1 were administered to a group of 4 Rhesus monkeys (1 capsule/monkey) by the procedure described in Example 5.

Figure 9:
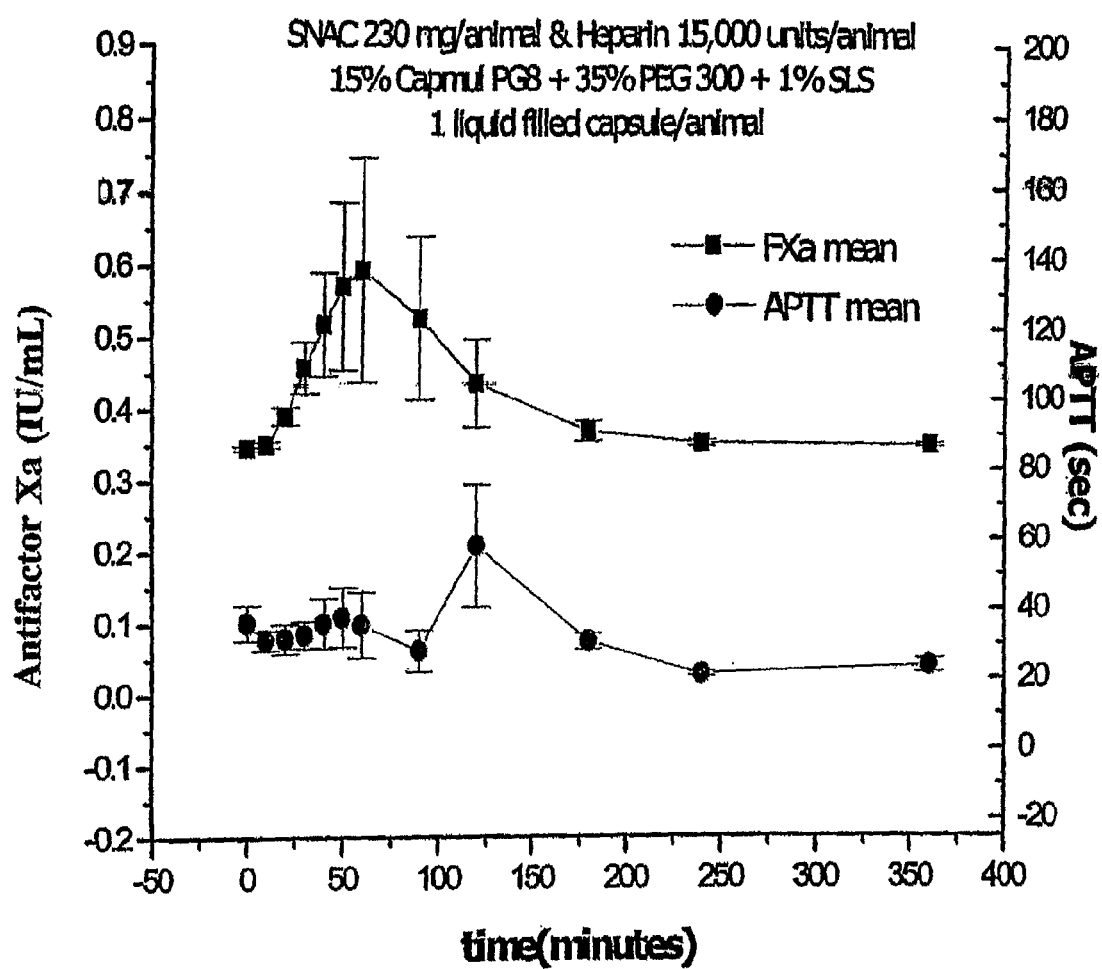
FIG. 9 is a graph of Antifactor Xa activity (IU/ml) and aPTT versus time after administration of the capsules described in Example 10 to Rhesus monkeys (1 capsule/monkey).

Antifactor Xa activities and aPTT were measured over 400 minutes. The results were averaged and are shown in FIG. 9.

EXAMPLE 11

Hard gelatin capsules having the formulation shown in Table 19 were prepared as described in Example 1. The capsules were administered to 4 Rhesus monkeys (1 capsule/monkey) by the procedure described in Example 5.

TABLE 19

| Component | Target Amount (mg/capsule) |
| --- | --- |
| SNAC | 229.59 |
| Heparin sodium, USP | 107.14 (15,000 IU) |
| Polyethylene Glycol (PEG) 300 | 226.13 |
| Propylene glycol monocaprylate (Capmul ® PG8) | 100.44 |

Figure 10:
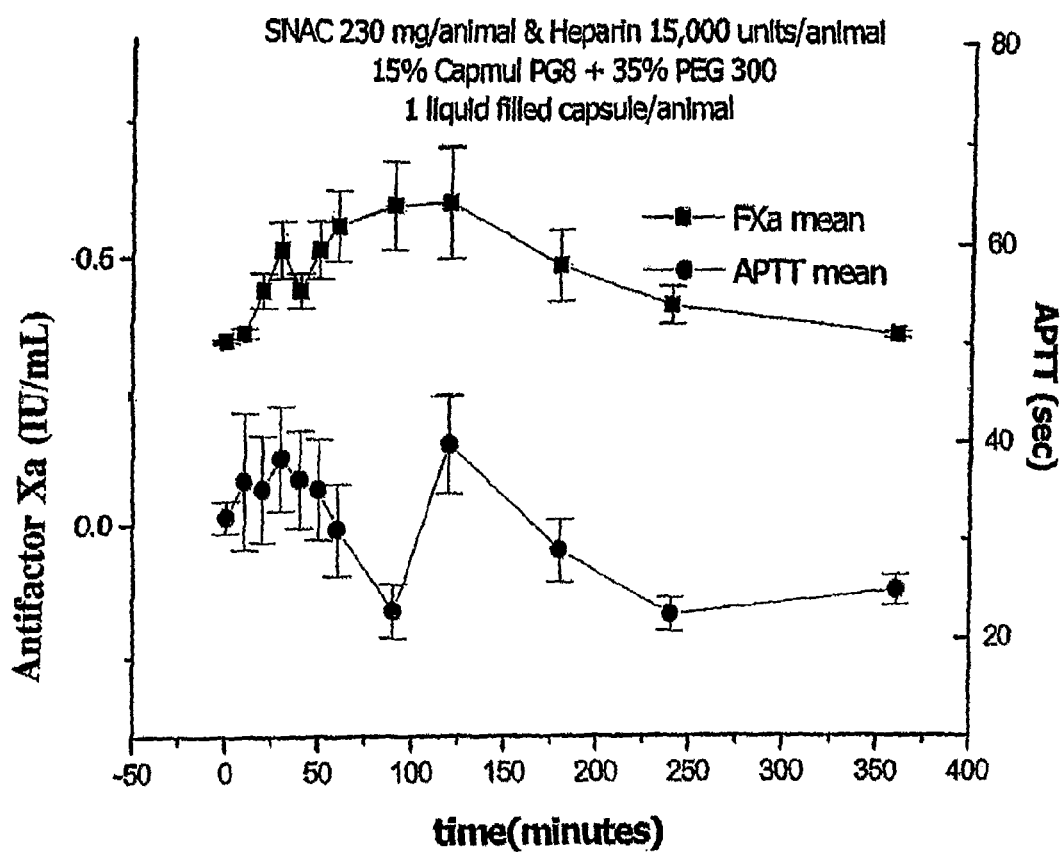
FIG. 10 is a graph of Antifactor Xa activity (IU/ml) and aPTT versus time after administration of the capsules described in Example 11 to Rhesus monkeys (1 capsule/monkey).

The formulation of Table 19 is identical to the formulation of Table 1 except sodium lauryl sulfate is excluded. Antifactor Xa activities and APTT were measured over 400 minutes. The results were averaged and are shown in FIG. 10.

EXAMPLE 12

Hard gelatin capsules having the formulation of Example 1, but with varying amounts of SNAC such that the ratio of SNAC:Heparin was 0.5:1, to 1:1, 2:1, and 2.5:1. (In Example 1, the SNAC:heparin ratio was about 2.5:1). The capsules were administered to Rhesus monkeys (1 capsule/monkey) by the procedure described in Example 5. The formulations containing 0.5:1, 1:1, 2:1, 2.5:1 of SNAC:heparin were administered to 4, 4, 4, and 7 monkeys, respectively.

Figure 11:
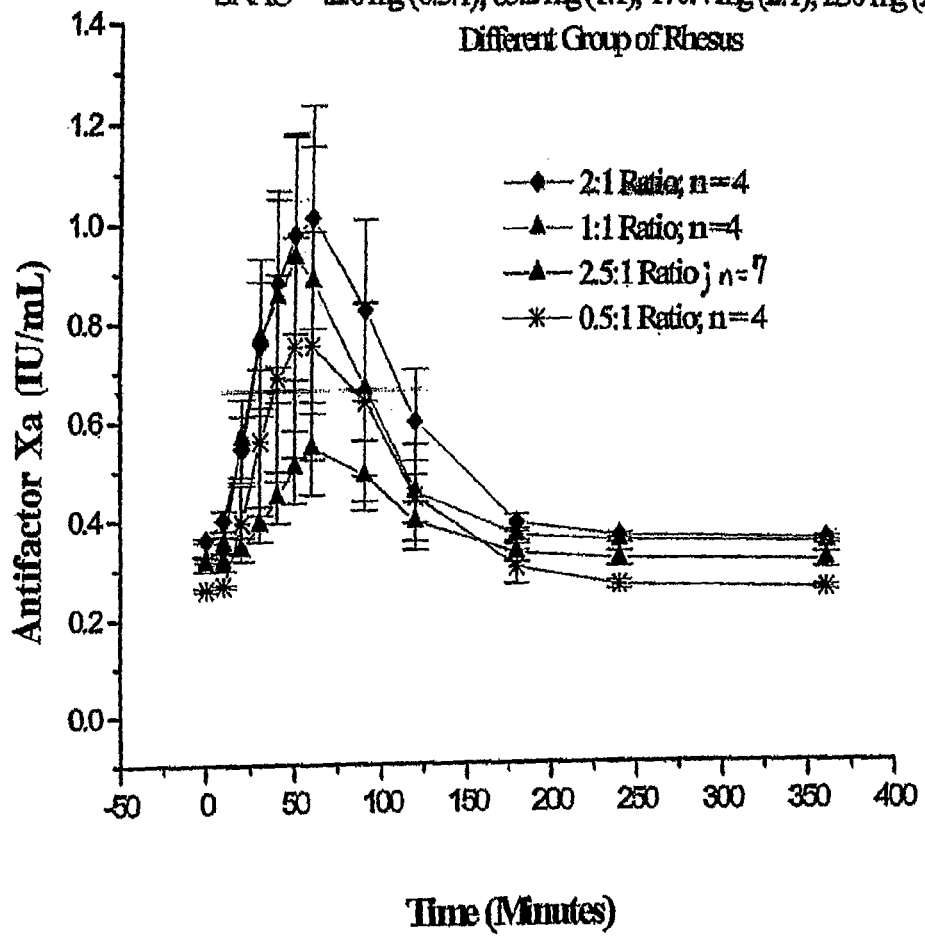
FIG. 11 is a graph of Antifactor Xa activity (IU/ml) versus time after administration of the capsules described in Example 12 to Rhesus monkeys (1 capsule/monkey).

Antifactor Xa activities were measured from blood samples over a period of about 400 minutes. The averages for the four groups are shown in FIG. 11.

EXAMPLE 13

Stability tests were conducted on the hard gelatin capsules described in Example 1. The capsules were administered to Rhesus monkeys by the procedure described in Example 5. The capsules were stored for 15 days at 40° C. and 75% relative humidity or 25° C. and 60% relative humidity. The capsules were then administered to two groups of Rhesus monkeys. Antifactor Xa activities and aPTT were measured over about 400 minutes for each administration.

Figure 12:
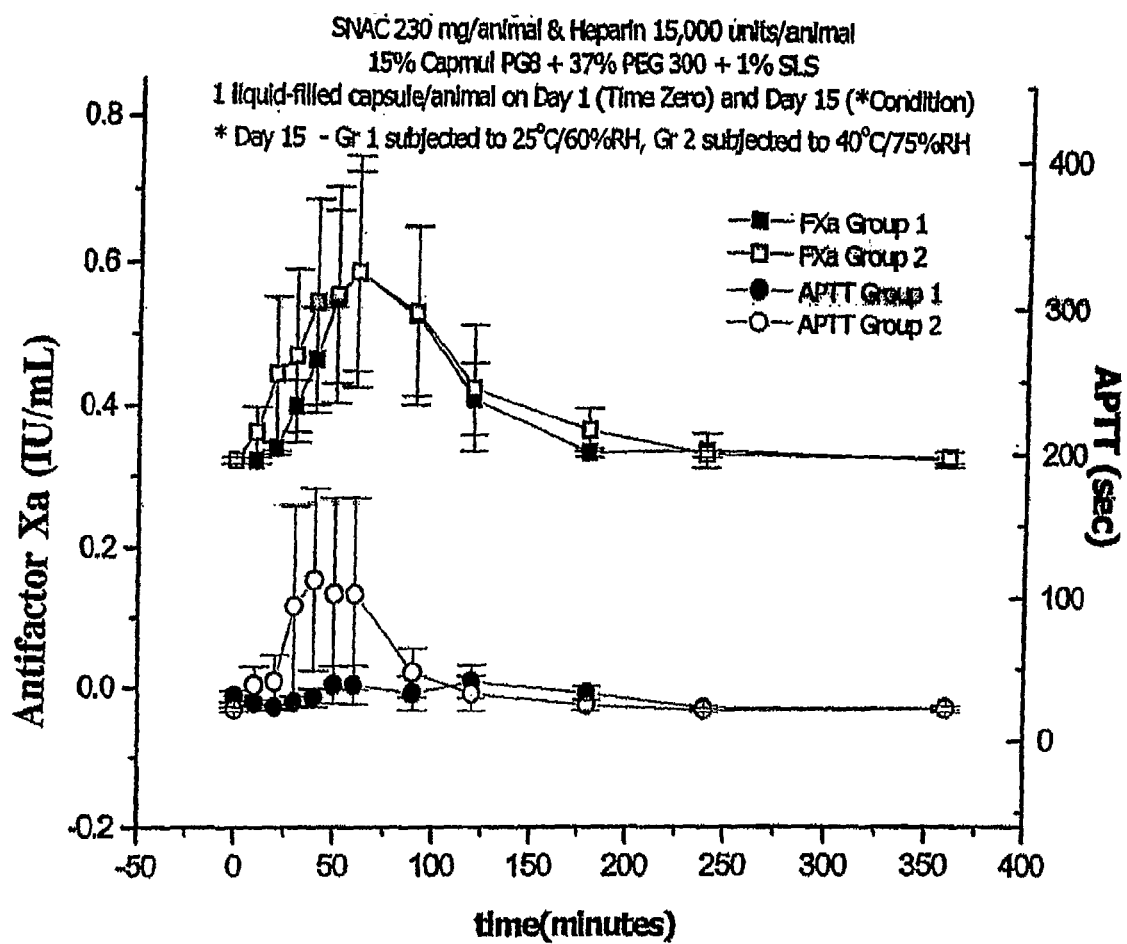
FIGS. 12 and 13 are graphs of Antifactor Xa activity (IU/ml) and aPTT versus time after administration of the capsules described in Example 13 after storage for 15 days at 40° C. and 75% relative humidity (FIG. 12) or 25° C. and 60% relative humidity (FIG. 13) to Rhesus monkeys (1 capsule/monkey).
Figure 13:
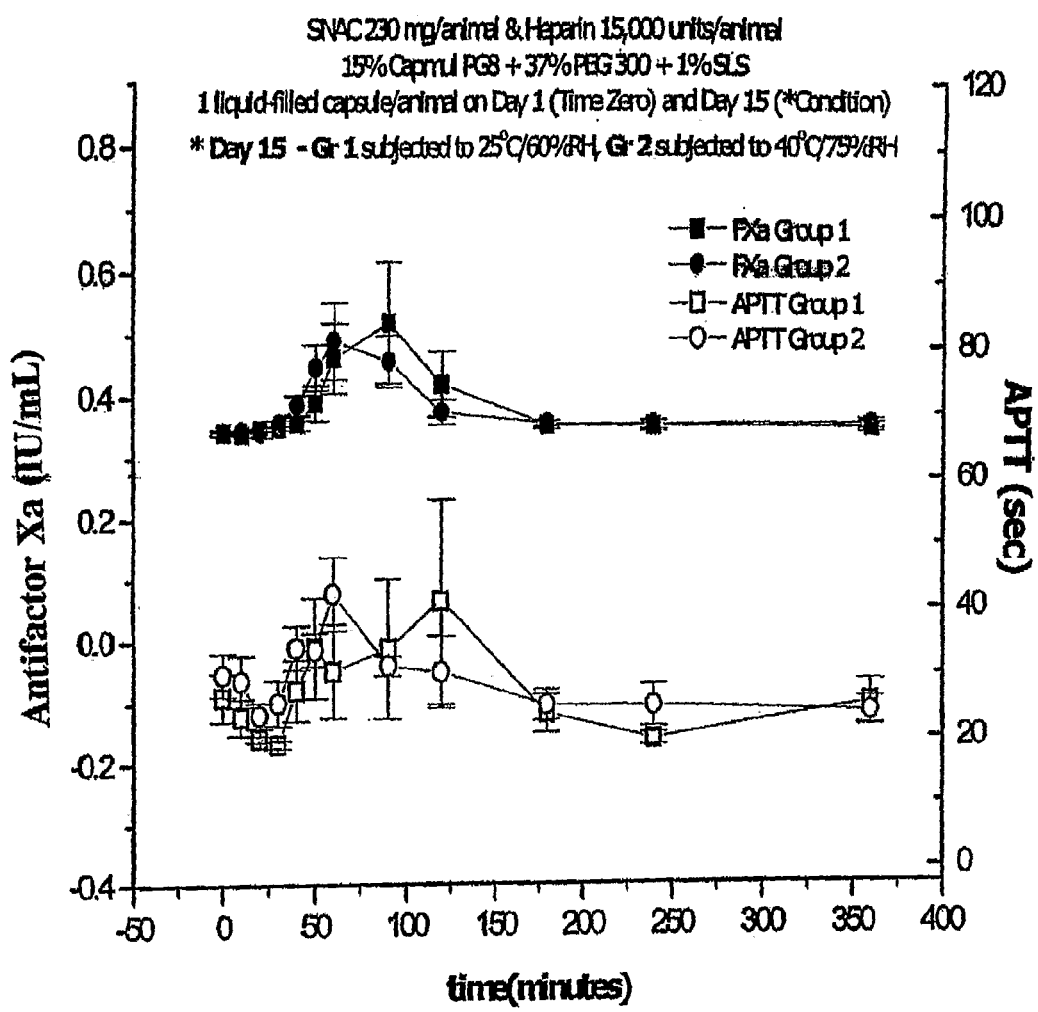

These results were averaged and are shown in FIGS. 12 and 13.

Figure 14:
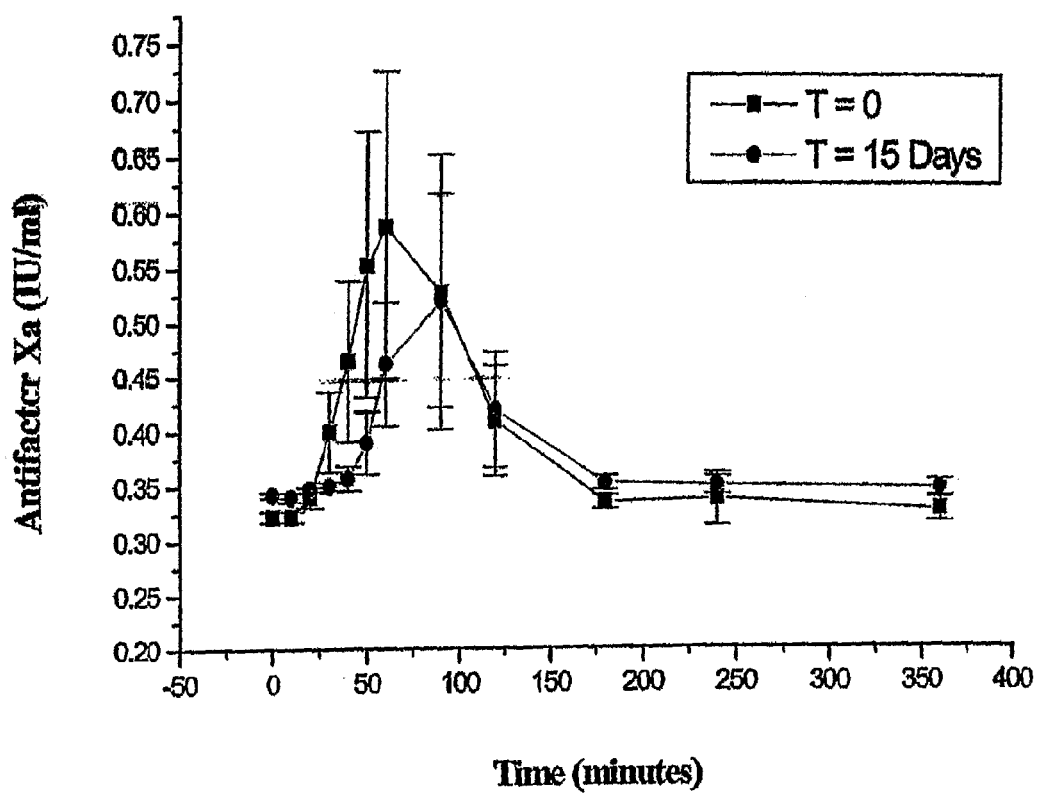
FIGS. 14 and 15 are graphs of Antifactor Xa activity versus time after administration of the capsules described in Example 13 before and after 15 days of storage at 40 ° C. and 75% relative humidity or 25° C. and 60% relative humidity for fifteen days to Rhesus monkeys (1 capsule/monkey).
Figure 15:
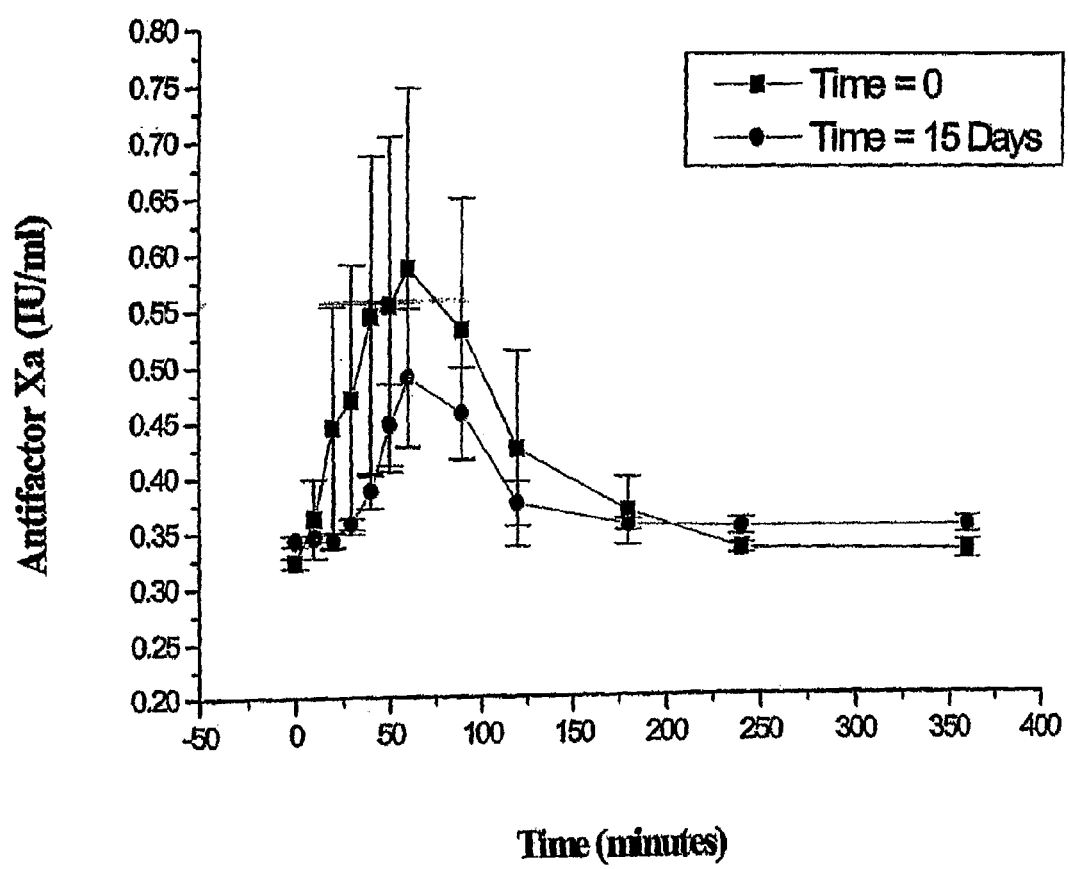

FIG. 14 compares the Average Antifactor Xa activities for the semi-solid capsules described in Example 1 and administered the day it was formulated (t=0) and after 15 days (t=15 days) at 25° C./60% RH. FIG. 15 compares the Average Antifactor Xa activity for the semi-solid capsule described in Example 1 and administered the day it was formulated (t=0) and after 15 days (t=15 days) at 25° C./75% RH. The capsules were administered to Rhesus monkeys by the procedure described in Example 5.

COMPARATIVE EXAMPLE 5

Preparation of Tablets (without Heparin)

Tablets having the formulation described in Table 20 were prepared as described below.

TABLE 20

| Component | mg/Tablet (Target) | % of tablet weight | mg/Tablet (acceptable range) |
| --- | --- | --- | --- |
| SNAC | 383.00 | 47.88 | 371.51-394.49 |
| Propylene Glycol, USP/EP/JP | 40.0 | 5.00 | 38.80-41.2 |
| Capmul ® PG8 | 80.0 | 10.00 | 77.6-82.40 |
| Dibasic Calcium Phosphate, Anhydrous, USP/EP (Anhydrous Emcompress) | ≧268.75 | ≧33.59 | |
| Colloidal Silicon Dioxide, USP/NF/EP (Aerosil ® 200 VV Pharma) | 16.00 | 2.00 | 15.52-16.48 |
| Povidone K90, USP/EP/JP (Kollidon 90F) | 4.25 | 0.53 | 4.12-4.37 |
| Magnesium Stearate, NF/EP/JP | 8.00 | 1.00 | 7.76-8.24 |
| Total weight | 800.00 | 100.00 | 776-824.00 |

The SNAC and a portion of the intragranular Emcompress™ (available from JRS Pharma, Patterson, N.Y.) were weighed out, transferred to a 16 quart stainless steel V-blender shell and blended for 15 minutes. The resulting blend was then divided into four sub-lots for granulation. For the granulation of each sub-lot the SNAC blend was transferred to a 5 L bowl of a Key Instruments KG-5 high shear granulator (available from Key Instruments, Trevose, Pa.). Granulation was first performed using a mixture of the required amount of Capmul® PG8 and propylene glycol as the granulation fluid followed by the required amount of Povidone $K_{90}$ solution (available from BASF, Ludwigshafen, Germany) in water as the granulation fluid. The granulation was completed with purified water as the final granulation fluid. The resulting granulation was transferred to a polyethylene lined container for in-process storage. The other three sub-lots were also granulated and stored in a similar fashion. The granulations were transferred to stainless steel trays and dried in a vacuum oven at about 40° C. for at least 4 hours. The dried granules were transferred into a polyethylene bag and blended for not less than one minute. The blended granules were milled using a Vector Granul Mill Jr. mill (available from Vector Corp., Marion, Iowa) equipped with a 35 mesh screen. The moisture content of the milled granules was determined using a Karl-Fisher Coulometer. The granules were considered dry if the moisture content was not more than 10% w/w. If the moisture content was more than 10% w/w, drying was continued until an acceptable moisture content was obtained. The moisture content of the granulation was used for calculations to adjust the quantity of extragranular anhydrous Emcompress™ to be added to the granulation. The dried granules were transferred to a polyethylene lined container for in-process storage.

The required amount of Aerosil® 200 VV Pharma (available from Degussa AG, Wolfgang, Germany) was sieved through a 35 mesh screen. The remaining portion of amount of anhydrous Emcompress™ was also weighed. The dried granules were then transferred to a 16 Quart stainless steel V-blender shell. The Aerosil® 200 VV Pharma and the anhydrous Emcompress™ were transferred to the same V-Blender shell. The shell was mounted on to the Yoke of a Patterson-Kelly V-blender drive unit (available from Patterson-Kelly Co., East Stroudsburg, Pa.) and blended for 15 minutes. After successful blend uniformity testing, the required amount of magnesium stearate was weighed out, screened through a 35 mesh screen and transferred to the V-blender shell. The material was blended for 3 minutes. The resulting blend was compressed into tablets using a Korsch EK-O (available from Mori Machinery Co., Okayama, Japan) single station tablet press equipped with 16.5 mm by 7.5 mm oval shaped tooling. During compression, the following in-process tests were performed, friability, tablet hardness, tablet weight, tablet thickness and disintegration. The target tablet weight was 800 mg with an acceptable range of 776-824 mg and the target tablet hardness was 8 Kp with an acceptable range of 5-11 KP. After release testing, the tablets were packaged in 30 count HDPE bottles with pharmaceutics coil, child resistant cap and induction seal liner.

COMPARATIVE EXAMPLE 6

Preparation of Heparin/SNAC Tablets (25,000/383)

Heparin/SNAC tablets having the formulation described in Table 21 were prepared as described below.

TABLE 21

| Component | mg/Tablet (Target) | % of Tablet weight | mg/Tablet (acceptable range) |
|---|---|---|---|
| SNAC | 383.00 | 47.88 | 371.51-394.49 |
| Heparin Sodium, USP (25,000 Units) | ≦178.57 | ≦22.32 | 173.21-183.93 |
| Propylene Glycol, USP/EP/JP | 40.00 | 5.00 | 38.80-41.2 |
| Capmul ® PG8 | 80.00 | 10.00 | 77.6-82.40 |
| Dibasic Calcium Phosphate, Anhydrous, USP/EP (Anhydrous Emcompress ™) | ≧90.18 | ≧11.27 | 87.47-92.89 |
| Colloidal Silicon Dioxide, USP/NF/EP (Aerosil ® 200 VV Pharma) | 16.00 | 2.00 | 15.52-16.48 |
| Povidone K90, USP/EP/JP (Kollidon 90F) | 4.25 | 0.53 | 4.12-4.37 |
| Magnesium Stearate, NF/EP/JP | 8.00 | 1.00 | 7.76-8.24 |
| Total weight | 800.00 | 100.00 | 776-824.00 |

The required amount of heparin sodium, USP and milled SNAC were weighed out, transferred to a 16 quart stainless steel V-blender shell and blended for 15 minutes. The resulting blend was divided into four sub-lots for granulation. For the granulation of each sub-lot the heparin/SNAC blend was transferred to a 5 L bowl of a Key Instruments KG-5 high shear granulator. Granulation was first performed using a mixture of the required amount of Capmul® PG8 and propylene glycol as the granulation fluid followed by the required amount of Povidone K90 solution in water as the granulation fluid. The granulation was completed with purified water, USP as the final granulation fluid. The resulting granulation was transferred to a polyethylene lined container for in-process storage. The other three sub-lots were also granulated and stored in a similar fashion. The granulations were then transferred to stainless steel trays and dried in a vacuum oven at about 40° C. for at least 4 hours. The dried granules were transferred into a polyethylene bag and blended for not less than one minute. The blended granules were milled using a Vector Granul Mill Jr. mill equipped with a 35 mesh screen. The moisture content of the milled granules was determined using a Karl-Fisher Coulometer. The granules were considered dry if the moisture content was not more than 10% w/w. If the moisture content was more than 10% w/w drying was continued. Samples were drawn for assay of SNAC and heparin in the dry granulation. The heparin assay (as is) was used for calculations to adjust the quantity of extragranular anhydrous Emcompress™ to be added to the granulation. The dried granules were transferred to a polyethylene lined container for in-process storage.

The required amount of Aerosil® 200 VV Pharma was sieved through through a 35 mesh screen. The required amount of anhydrous Emcompress™ was also weighed. The dried granules were transferred to a 16 Quart stainless steel V-blender shell. The Aerosil® 200 VV Pharma and the Anhydrous Emcompress were transferred to the same V-Blender shell. The shell was mounted on to the Yoke of a Patterson-Kelly V-Blender drive unit and blended for 15 minutes. Samples for blend uniformity testing were withdrawn. After successful blend uniformity testing the granulation the required amount of magnesium stearate was weighed out, screened through a 35 mesh screen and transferred to the V-blender shell. The material was blended for 3 minutes and compressed in to tablets using a Korsch EK-O single station tablet press equipped 16.5 mm by 7.5 mm oval shaped tooling. During compression, the following in-process tests were performed, friability, tablet hardness, tablet weight, tablet thickness and disintegration. The target tablet hardness was 780 mg with an acceptable range of 756.6-803.4 mg, the target tablet hardness was 8 Kp with an acceptable range of 5-11 KP. After release testing, the tablets were packaged in 30 count HDPE bottles with pharmaceutics coil, child resistant cap and induction seal liner.

COMPARATIVE EXAMPLE 7

Preparation of Heparin/SNAC Tablets (37,500/250)

Heparin/SNAC tablets having the formulation described in Table 22 were prepared by the procedure described in Comparative Example 6.

TABLE 22

| Component | mg/Tablet (Target) | % of Tablet weight (w/w) | mg/Tablet (acceptable range) |
|---|---|---|---|
| SNAC | 250 | 32.1 | 242.5-257.5 |
| Heparin Sodium, USP (37,500 Units) | ≦267.9 | ≦34.3 | ≦259.8-275.9 |
| Propylene Glycol, USP/EP/JP | 39.0 | 5.00 | 37.8-40.2 |
| Capmul PG8 | 78.0 | 10.00 | 75.7-80.3 |
| Dibasic Calcium Phosphate, Anhydrous, USP/EP (Anhydrous Emcompress) | ≧117.8 | ≧15.1 | ≧114.3-121.3 |
| Colloidal Silicon Dioxide, USP/NF/EP (Aerosil ® 200 VV Pharma) | 15.6 | 2.00 | 15.1-16.1 |
| Povidone K90, USP/EP/JP (Kollidon 90F) | 3.90 | 0.50 | 3.8-4.0 |
| Magnesium Stearate, NF/EP/JP | 7.8 | 1.00 | 7.6-8.0 |
| Total weight | 780.00 | 100.00 | 756.6-803.4 |

COMPARATIVE EXAMPLE 8

Preparation of Liquid Heparin/SNAC 18 mL of the SNAC/heparin solution described in Example 1 of International Publication No. WO 01/34114, which is hereby incorporated by reference, was prepared. The solution contained 90,000 IU of heparin and 2430 mg of SNAC.

EXAMPLE 14

Fifteen human test subjects were administered the formulations described in the chart below, each separated by a 72-hour washout period. For every period, subjects entered a clinic the evening before the administration to begin an 8-hour fast starting at 10 p.m. The formulation was administered in the morning in a fasted state. Table 23 summarizes the periods and the formulations administered.

TABLE 23

| Period | Formulation | Number of Unit Dosages (Tablets, Capsules) | Total Amount of Heparin (IU) | Total Amount of SNAC (mg) |
|---|---|---|---|---|
| A | Comparative Example 5 ("SNAC control dose") | 3 | 0 | 1149 |
| B | Example 3, Table 15C ("capsule 1:1 ratio") | 2 | 75,000 | 500 |
| C | Comparative Example 6 ("tablet 1:2.5 ratio") | 3 | 75,000 | 1149 |
| D | Comparative Example 7 ("tablet 1:1 ratio") | 2 | 75,000 | 500 |
| E | Example 3, Table 15B (capsule 1:2.5 ratio) | 3 | 75,000 | 1149 |
| F | Comparative Example 8 ("liquid reference dose") | 18 ml (Liquid) | 90,000 | 2430 |

For each period, the anti-Factor Xa and IIa activities and aPTT times were measured from blood samples taken at 10 minutes before dosing, upon dosing, and 15, 30, 45, 60, 90, 120, and 480 minutes after dosing. Anti-Factor Xa and IIa activities and aPTT times are indicators of heparin response, and provide a basis to compare the bio-availability of the respective formulations.

APTT and Anti-Factor IIa and Xa results for the 15 subjects were averaged for each sample period, and are shown below.

TABLE 24

Plasma aPTT (seconds)
(Standard Deviation shown in parenthesis)

| Time (minutes) | Treatment Arm | | | | | |
|---|---|---|---|---|---|---|
| | A | B | C | D | E | F |
| −10 | 29.7 (3.0) | 29.4 (2.1) | 30.1 (3.4) | 30.0 (2.4) | 29.8 (2.5) | 29.2 (2.5) |
| 0 | 29.1 (2.5) | 29.1 (2.1) | 29.4 (2.5) | 29.4 (2.2) | 28.9 (2.0) | 29.1 (2.7) |
| 15 | 30.1 (2.9) | 31.6 (2.4) | 37.5 (6.7) | 32.4 (2.7) | 32.7 (6.9) | 41.1 (14.8) |
| 30 | 29.5 (2.70) | 75.1 (54.8) | 51.6 (25.6) | 37.1 (8.4) | 89.1 (63.8) | 52.1 (42.8) |
| 45 | 29.3 (2.6) | 78.4 (56.4) | 60.2 (48.1) | 38.1 (12.9) | 102.6 (72.1) | 53.7 (43.2) |
| 60 | 29.6 (2.4) | 73.0 (57.8) | 51.7 (32.6) | 35.9 (11.4) | 97.0 (72.7) | 51.7 (43.0) |
| 90 | 29.4 (2.4) | 50.8 (31.7) | 41.5 (18.8) | 32.8 (7.5) | 79.7 (66.8) | 44.2 (36.7) |
| 120 | 29.7 (2.3) | 39.5 (16.1) | 34.0 (7.9) | 30.4 (2.6) | 60.9 (50.4) | 36.3 (19.0) |
| 480 | 29.3 (2.6) | 29.2 (2.0) | 29.4 (2.5) | 29.4 (2.5) | 29.3 (2.3) | 29.3 (2.2) |

Figure 16:
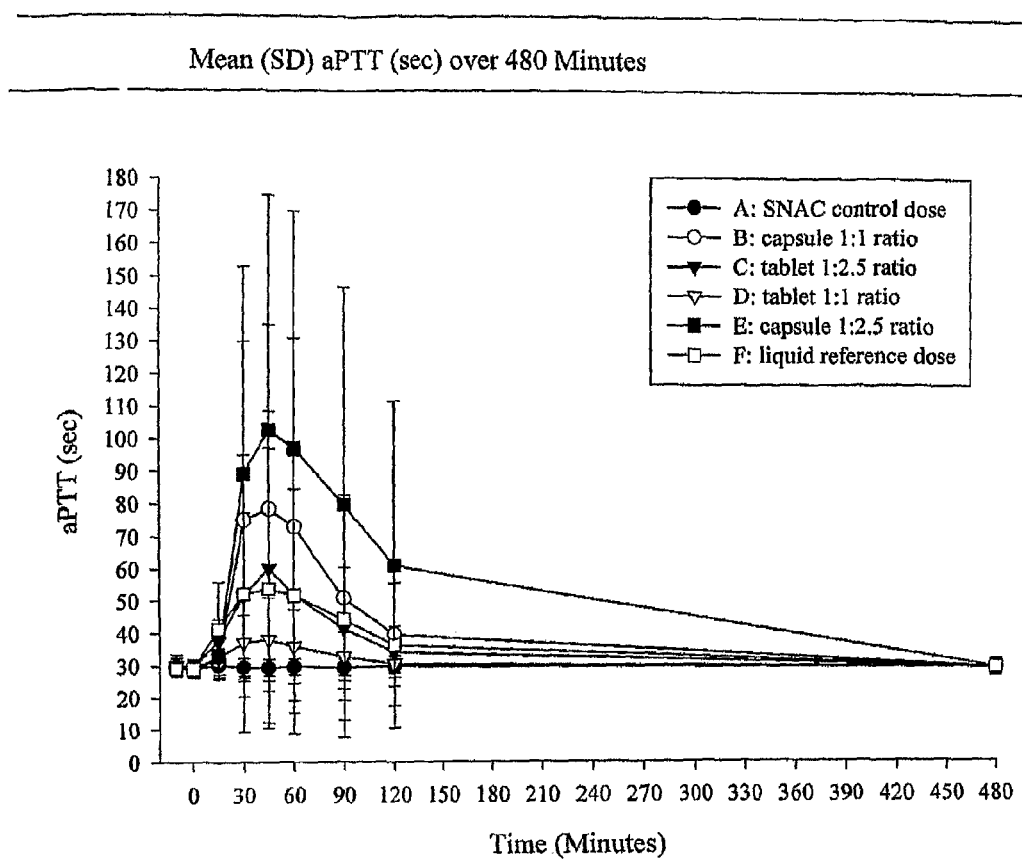
FIGS. 16, 17, 18, 19, and 20 are graphs of aPTT times, Antifactor IIa, Antifactor Xa, and plasma SNAC concentrations versus time for healthy males administered the treatment arms described in Example 14.

These results are shown in FIG. 16.

TABLE 25 aPTT Pharmacodynamic Parameters

| Treatment Arm | Emax, IU/ml (Standard Deviation) | Tmax, hr (Median Range)* | EAUC (0-last), (IU * hr/mL) (Standard Deviation) | EAUC (0-inf), (IU * hr/mL) (Standard Deviation) |
|---|---|---|---|---|
| A | 1.51 (2.30) | 0.75 (0.25-8.00) | 2.634 (3.925) | 2.634 (3.925) |
| B | 56.14 (57.39) | 0.50 (0.50-1.00) | 84.100 (109.584) | 84.100 (109.584) |
| C | 31.76 (47.78) | 0.75 (0.50-1.00) | 42.865 (66.157) | 42.865 (66.157) |
| D | 9.31 (11.70) | 0.50 (0.25-0.75) | 12.088 (15.239) | 12.088 (15.239) |
| E | 80.30 (77.38) | 0.75 (0.25-1.50) | 184.236 (240.894) | 184.236 (240.894) |
| F | 25.89 (42.59) | 0.75 (0.25-8.00) | 55.308 (120.021) | 55.308 (120.021) |

TABLE 26 aPTT Pharmacodynamic Analysis

| Variable | Comparision | Test (LS Means) | Reference (LS Means) | Difference | 90% Confidence Interval |
|---|---|---|---|---|---|
| EAC(0-LAST) (IU * hr/mL) | B-F | 84.100 | 55.308 | 28.793 | −31.3, 88.87 |
| | C-F | 42.865 | 55.308 | −12.44 | −72.5, 47.64 |
| | D-F | 12.088 | 55.308 | −43.22 | −103, 16.86 |
| | E-F | 184.236 | 55.308 | 128.93 | 68.85, 189.0 |
| | E-B | 184.236 | 84.100 | 100.14 | 40.06, 160.2 |
| | C-A | 42.865 | 2.634 | 40.231 | −19.8, 100.3 |
| | C-D | 42.865 | 12.088 | 30.777 | −29.3, 90.85 |
| | B-D | 84.100 | 12.088 | 72.012 | 11.93, 132.1 |
| | E-A | 184.236 | 2.634 | 181.60 | 121.5, 241.7 |
| | E-C | 184.236 | 42.865 | 141.37 | 81.29, 201.4 |
| Emax (IU/ml) | B-F | 56.143 | 25.887 | 30.257 | 8.011, 52.50 |
| | C-F | 31.757 | 25.887 | 5.870 | −16.4, 28.12 |
| | D-F | 9.310 | 25.887 | −16.58 | −38.8, 5.669 |
| | E-F | 80.303 | 25.887 | 54.417 | 32.17, 76.66 |
| | E-B | 80.303 | 56.143 | 24.160 | 1.915, 46.41 |
| | C-A | 31.757 | 1.513 | 30.243 | 7.998, 52.49 |
| | C-D | 31.757 | 9.310 | 22.447 | 0.201, 44.69 |
| | B-D | 56.143 | 9.310 | 46.833 | 24.59, 69.08 |
| | E-A | 80.303 | 1.513 | 78.790 | 56.54, 101.0 |
| | E-C | 80.303 | 31.757 | 48.547 | 26.30, 70.79 |

As shown in Table 24 and FIG. 16, the longest aPTT occurred in the following descending order: soft gelatin capsule 1:2.5 ratio (Treatment Arm E), soft gelatin capsule 1:1 ratio (Treatment Arm B), tablet 1:2.5 ratio (Treatment Arm C), liquid SNAC/Heparin dose (Treatment Arm F), tablet 1:1 ratio (Treatment Arm D), and the SNAC control dose (Treatment Arm A). The increase in aPTT was approximately 2.4 times higher with the soft gelatin capsule 1:2.5 ratio than with the 1:2.5 ratio tablet and approximately 3 times higher than with the liquid SNAC/heparin dose.

Shown in Table 26, based on a 90% confidence interval around the difference for aPTT results under a Least Squares Means Analysis, the formulation comparisons showing statistically significant differences for EAUC(O-last) were the soft gelatin capsule 1:2.5 ratio (Treatment Arm E) to SNAC control dose (Treatment Arm A), capsule 1:2.5 ratio (Treatment Arm E) to liquid reference dose (Treatment Arm F), capsule 1:2.5 ratio (Treatment Arm E) to capsule 1:1 ratio (Treatment Arm B), capsule 1:2.5 ratio (Treatment Arm E) to tablet 1:2.5 ratio (Treatment Arm C) and capsule 1:1 ratio (Treatment Arm B) to tablet 1:1 ratio (Treatment Arm D). The formulation comparisons showing statistically significant differences for Emax were as follows: capsule and tablet 1:2.5 ratios (Treatment Arms E and C) to SNAC control dose (Treatment Arm A), capsule 1:2.5 ratio and 1:1 ratios (E and B) to liquid reference dose (Treatment Arm F), capsule 1:2.5 ratio (E) to capsule 1:1 ratio (Treatment Arm B), capsule 1:2.5 ratio (E) to tablet 1:2.5 ratio (Treatment Arm C), capsule 1:1 ratio (Treatment Arm B) to tablet 1:1 ratio (Treatment Arm D), and tablet 1:2.5 ratio (Treatment Arm C) to tablet 1:1 ratio (Treatment Arm D).

TABLE 27

Anti-Factor IIa Plasma Concentrations (IU/mL)
(Standard Deviation shown in parenthesis)

| Time (minutes) | Treatment Arm | | | | | |
|---|---|---|---|---|---|---|
| | A | B | C | D | E | F |
| −10 | BLQ* | BLQ | BLQ | BLQ | BLQ | BLQ |
| 0 | BLQ | BLQ | BLQ | BLQ | BLQ | BLQ |
| 15 | BLQ | 0.07 | 0.12 | 0.08 | 0.07 | 0.11 |
| | | (0.05) | (0.04) | (0.05) | (0.06) | (0.08) |
| 30 | BLQ | 0.30 | 0.20 | 0.12 | 0.33 | 0.15 |
| | | (0.20) | (0.11) | (0.08) | (0.23) | (0.16) |
| 45 | BLQ | 0.33 | 0.21 | 0.12 | 0.40 | 0.16 |
| | | (0.22) | (0.13) | (0.10) | (0.33) | (0.17) |
| 60 | BLQ | 0.29 | 0.20 | 0.10 | 0.39 | 0.15 |
| | | (0.21) | (0.13) | (0.11) | (0.34) | (0.18) |

TABLE 27-continued

Anti-Factor IIa Plasma Concentrations (IU/mL)
(Standard Deviation shown in parenthesis)

| Time (minutes) | Treatment Arm | | | | | |
|---|---|---|---|---|---|---|
| | A | B | C | D | E | F |
| 90 | BLQ | 0.20 | 0.14 | BLQ | 0.31 | 0.11 |
| | | (0.16) | (0.10) | | (0.31) | (0.15) |
| 120 | BLQ | 0.14 | 0.10 | BLQ | 0.23 | 0.08 |
| | | (0.13) | (0.07) | | (0.24) | (0.11) |
| 480 | BLQ | BLQ | BLQ | BLQ | BLQ | BLQ |

*Mean values below 0.05 IU/mL are denoted as below the limit of quantification (BLQ). For statistical purposes, individual values below the limit of quantification (BLQ) were set to 0.025 IU/ml.

Figure 17:
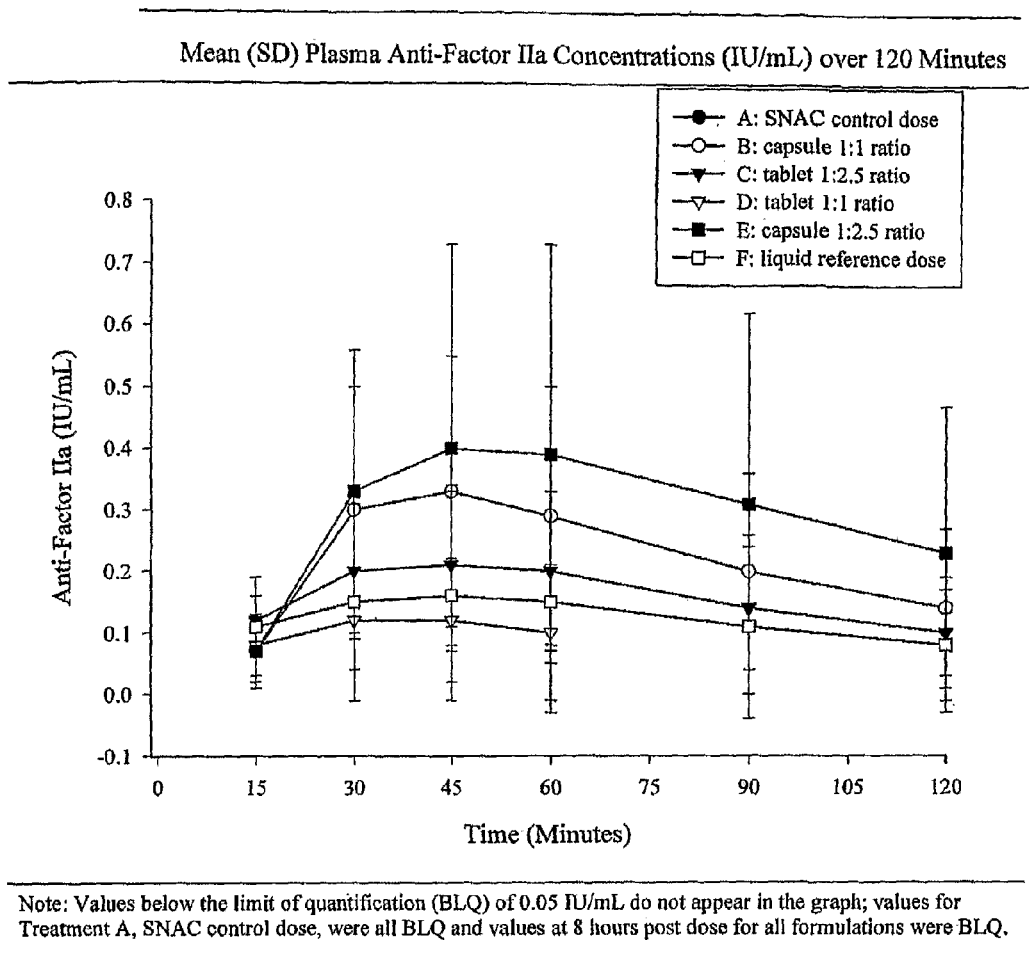

The above results over 120 minutes are shown in FIG. 17.

TABLE 28

Plasma anti-Factor IIa Pharmacodynamic Parameters

| Treatment Arm | Emax, IU/ml (Standard Deviation) | Tmax, hr (Median Range)* | EAUC (0-last), (IU * hr/mL) (Standard Deviation) | EAUC (0-inf), (IU * hr/mL) (Standard Deviation) |
|---|---|---|---|---|
| A | 0.04 | 0.50 | 0.262 | 0.324 |
| | (0.04) | (0.25-8.00) | (0.261) | (0.236) |
| B | 0.36 | 0.75 | 0.714 | 0.905 |
| | 0.22 | (0.50-1.00) | (0.771) | (0.786) |
| C | 0.22 | 0.75 | 0.566 | 0.715 |
| | 0.13 | (0.50-1.00) | (0.391) | (0.411) |
| D | 0.13 | 0.50 | 0.369 | 0.418 |
| | 0.10 | (0.25-1.00) | (0.369) | (0.364) |
| E | 0.42 | 0.75 | 1.116 | 1.511 |
| | 0.34 | (0.50-1.00) | (1.167) | (1.214) |
| F | 0.16 | 0.50 | 0.349 | 0.545 |
| | 0.18 | (0.25-1.00) | (0.301) | (0.636) |

TABLE 29

Anti-Factor IIa Pharmacodynamic Analysis

| Variable | Comparision | Test (LS Means) | Reference (LS Means) | Difference | 90% Confidence Interval |
|---|---|---|---|---|---|
| EAC (0-LAST) (IU * hr/mL) | B-F | 0.714 | 0.357 | 0.357 | −0.029, 0.744 |
| | C-F | 0.571 | 0.357 | 0.214 | −0.180, 0.608 |
| | D-F | 0.363 | 0.357 | 0.006 | −0.403, 0.414 |
| | E-F | 1.112 | 0.357 | 0.755 | 0.353, 1.157 |
| | E-B | 1.112 | 0.714 | 0.398 | 0.011, 0.784 |
| | C-A | 0.571 | 0.447 | 0.124 | −0.337, 0.585 |
| | C-D | 0.571 | 0.363 | 0.208 | −0.196, 0.613 |
| | B-D | 0.714 | 0.363 | 0.352 | −0.045, 0.748 |
| | E-A | 1.112 | 0.447 | 0.665 | 0.195, 1.135 |
| | E-C | 1.112 | 0.571 | 0.541 | 0.149, 0.933 |
| Emax (IU/ml) | B-F | 0.357 | 0.163 | 0.194 | 0.104, 0.284 |
| | C-F | 0.220 | 0.163 | 0.057 | −0.033, 0.146 |
| | D-F | 0.128 | 0.163 | −0.035 | −0.125, 0.054 |
| | E-F | 0.416 | 0.163 | 0.253 | 0.163, 0.342 |
| | E-B | 0.416 | 0.357 | 0.059 | −0.031, 0.148 |
| | C-A | 0.220 | 0.043 | 0.177 | 0.088, 0.267 |
| | C-D | 0.220 | 0.128 | 0.092 | 0.002, 0.182 |
| | B-D | 0.357 | 0.128 | 0.229 | 0.140, 0.319 |
| | E-A | 0.416 | 0.043 | 0.373 | 0.284, 0.463 |
| | E-C | 0.416 | 0.220 | 0.196 | 0.106, 0.286 |

As shown in Table 27 and FIG. 17, the highest mean concentrations of anti-factor IIa occurred in the following descending order: soft gelatin capsule 1:2.5 ratio (Treatment Arm E), soft gelatin capsule 1:1 ratio (Treatment Arm B), tablet 1:2.5 ratio (Treatment Arm C), liquid SNAC/Heparin dose (Treatment Arm F), tablet 1:1 ratio (Treatment Arm D), and the SNAC control dose (Treatment Arm A). The increase in both anti-factor IIa and anti-factor Xa mean concentrations was approximately 2 times higher with the soft gelatin capsule 1.2.5 ratio than with the 1:2.5 tablet and approximately 2.5 times higher than with the liquid references dose.

Shown in Table 29, based on a 90% confidence interval around the difference for antifactor IIa results under a Least Squares Means Analysis, the formulation showing statistically significant differences for EAUC(O-last) were the capsule 1:2.5 ratio (Treatment Arm E) to the SNAC control dose (Treatment Arm A), the liquid reference dose (F and the tablet 1:2.5 ratio (Treatment Arm C). The formulation comparisons showing statistically significant differences for Emax were as follows: capsule and tablet 1:2.5 ratio (Treatment Arms E and C) to SNAC control dose (Treatment Arm A), capsule 1:2.5 and 1:1 ratios (Treatment Arms E and B) to liquid reference dose (Treatment arm F), capsule 1:2.5 ratio (Treatment Arm E) to tablet 1:2.5 ratio (Treatment Arm C) capsule 1:1 ratio (Treatment Arm B) to tablet 1:1 ratio (Treatment Arm D) and tablet 1:2.5 ratio (Treatment Arm C) to tablet 1:1 ratio (Treatment Arm D).

TABLE 30

Anti-Factor Xa Plasma Concentrations (IU/mL)
(Standard Deviation shown in parenthesis)

| Time (minutes) | Treatment Arm | | | | | |
|---|---|---|---|---|---|---|
| | A | B | C | D | E | F |
| −10 | BLQ* | BLQ | BLQ | BLQ | BLQ | BLQ |
| 0 | BLQ | BLQ | BLQ | BLQ | BLQ | BLQ |
| 15 | BLQ | BLQ | 0.11 (0.07) | 0.06 (0.04) | 0.07 (0.04) | 0.11 (0.08) |
| 30 | BLQ | 0.34 (0.28) | 0.19 (0.14) | 0.10 (0.07) | 0.31 (0.22) | 0.16 (0.16) |
| 45 | BLQ | 0.32 (0.22) | 0.21 (0.18) | 0.10 (0.10) | 0.42 (0.33) | 0.16 (0.17) |
| 60 | BLQ | 0.28 (0.20) | 0.21 (0.18) | BLQ | 0.42 (0.36) | 0.16 (0.19) |
| 90 | BLQ | 0.17 (0.14) | 0.13 (0.12) | BLQ | 0.31 (0.31) | 0.12 (0.17) |
| 120 | BLQ | 0.11 (0.11) | 0.09 (0.08) | BLQ | 0.23 (0.24) | 0.09 (0.13) |
| 480 | BLQ | BLQ | BLQ | BLQ | BLQ | BLQ |

*Mean values below 0.05 IU/mL are denoted as below the limit of quantification (BLQ). For statistical purposes, individual values below the limit of quantification (BLQ) were set to 0.025 IU/ml.

Figure 18:
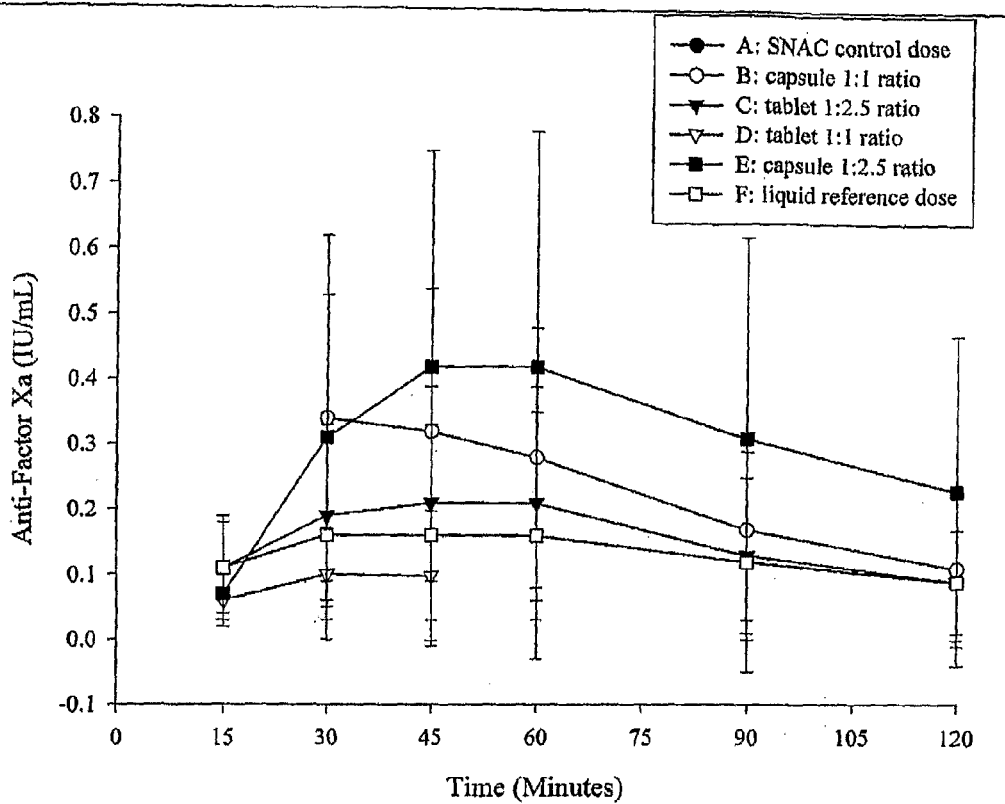

These results are shown in FIG. 18.

TABLE 31

Plasma anti-Factor Xa Pharmacodynamic Parameters

| Treatment Arm | Emax, IU/ml (Standard Deviation) | Tmax, hr (Median range) | EAUC (0-last), (IU * hr/mL) (Standard Deviation) | EAUC (0-inf), (IU * hr/mL) (Standard Deviation) |
|---|---|---|---|---|
| A | 0.00 0.02 | 2.00 (2.00-2.00) | 0.048 | 0.258 |
| B | 0.38 0.30 | 0.50 (0.50-1.00) | 0.383 (0.295) | 0.689 (0.626) |
| C | 0.22 0.18 | 0.75 (0.25-1.00) | 0.296 (0.252) | 0.552 (0.525) |
| D | 0.11 0.10 | 0.50 (0.25-1.00) | 1.162 (0.145) | 0.297 (0.271) |
| E | 0.44 0.36 | 0.75 (0.50-1.00) | 0.876 (0.729) | 1.563 (1.198) |
| F | 0.17 0.20 | 0.75 (0.25-1.00) | 0.377 (0.394) | 0.621 (0.758) |

TABLE 32

Anti-Factor Xa Pharmacodynamic Analysis

| Variable | Comparison | Test (LS Means) | Reference (LS Means) | Difference | 90% Confidence Interval |
|---|---|---|---|---|---|
| EAC (0-LAST) (IU * hr/mL) | B-F | 0.383 | 0.338 | 0.045 | −0.148, 0.238 |
| | C-F | 0.274 | 0.338 | −0.064 | −0.261, 0.133 |
| | D-F | 0.102 | 0.338 | −0.236 | −0.449, −0.024 |
| | E-F | 0.877 | 0.338 | 0.538 | 0.334, 0.743 |
| | E-B | 0.877 | 0.338 | 0.493 | 0.301, 0.686 |
| | C-A | 0.274 | 0.197 | 0.077 | −0.469, 0.623 |
| | C-D | 0.274 | 0.102 | 0.172 | −0.029, 0.373 |
| | B-D | 0.383 | 0.102 | 0.281 | 0.083, 0.480 |
| | E-A | 0.877 | 0.197 | 0.680 | 0.131, 1.228 |
| | E-C | 0.877 | 0.274 | 0.603 | 0.406, 0.800 |
| Emax (IU/ml) | B-F | 0.377 | 0.175 | 0.202 | 0.098, 0.306 |
| | C-F | 0.224 | 0.175 | 0.049 | −0.055, 0.153 |
| | D-F | 0.106 | 0.175 | −0.069 | −0.173, 0.035 |
| | E-F | 0.443 | 0.175 | 0.268 | 0.164, 0.372 |
| | E-B | 0.443 | 0.377 | 0.066 | −0.038, 0.170 |
| | C-A | 0.224 | 0.005 | 0.219 | 0.115, 0.323 |
| | C-D | 0.224 | 0.106 | 0.118 | 0.014, 0.222 |
| | B-D | 0.377 | 0.106 | 0.271 | 0.167, 0.375 |
| | E-A | 0.443 | 0.005 | 0.438 | 0.334, 0.542 |
| | E-C | 0.443 | 0.224 | 0.219 | 0.115, 0.323 |

As shown in Table 30 and FIG. 18, the highest mean concentrations of anti-factor Xa occurred in the following descending order: soft gelatin capsule 1:2.5 ratio (Treatment Arm E), soft gelatin capsule 1:1 ratio (Treatment Arm B), tablet 1:2.5 ratio (Treatment Arm C), liquid SNAC/Heparin dose (Treatment Arm F), tablet 1:1 ratio (Treatment Arm D), and the SNAC control dose (Treatment Arm A). The increase in anti-factor Xa mean concentrations was approximately 2 times higher with the soft gelatin capsule 1.2.5 ratio than with the 1:2.5 tablet and approximately 2.5 times higher than with the liquid references dose.

Based on a 90% confidence interval around the difference for anti-factor Xa results under a Least Squares Means analysis, the formulation comparisons showing statistically significant differences for EAUC(O-last), the formulation comparisons showing statistically significant differences where soft gelatin capsule 1:2.5 ratio (E) to SNAC control dose (A), capsule 1:2.5 ratio (E) to the liquid reference does (F), capsule 1:2.5 ratio (E) to capsule 1:1 ratio (B), tablet 1:2.5 ratio (C) to tablet 1:1 ratio (D), capsule 1:2.5 ratio (E) to the tablet 1:2.5 ratio (C), and capsule 1:1 ratio (B) to tablet 1:1 ratio (D). The formulation comparisons showing statistically significant differences for Emax were as follows: soft gelatin capsule 1:2.5 ratio (E) and tablet 1:2.5 ratio (C) to SNAC control dose (A), capsule 1:2.5 and 1:1 ratios (E and B) to liquid reference dose (F), tablet 1:2.5 ratio (C) to tablet 1:1 ratio (D), capsule 1:2.5 ratio (E) to tablet 1:2.5 ratio (C), and capsule 1:1 ratio (B) to tablet 1:1 ratio (D).

TABLE 33

Plasma SNAC Pharmacokinetic Parameters

| Treatment Arm | Cmax, ng/ml (SD) | Tmax, hr (SD) | AUC (0-last), ng * hr/ml (SD) | AUC (0-inf), ng * hr/ml (SD) | CL/F, L/hr (SD) | KeL ($\lambda z$) (hr) | $t_{1/2}$, hr (SD) | VZ/F (L) (SD) |
|---|---|---|---|---|---|---|---|---|
| A | 5573.1 (2293.9) | 0.50 (0.25-2.00) | 5239.74 (1615.83) | 5448.01 (1604.81) | 227.3 (61.2) | 0.4903 (0.1395) | 1.50 (0.33) | 497.5 (207.0) |
| B | 3041.7 (1105.7) | 0.50 (0.25-1.00) | 2261.17 (563.76) | 2293.28 (561.78) | 230.0 (55.3) | 0.8311 (0.7110) | 1.21 (0.52) | 417.0 (229.1) |
| C | 6463.3 (4252.6) | 0.25 (0.25-1.00) | 5887.55 (2079.82) | 5977.66 (2056.15) | 206.4 (46.9) | 0.4820 (0.1371) | 1.55 (0.45) | 475.2 (213.6) |
| D | 2481.3 (1104.0) | 0.25 (0.25-0.50) | 1967.73 (421.50) | 2002.92 (418.81) | 260.1 (55.6) | 0.7755 (0.7636) | 1.35 (0.61) | 519.2 (311.4) |
| E | 6539.7 (3804.8) | 0.50 (0.25-1.00) | 5913.98 (1641.69) | 5954.53 (1633.97) | 204.0 (44.6) | 0.5953 (0.0861) | 1.19 (0.17) | 351.1 (95.1) |
| F | 14254.0 (7153.3) | 0.25 (0.25-1.00) | 13052.1 (4554.21) | 13162.6 (4541.42) | 205.5 (67.7) | 0.6112 (0.1258) | 1.19 (0.29) | 361.1 (181.2) |

Figure 19:
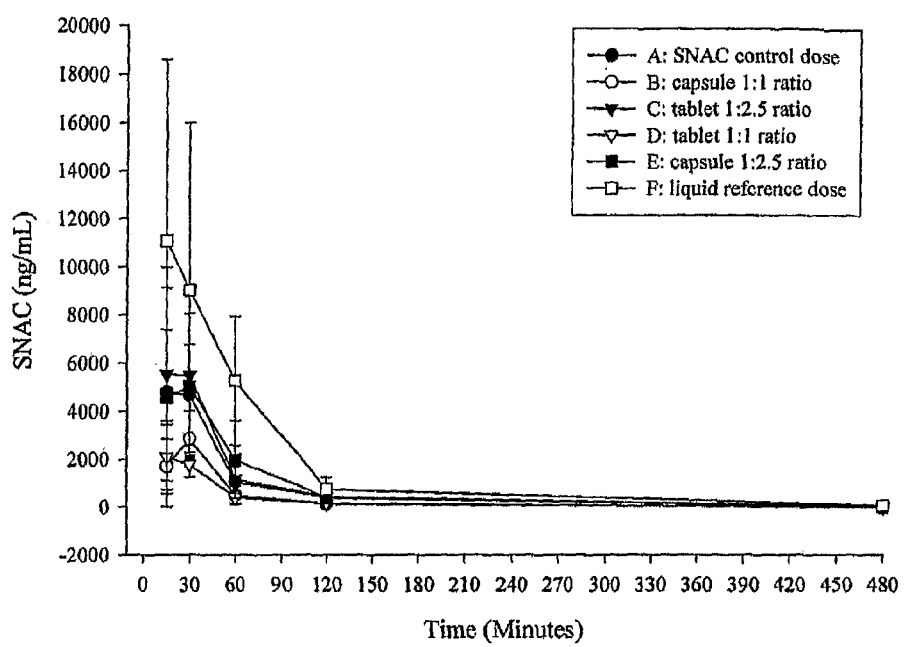
Figure 20:
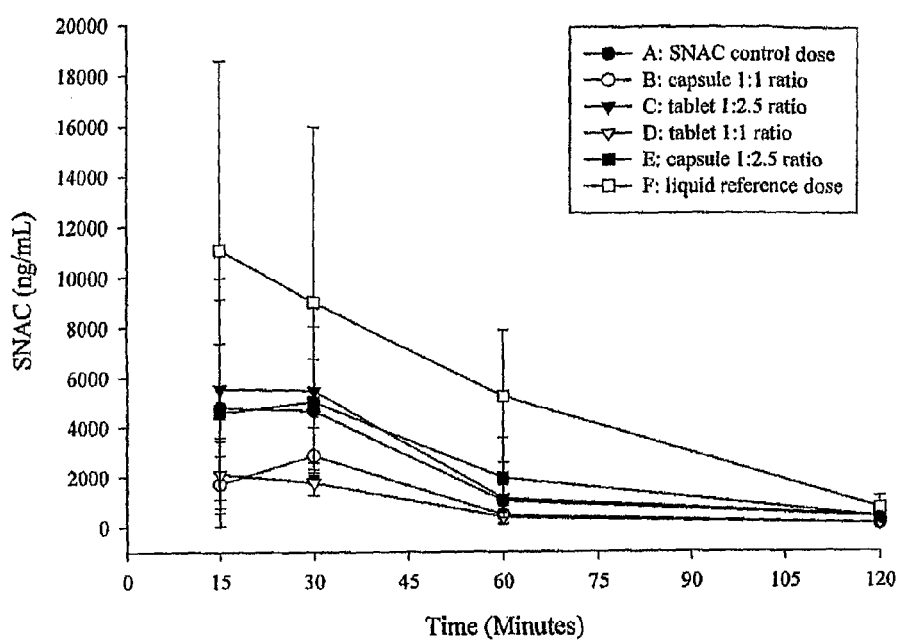

Plasma SNAC concentrations up to 8 hours and 2 hours after administration are shown in FIGS. 19 and 20, respectively In each marker of anti-coagulant activity, capsule formulations produced greater anti-coagulant effect than a similar dose in a tablet formation or the liquid reference dose (90,000 units/2430 mg). In capsule formulations, mean maximum anti-factor Xa concentrations were relatively similar in the 1:1 and 1:2.5 ratio dose groups, at 0.38 and 0.44 IU/mL, respectively. However EAUC values in the same dose groups were 0.38 and 0.88 IU*hr/mL, respectively, illustrating the longer duration of effect observed in the 1:2.5 ratio dose group.

The soft gelatin capsule produced 2 to 3 fold higher Emax values than the tablet and liquid formulations No inherent anti-coagulation activity was demonstrated by the SNAC control dose. All treatments were well tolerated by the subjects.

EXAMPLE 15

Soft gelatin capsules having the formulations shown in Tables 35a and 35b were prepared by the process described in Example 3, except as indicated below:

TABLE 35a

| Component | mg/capsule | % of capsule weight |
|---|---|---|
| SNAC | 250.00 | 21.37 |
| Heparin Sodium, USP (15,000 units) | 267.18 | 22.89 |
| Polyethylene Glycol 300, NF (PEG 300) | 402.70 | 34.42 |
| Capmul ® PG8 | 164.00 | 14.02 |
| Purified Water, USP | 81.99 | 7.00 |
| Soybean Oil, USP Super Refined | 1.17 | 0.10 |
| Polysorbate 80 | 2.34 | 0.24 |
| Total weight | 1,170.00 | 100 |

TABLE 35b

| Components | mg/capsule | % of capsule weight |
|---|---|---|
| SNAC | 250.0 | 21.37 |
| Heparin Sodium, USP (25,000 Units) | 267.86 | 22.89 |
| Polyethylene Glycol 300, NF (PEG 300) | 405.00 | 34.62 |
| Capmul ® PG8 | 164.00 | 14.02 |
| Purified Water, USP | 81.99 | 7.00 |
| Soybean Oil, USP Super Refined | 1.15 | 0.10 |
| Total weight | 1,170.00 | 100 |

For the formulation described in Table 35a, Polysorbate 80 was added along with Propylene glycol monocaprylate, purified water, and soybean oil in the stainless steal container, and heparin that was milled through a bead mill with a #140 Mesh screen yielding a heparin particle size of less than 100 microns. Also, the aggregate suspension in the formulation described in Table 35a was milled through a MZ80/A Fryma Colloid mill until the particle size is <180 microns.

To prepare the formulation in table 35b, Polysorbate 80 was not added with Polyethylene glycol (PEG) 300, Propylene glycol monocaprylate (Capmul® PG8), purified water, and soybean oil. Also, the heparin was milled with a # 80 mesh screen and the suspension was not milled through the colloid mill. The particle size comparison of the formulation of table 35a and table 35b set forth below in table 36

TABLE 36

Particle Size data for Formulations in Tables 35a and 35b

| Particle | Formulation in Table 35a | Formulation in Table 35b |
|---|---|---|
| Milled Heparin Suspension (Based on the Grind Gauge) | <100 microns Target: <=180 microns 80 microns (initial aggregate) | <180 microns Target: <=180 microns 200 microns (initial aggregate) 160 microns (final aggregate) |

EXAMPLE 16

The disintegration of the soft gelatin capsules prepared as in Example 15 were determined in three different media, i.e. purified water, 0.1N HCl at pH 1.2 (Simulated Gastric Fluid w/o pepsin) and 6.8 phosphate buffer (simulated intestinal fluid @ pH 6.8 (w/o pancreatin) at 37+/−0.5° C. in a Vankel Disintegration Apparatus model # 35-1000 (Cary, N.C.) equipped with a Model 65-2000 Heater Circulator The results are shown below.

TABLE 37

Disintegration Data

| Disintegration Media | Formulation in Table 35a | Formulation in Table 35b |
|---|---|---|
| Simulated Gastric Fluid @ pH 1.2 (w/o pepsin) | 6 minutes and 15 seconds | 4 mins and 31 seconds |
| Simulated Intestinal Fluid @ pH 6.8 (w/o pancreatin) | Not Determined | 5 mins and 14 seconds |
| Purified Water | Not Determined | 4 mins and 57 seconds |

Figure 21:
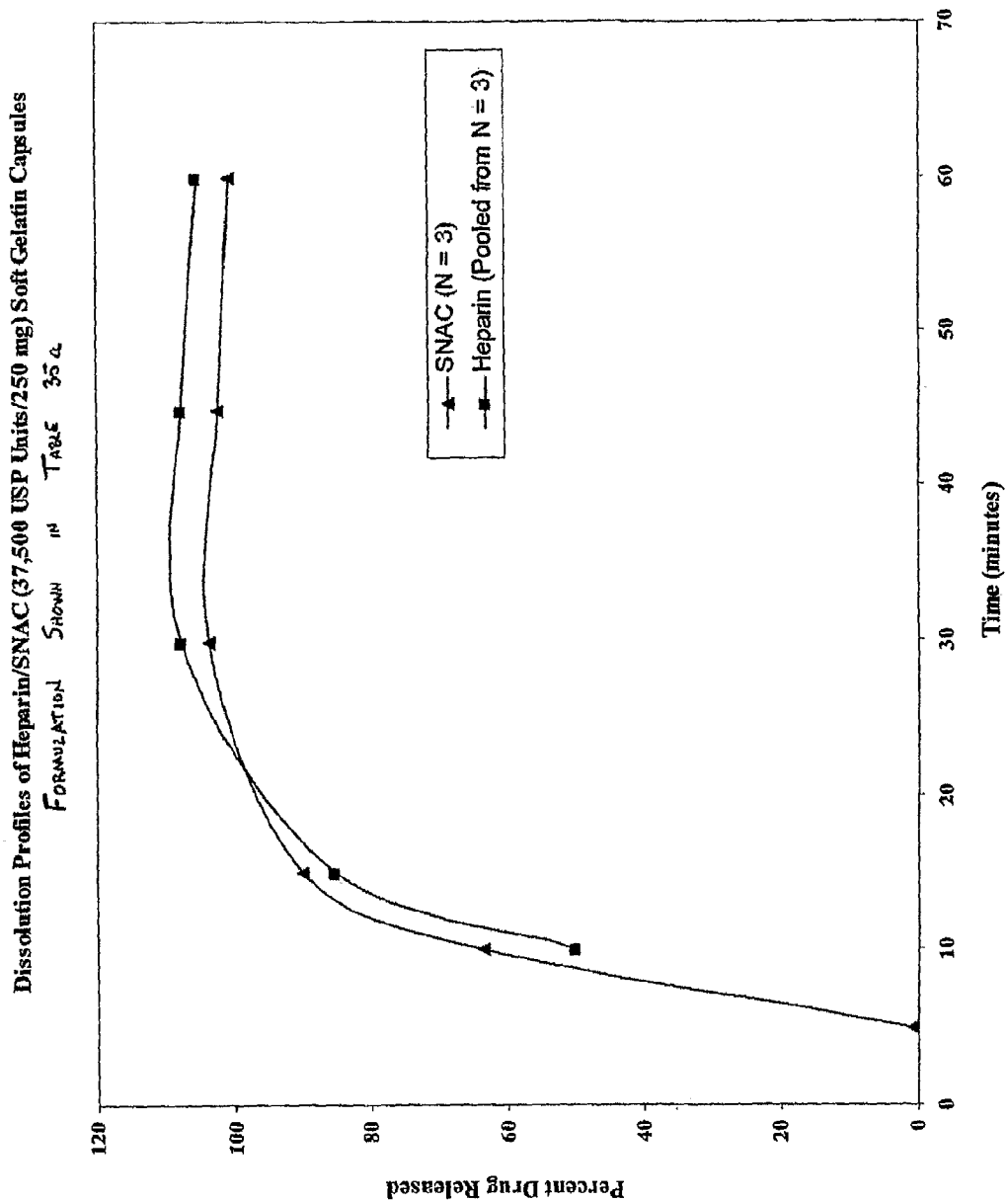
FIGS. 21 and 22 is a dissolution profile of the formulation set forth in Tables 35a and 35b, and prepared as described in Example 15.
Figure 22:
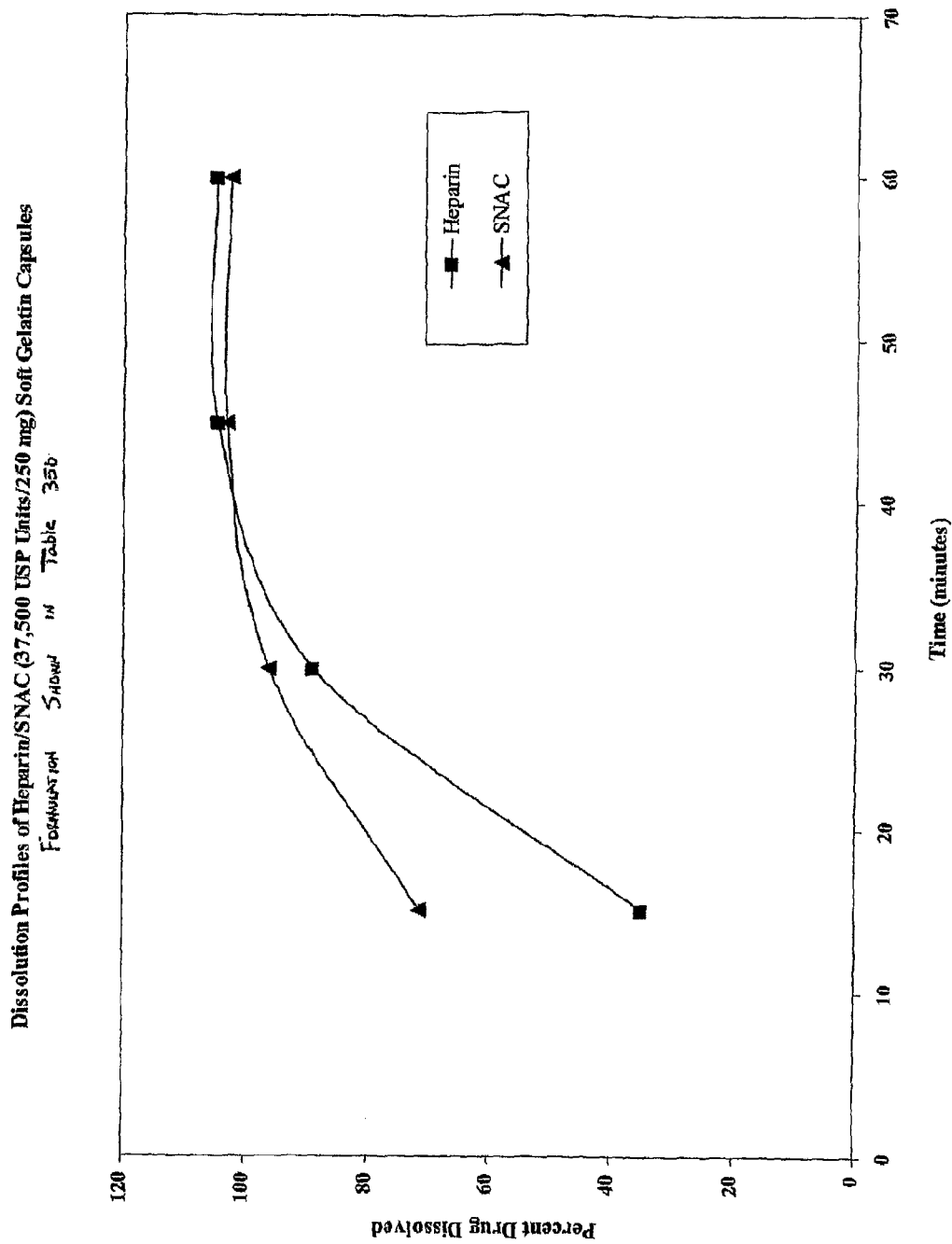

Dissolution profiles for the above two formulations were obtained in a phosphate buffer having pH of 6.8 37+/−0.5° C. (Simulated Intestinal Fluid) in the above Vankel Disintegration Apparatus at 75 RPM. The results for the Formulation shown in Table 35a is shown in FIG. 21. The result for the Formulation shown in Table 35b is shown in FIG. 22.

EXAMPLE 17

Soft gelatin capsules having the formulations shown in Table 35a and 35b, prepared as described in Example 15 were administered to 4 Beagles weighing about 8 kg. The dogs were fasted at least 8 hours prior to dosing and food was returned about 4 hours after dosing of the solid. Each dosage form was delivered to the rear of the mouth by hand. After release of the dosage form, 5 ml of reverse osmosis water was administered into the oral cavity to facilitate swallowing. Following delivery, the oral cavity was inspected to ensure that the solid was swallowed. The study was conducted in cross-over fashion with a one week wash-out period.

Antifactor Xa was measured over a period of about 240 minutes after administration from plasma samples obtained from the jugular, cephalic, or saphenous veins. Sampling points are rotated.

Figure 23:
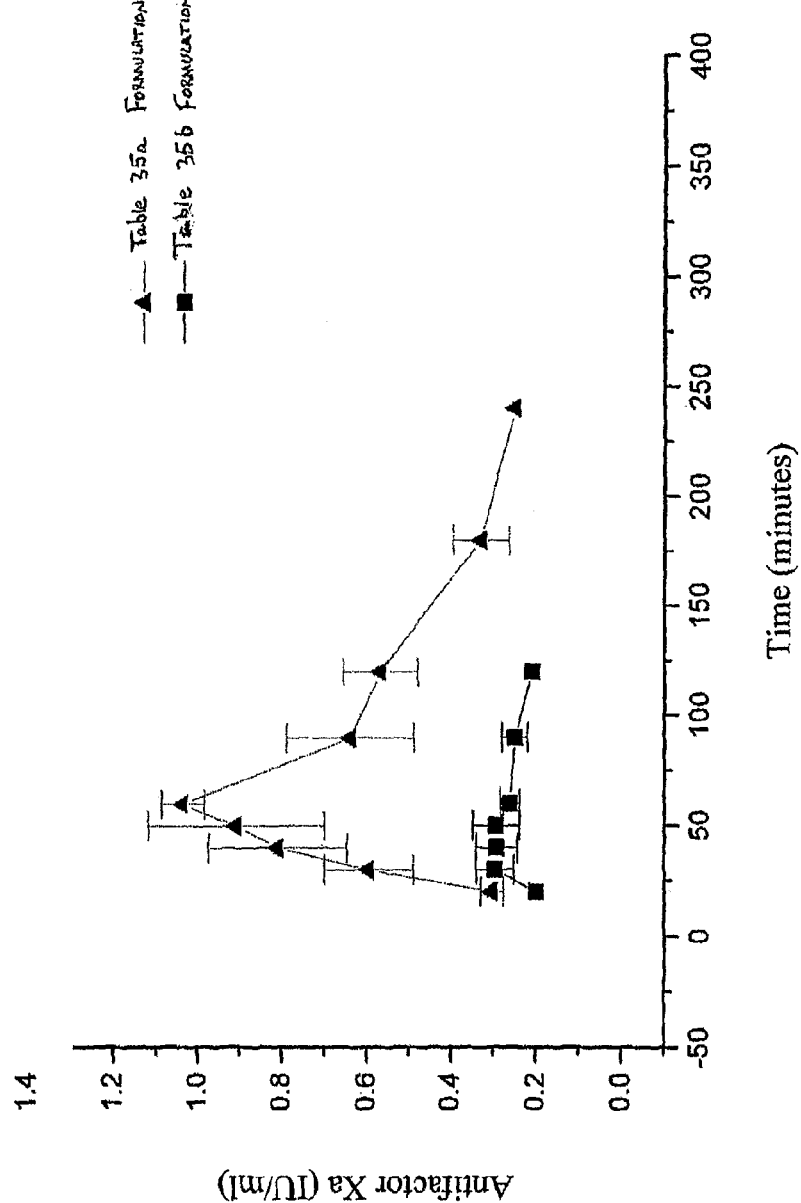
FIG. 23 is a graph of Antifactor Xa activity versus time for beagles administered the formulations described in Tables 35a and 35b, and prepared as described in Example 15, administered as described in Example 17.

The results were averaged and are shown in are shown in FIG. 23.

EXAMPLE 18

Soft gelatin capsule having the formulation shown in Table 35a and 35b, prepared as described in Example 15 were administered to 4 Rhesus monkeys (1 capsule/monkey) by the following procedure.

Rhesus monkeys weighing between 5.3 and 6.9 kg were fasted overnight before the experiments and food was returned about 6 hours after dosing of the solid. Each dosage form was delivered to the rear of the mouth using a dosing tune. After release of the dosage form, 5 ml of reverse osmosis water was administered into the oral cavity to facilitate swallowing. Following delivery, the oral cavity was inspected to ensure that the solid was swallowed. The study was conducted in crossover fashion with a one week washout period.

Antifactor Xa was measured over a period of about 400 minutes after administration.

Figure 24:
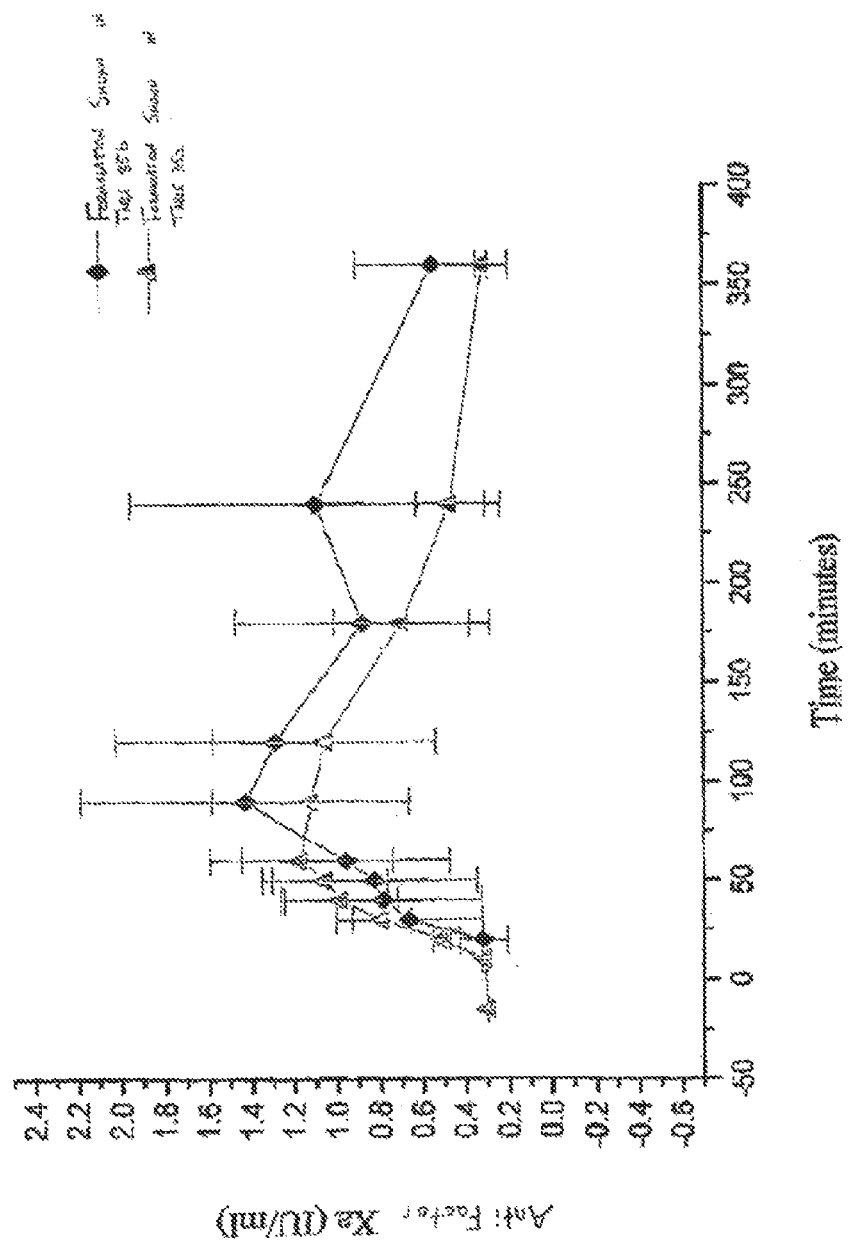
FIG. 24 is a graph of Antifactor Xa activity versus time for Rhesus monkeys administered the formulations described in Tables 35a and 35b, and prepared as described in Example 15, administered as described in Example 18.

The results were averaged and are shown in FIG. 24.

EXAMPLE 19

Soft gelatin capsules having the formulations shown in Table 35a and 35b, prepared as described in Example 15, were administered to 4 beagles in a cross-over design study with a one week washout period. The dogs were fasted overnight before the experiment and food was returned about 2 hours after dosing the solid. Each dosage form was delivered to the rear of the mouth using a pill gun. After release of the dosage form, 5 ml of reverse osmosis water was administered into the oral cavity to facilitate swallowing. Following delivery, the oral cavity was inspected to ensure that the solid was swallowed.

Antifactor Xa activity was measured over a period of about 360 minutes. The results are set forth in the table 38 below:

TABLE 38

Antifactor Xa Pharmacokinetic Results

| Statistics | Formulation | Dog | $C_{max}$ (IU/mL) | $t_{max}$ (min) | $AUC_{last}$ |
|---|---|---|---|---|---|
|  | Table 35a | A | 1.03 | 50.0 | 104 |
|  | Table 35a | B | 1.08 | 50.0 | 97.5 |
|  | Table 35a | C | 0.340 | 40.0 | 20.8 |
|  | Table 35a | D | 1.21 | 50.0 | 143 |
| Mean | Table 35a |  | 0.915 | 47.5 | 91.2 |
| SD | Table 35a |  | 0.391 | 5.00 | 51.0 |
| % CV | Table 35a |  | 42.7 | 10.5 | 56.0 |
|  | Table 35b | A | 0.280 | 50.0 | 8.80 |
|  | Table 35b | B | 0.490 | 50.0 | 32.8 |
|  | Table 35b | C | 0.260 | 60.0 | 7.70 |
|  | Table 35b | D | 0.370 | 30.0 | 28.9 |
| Mean | Table 35b |  | 0.350 | 47.5 | 19.5 |
| SD | Table 35b |  | 0.105 | 12.6 | 13.1 |
| % CV | Table 35b |  | 30.0 | 26.5 | 67.2 |

Figure 25:
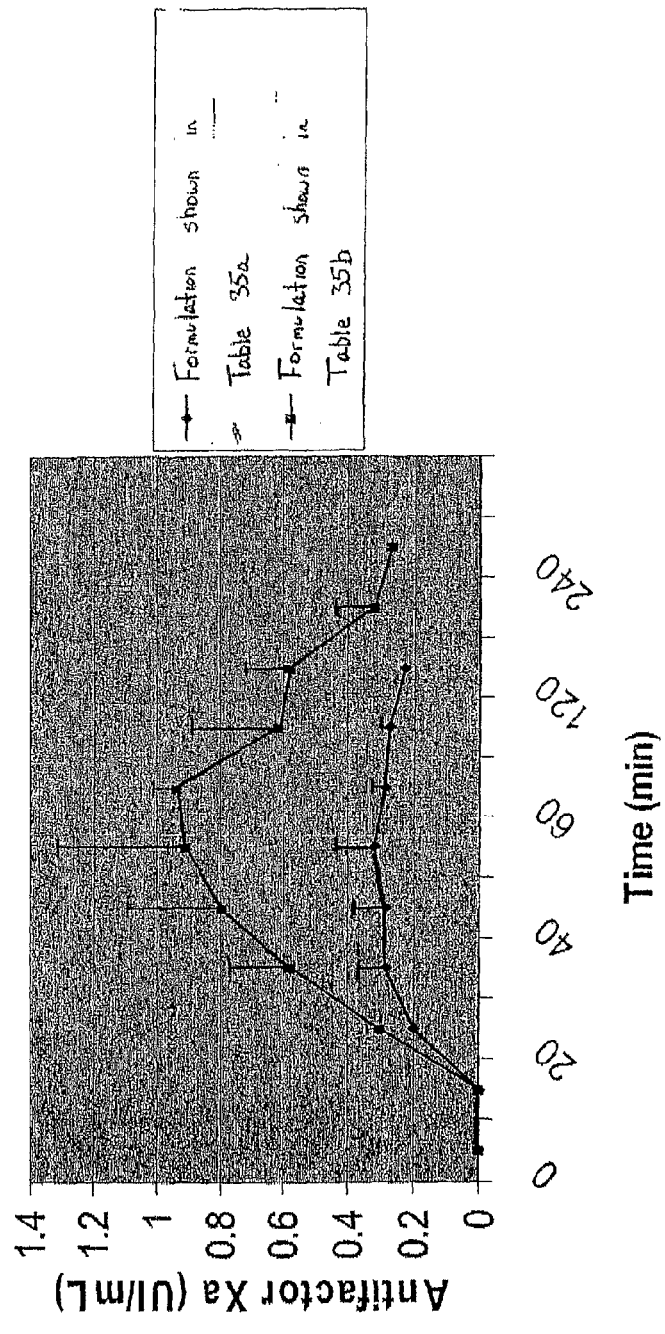
FIG. 25 is a graph of Antifactor Xa activity versus time for beagles administered the formulations described in Tables 35a and 35b, and prepared as described in Example 15, administered as described in Example 19.

The average Antifactor Xa concentrations over 240 minutes is shown in FIG. 25.

EXAMPLE 20

Soft gelatin capsules having the formulations shown in Table 35a and 35b, prepared as described in Example 15, were administered to 4 Rhesus Monkeys in across-over design study with a one week washout period. The monkeys were fasted overnight before the experiment and food was returned about 2 hours after dosing the solid. Each dosage form was delivered to the rear of the mouth using a pill gun. After release of the dosage form, 5 ml of reverse osmosis water was administered into the oral cavity to facilitate swallowing. Following delivery, the oral cavity was inspected to ensure that the solid was swallowed.

Antifactor Xa activity was measured over a period of about 360 minutes. The results are set forth in the table 38 below:

TABLE 38

Antifactor Xa Pharmacokinetic Results

| Statistics | Formulation | Monkey | $C_{max}$ (IU/mL) | $t_{max}$ (min) | $AUC_{last}$ |
|---|---|---|---|---|---|
| | Table 35a | A | 0.810 | 50.0 | 144 |
| | Table 35a | B | 0.810 | 90.0 | 182 |
| | Table 35a | C | 2.60 | 120 | 509 |
| | Table 35a | D | 0.790 | 50.0 | 152 |
| Mean | Table 35a | | 1.25 | 77.5 | 247 |
| SD | Table 35a | | 0.898 | 34.0 | 176 |
| % CV | Table 35a | | 71.7 | 43.9 | 71.3 |
| | Table 35b | A | 0.570 | 90.0 | 54.3 |
| | Table 35b | B | 0.520 | 90.0 | 53.1 |
| | Table 35b | C | 3.70 | 90.0 | 760 |
| | Table 35b | D | 0.930 | 90.0 | 152 |
| Mean | Table 35b | | 1.43 | 90.0 | 255 |
| SD | Table 35b | | 1.52 | 0 | 340 |
| % CV | Table 35b | | 107 | 0 | 133 |

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

We claim:

1. A solid pharmaceutical composition comprising:
   (a) a delivery agent; and
   (b) wetted heparin,
   wherein the delivery agent is of the formula:

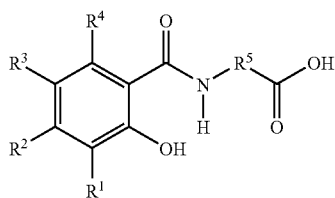

wherein
$R^1$, $R^2$, $R^3$ and $R^4$ are independently hydrogen, —OH, —$NR^6R^7$, halogen $C_1$-$C_4$ alkyl, or $C_1$-$C_4$ alkoxy;
$R^5$ is a substituted or unsubstituted $C_2$-$C_{16}$ alkylene, or substituted or unsubstituted $C_2$-$C_{16}$ alkenylene; and
$R^6$ and $R^7$ are independently hydrogen, oxygen or $C_1$-$C_4$ alkyl.

2. The solid pharmaceutical composition of claim 1, wherein the delivery agent is selected from N-(8-[2-hydroxybenzoyl]-amino)caprylic acid, N-(10-[2-hydroxybenzoyl]amino)decanoic acid, 8-(N-2-hydroxy-5-chlorobenzoyl)aminocaprylic acid, 8-(N-2-Hydroxy-4-methoxybenzoyl)aminocaprylic acid, 4-[(4-chloro, 2-hydroxybenzoyl)-amino]butanoic acid, pharmaceutically acceptable salts thereof, and mixtures thereof.

3. The solid pharmaceutical composition of claim 2, wherein the delivery agent is N-[8-(2-hydroxybenzoyl)amino]caprylic acid or a pharmaceutically acceptable salt thereof.

4. The solid pharmaceutical composition of claim 3, wherein the delivery agent is monosodium N-[8-(2-hydroxybenzoyl)amino] caprylate.

5. The solid pharmaceutical composition of claim 3, wherein the delivery agent is N-(10-[2-hydroxybenzoyl]amino)decanoic acid, or a pharmaceutically acceptable salt thereof.

6. The solid pharmaceutical composition of claim 1, wherein the heparin in the wetted heparin is selected from unfractionated heparin, heparinoids, dermatans, chondroitins, low molecular weight heparin, very low molecular weight heparin, ultra low molecular weight heparin, and mixtures thereof.

7. The solid pharmaceutical composition of claim 1, wherein the heparin in the wetted heparin is unfractionated heparin.

8. The solid pharmaceutical composition of claim 1, wherein the heparin in the wetted heparin is low molecular weight heparin.

9. The solid dosage form of claim 1, wherein the heparin in the wetted heparin is very low molecular weight heparin.

10. The solid pharmaceutical composition of claim 1, wherein the heparin in the wetted heparin is ultra low molecular weight heparin.

11. The solid pharmaceutical composition of claim 1, wherein the ratio of the delivery agent to the heparin (mg to USP heparin units) in the wetted heparin ranges from about 1:20 to about 1:400.

12. The solid pharmaceutical composition of claim 1, wherein the delivery agent and wetted heparin are gelled together.

13. The solid pharmaceutical composition of claim 1, further comprising a gelling agent.

14. The solid pharmaceutical composition of claim 1, wherein the solid pharmaceutical composition comprises a sufficient amount of delivery agent to cause gelling of the delivery agent and wetted heparin.

15. The solid pharmaceutical composition of claim 1, wherein the wetted heparin comprises heparin and a wetting agent.

16. The solid pharmaceutical composition of claim 15, wherein the delivery agent is partially solubilized by the wetting agent.

17. A solid dosage form comprising the solid pharmaceutical composition of claim 1.

18. The solid dosage form of claim 17, wherein the solid dosage form is a tablet.

19. The solid dosage form of claim 17, wherein the solid dosage form is a capsule.

20. The solid dosage form of claim 19, wherein the solid dosage form is a soft gelatin capsule.

21. The solid dosage form of claim 19, wherein the solid dosage form is a hard gelatin capsule.

22. The solid pharmaceutical composition of claim 1, wherein the dosage of heparin is greater than about 150,000 IU.

23. The solid pharmaceutical composition of claim 22 wherein the dosage of heparin is about 15,000 IU to about 150,000 IU.

24. The solid pharmaceutical composition of claim 23 wherein the dosage of heparin is about 25,000 IU to about 90,000 IU.

25. The solid pharmaceutical composition of claim 24 wherein the dosage of heparin is about 30,000 IU to about 80,000 IU.

26. The solid pharmaceutical composition of claim 25 wherein the dosage of heparin is about 37,500 IU to about 75,000 IU.

27. The solid pharmaceutical composition of claim 26 wherein the dosage of heparin is about 37,500 IU.

28. The solid pharmaceutical composition of claim 26 wherein the dosage of heparin is about 40,000 IU.

29. The solid pharmaceutical composition of claim 26 wherein the dosage of heparin is about 50,000 IU.

30. The solid pharmaceutical composition of claim 26 wherein the dosage of heparin is about 60,000 IU.

31. The solid pharmaceutical composition of claim 26 wherein the dosage of heparin is about 75,000 IU.

32. The solid pharmaceutical composition of claim 4 wherein the dosage of monosodium N-[8-(2-hydroxybenzoyl)amino] caprylate is less than about 2.4 g.

33. The solid pharmaceutical composition of claim 32 wherein the dosage of monosodium N-[8-(2-hydroxybenzoyl)amino] caprylate is less than about 2.2 g.

34. The solid pharmaceutical composition of claim 33 wherein the dosage of monosodium N-[8-(2-hydroxybenzoyl)amino] caprylate is less than about 1.8 g.

35. The solid pharmaceutical composition of claim 34 wherein the dosage of monosodium N-[8-(2-hydroxybenzoyl)amino] caprylate is less than about 1.2 g.

36. The solid pharmaceutical composition of claim 35 wherein the dosage of monosodium N-[8-(2-hydroxybenzoyl)amino] caprylate is less than about 1 g.

37. The solid pharmaceutical composition of claim 36 wherein the dosage of monosodium N-[8-(2-hydroxybenzoyl)amino] caprylate is less than about 0.9 g.

38. The solid pharmaceutical composition of claim 37 wherein the dosage of monosodium N-[8-(2-hydroxybenzoyl)amino] caprylate is less than about 0.8 g.

39. The solid pharmaceutical composition of claim 38 wherein the dosage of monosodium N-[8-(2-hydroxybenzoyl)amino] caprylate is less than about 0.7 g.

40. The solid pharmaceutical composition of claim 39 wherein the dosage of monosodium N-[8-(2-hydroxybenzoyl)amino] caprylate is less than about 0.6 g.

41. The solid pharmaceutical composition of claim 40 wherein the dosage of monosodium N-[8-(2-hydroxybenzoyl)amino] caprylate is less than or equal to about 0.5 g.

42. The solid pharmaceutical composition of claim 4 wherein the dosage of monosodium N-[8-(2-hydroxybenzoyl)amino] caprylate is about 50 mg to about 2.4 g.

43. The solid pharmaceutical composition of claim 42 wherein the dosage of monosodium N-[8-(2-hydroxybenzoyl)amino] caprylate is about 100 mg to about 1.2 g.

44. The solid pharmaceutical composition of claim 43 wherein the dosage of monosodium N-[8-(2-hydroxybenzoyl)amino] caprylate is about 900 mg to about 1.2 g.

45. The solid pharmaceutical composition of claim 44 wherein the dosage of monosodium N-[8-(2-hydroxybenzoyl)amino] caprylate is about 1.15 g.

46. The solid pharmaceutical composition of claim 43 wherein the dosage of monosodium N-[8-(2-hydroxybenzoyl)amino] caprylate is about 125 mg to about 1 g.

47. The solid pharmaceutical composition of claim 46 wherein the dosage of monosodium N-[8-(2-hydroxybenzoyl)amino] caprylate is about 250 mg to about 750 mg.

48. The solid pharmaceutical composition of claim 47 wherein the dosage of monosodium N-[8-(2-hydroxybenzoyl)amino] caprylate is about 400 mg to about 600 mg.

49. The solid pharmaceutical composition of claim 48 wherein the dosage of monosodium N-[8-(2-hydroxybenzoyl)amino] caprylate is about 500 mg.

50. A method for administering heparin to an animal comprising the step of administering the solid pharmaceutical composition or dosage form of claim 1.

51. A method of treating or preventing thrombosis in an animal comprising orally administering an anti-thrombosis effective amount of the solid pharmaceutical composition or dosage form of claim 1.

52. The method of claim 51, wherein the thrombosis is deep vein thrombosis or pulmonary embolism.

53. The method of claim 51 wherein said effective amount is sufficient to increase the activated partial thromboplastin time by at least about 100% as compared to an untreated state of the same subject.

54. The method of claim 53 wherein said effective amount is sufficient to increase the activated partial thromboplastin time by at least about 150% as compared to an untreated state of the same subject.

55. The method of claim 54 wherein said effective amount is sufficient to increase the activated partial thromboplastin time by at least about 165% as compared to an untreated state of the same subject.

56. The method of claim 55 wherein said effective amount is sufficient to increase the activated partial thromboplastin time by at least about 200% as compared to an untreated state of the same subject.

57. The method of claim 51 wherein said effective amount is sufficient to increase the AntiFactor Xa to about 0.05 to about 0.4 IU/ml.

58. The method of claim 57 wherein said effective amount is sufficient to increase the AntiFactor Xa to about 0.15 to about 0.35 IU/ml.

59. The method of claim 58 wherein said effective amount is sufficient to increase the AntiFactor Xa to about 0.15 to about 0.20 IU/ml.

60. The method of claim 59 wherein said effective amount is sufficient to increase the AntiFactor Xa to about 0.2 IU/ml.

61. The method of claim 51 wherein said effective amount is sufficient to increase the AntiFactor Xa to greater than about 0.05 IU/ml.

62. The method of claim 61 wherein said effective amount is sufficient to increase the AntiFactor Xa to greater than about 0.1 IU/ml.

63. The method of claim 62 wherein said effective amount is sufficient to increase the AntiFactor Xa to greater than about 0.15 IU/ml.

64. A method of preparing a solid dosage form of wetted heparin comprising the steps of:
(a) blending a delivery agent and heparin;
(b) adding the delivery agent and heparin to a wetting agent to obtain a composition containing wetted heparin, wherein the delivery agent is of the formula:

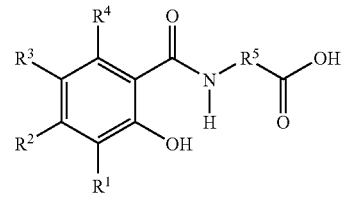

wherein
R¹, R², R³ and R⁴ are independently hydrogen, —OH, —NR⁶R⁷, halogen, $C_1$-$C_4$ alkyl, or $C_1$-$C_4$ alkoxy;
R⁵ is a substituted or unsubstituted $C_2$-$C_{16}$ alkylene, or substituted or unsubstituted $C_2$-$C_{16}$ alkenylene; and
R⁶ and R⁷ are independently hydrogen, oxygen, or $C_1$-$C_4$ alkyl.

65. The method of claim 64, wherein the heparin in the wetted heparin is selected from unfractionated heparin, heparinoids, dermatans, chondroitins, low molecular weight heparin, very low molecular weight heparin, ultra low molecular weight heparin, and mixtures thereof.

66. The method of claim 64, wherein the heparin in the wetted heparin is unfractionated heparin.

67. The method of claim 64, wherein the heparin in the wetted heparin is low molecular weight heparin.

68. The solid dosage form of claim 64, wherein the heparin in the wetted heparin is very low molecular weight heparin.

69. The method of claim 64, wherein the heparin in the wetted heparin is ultra low molecular weight heparin.

70. A method of improving the bioavailability of a solid heparin dosage form containing unwetted heparin, comprising the step of:
(a) substituting the unwetted heparin in the dosage form with wetted heparin.

71. The method of claim 70, wherein the heparin in the wetted heparin is selected from unfractionated heparin, heparinoids, dermatans, chondroitins, low molecular weight heparin, very low molecular weight heparin, ultra low molecular weight heparin, and mixtures thereof.

72. The method of claim 70, wherein the heparin in the wetted heparin is unfractionated heparin.

73. The method of claim 70, wherein the heparin in the wetted heparin is low molecular weight heparin.

74. The method of claim 70, wherein the heparin in the wetted heparin is very low molecular weight heparin.

75. The method of claim 70, wherein the heparin in the wetted heparin is ultra low molecular weight heparin.

76. A method of preventing thrombosis in an animal comprising orally administering an anti-thrombosis effective amount of the solid pharmaceutical composition or dosage form of claim 1.

77. The method of claim 76, wherein the thrombosis is deep vein thrombosis or pulmonary embolism.

78. The method of claim 76 wherein said effective amount is sufficient to increase the activated partial thromboplastin time by less than or equal to about 10% as compared to an untreated state of the same patient.

79. The method of claim 78 wherein said effective amount is sufficient to increase the activated partial thromboplastin time by about 10%.

80. The method of claim 79 wherein no or a decreased number of thrombosis is seen as compared to an untreated patient.

81. The method of claim 76 wherein said effective amount is sufficient to increase the activated partial thromboplastin time by more than about 10% as compared to an untreated state of the same patient.

82. The method of claim 76 wherein said effective amount is sufficient to increase the AntiFactor Xa to about 0.05 to about 0.4 IU/ml.

83. The method of claim 82 wherein said effective amount is sufficient to increase the AntiFactor Xa to about 0.15 to about 0.35 IU/ml.

84. The method of claim 83 wherein said effective amount is sufficient to increase the AntiFactor Xa to about 0.25 IU/ml.

85. The method of claim 51 wherein said animal is a mammal.

86. The method of claim 85 wherein said mammal is a human.

87. The method of claim 76 wherein said animal is a mammal.

88. The method of claim 87 wherein said mammal is a human.

89. A method of treating or preventing deep vein thrombosis in a human in need thereof, the method comprising orally administering one or more solid pharmaceutical compositions comprising monosodium N-[8-(2-hydroxybenzoyl) amino] caprylate and wetted heparin, wherein
(1) 120 minutes after oral administration of the solid pharmaceutical composition to a human, the human exhibits one or more of the following:
(i) a plasma activated partial thromboplastin time of at least about 38 seconds,
(ii) an anti-factor IIa plasma concentration of at least about 0.11 IU/ml, or
(iii) an anti-factor Xa plasma concentration of at least about 0.1 IU/ml,
(2) after oral administration of the solid pharmaceutical composition to a human, the human exhibits one or more of the following:
(i) an $E_{max}$ for activated partial thromboplastin time of at least about 50 IU/ml,
(ii) an $E_{AUC(0-inf)}$ for activated partial thromboplastin time of at least 80 IU * hr/ml,
(iii) an $E_{max}$ for anti-factor IIa of at least about 0.35 IU/ml,
(iv) an $E_{AUC(0-inf)}$ for anti-factor IIa of at least about 0.7 IU * hr/ml,
(v) an $E_{max}$ for anti-factor Xa of at least about 0.35 IU/ml,
(vi) an $E_{AUC(0-inf)}$ for anti-factor Xa of at least about 0.68 IU * hr/ml, or
(3) both.

90. The method of claim 89, wherein the human exhibits a plasma activated partial thromboplastin time of at least about 39 seconds.

91. The method of claim 89, wherein the human exhibits a plasma activated partial thromboplastin time of at least about 50 seconds.

92. The method of claim 89, wherein the human exhibits an antifactor IIa plasma concentration of at least about 0.2 IU/ml.

93. The method of claim 89, wherein the human exhibits an antifactor Xa plasma concentration of at least about 0.2 IU/ml.

94. The method of claim 89, wherein the human exhibits an $E_{AUC(0-inf)}$ for activated partial thromboplastin time of at least about 100 IU * hr/ml.

95. The method of claim 89, wherein the human exhibits an $E_{AUC(0-inf)}$ for activated partial thromboplastin time of at least about 150 IU * hr/ml.

96. The method of claim 89, wherein the human exhibits an $E_{AUC(0-inf)}$ for activated partial thromboplastin time of at least about 180 IU * hr/ml.

97. The method of claim 89, wherein the human exhibits an $E_{max}$ for anti-factor IIa of at least about 0.4 IU/ml.

98. The method of claim 89, wherein the human exhibits an $E_{AUC(0-inf)}$ for anti-factor IIa of at least about 1.0 IU * hr/ml.

99. The method of claim 89, wherein the human exhibits an $E_{max}$ for anti-factor Xa of at least about 0.4 IU/ml.

100. The method of claim 89, wherein the human exhibits an $E_{AUC(0\text{-}inf)}$ for anti-factor Xa of at least about 1.0 IU * hr/ml.

101. The method of claim 89, wherein the heparin in the wetted heparin is selected from unfractionated heparin, heparinoids, dermatans, chondroitins, low molecular weight heparin, very low molecular weight heparin, ultra low molecular weight heparin, and mixtures thereof.

102. The method of claim 89, wherein the heparin in the wetted heparin is unfractionated heparin.

103. The method of claim 89, wherein the heparin in the wetted heparin is low molecular weight heparin.

104. The method of claim 89, wherein the heparin in the wetted heparin is very low molecular weight heparin.

105. The method of claim 89, wherein the heparin in the wetted heparin is ultra low molecular weight heparin.

* * * * *